United States Patent
Nevalaita et al.

(10) Patent No.: US 9,579,362 B2
(45) Date of Patent: Feb. 28, 2017

(54) SPLICE VARIANTS OF GDNF AND USES THEREOF

(76) Inventors: Liina Nevalaita, Helsinki (FI); Mart Saarma, Helsinki (FI)

( * ) Notice: Subject to any disclaimer, the term of this patent is extended or adjusted under 35 U.S.C. 154(b) by 871 days.

(21) Appl. No.: 12/739,715

(22) PCT Filed: Oct. 24, 2008

(86) PCT No.: PCT/FI2008/050599
§ 371 (c)(1),
(2), (4) Date: Jul. 22, 2010

(87) PCT Pub. No.: WO2009/053536
PCT Pub. Date: Apr. 30, 2009

(65) Prior Publication Data
US 2010/0311653 A1    Dec. 9, 2010

Related U.S. Application Data

(60) Provisional application No. 60/983,281, filed on Oct. 29, 2007.

(30) Foreign Application Priority Data

Oct. 25, 2007  (FI) .................................. 20070808

(51) Int. Cl.
*A61K 48/00* (2006.01)
*A61K 38/18* (2006.01)
*C07K 14/475* (2006.01)
*A61K 39/00* (2006.01)

(52) U.S. Cl.
CPC ........ *A61K 38/185* (2013.01); *A61K 48/0058* (2013.01); *C07K 14/475* (2013.01); *A61K 39/00* (2013.01)

(58) Field of Classification Search
None
See application file for complete search history.

(56) References Cited

U.S. PATENT DOCUMENTS 6,610,836 B1    8/2003    Breton et al.

FOREIGN PATENT DOCUMENTS

| DE | 198 16 186 A1 | 10/1999 |
|---|---|---|
| WO | WO 99/53091 A2 | 10/1999 |
| WO | WO 03/053476 A1 | 7/2003 |
| WO | WO 2005/023861 A2 | 3/2005 |
| WO | WO 2007/048413 A1 | 5/2007 |
| WO | WO 2007/103182 A2 | 9/2007 |

OTHER PUBLICATIONS

Orkin and Motulsky, "Report and Recommendations of the Panel to Assess the NIH Investment in Research on Gene Therapy", NIH home page (Dec. 7, 1995).*
Jackowski, British J Neurosurgery 9:303-317 (1995).*
Finnish Search Report issued in Finnish Application No. 20070808 on May 15, 2008.
Grimm et al., "Analysis of the human GDNF gene reveals an inducible promoter, three exons, a triplet repeat within the 3'-UTR and alternative splice products", Human Molecular Genetics, vol. 7, No. 12, (1998) pp. 1873-1886.
He et al., "Glial Cell Line-Derived Neurotrophic Factor Mediates the Desirable Actions of the Anti-Addiction Drug Ibogaine against Alcohol Consumption," The Journal of Neuroscience, vol. 25, No. 3 (2005) pp. 619-628.
International Search Report issued in International Application No. PCT/FI2008/050599 dated Apr. 29, 2009.
Sequence Alignment of Sequence 22 of WO 99/53091 (Accession No. AX014685) with SEQ ID No. 1.
Suter-Crazzolara et al., "GDNF is expressed in two forms in many tissues outside the CNS," NeuroReport, vol. 5, No. 18 (1994) pp. 2486-2488.
Trupp et al., "Peripheral Expression and Biological Activities of GDNF, a New Neurotrophic Factor for Avian and Mammalian Peripheral Neurons," The Journal of Cell Biology, vol. 130, No. 1 (1995) pp. 137-148.

* cited by examiner

*Primary Examiner* — Robert C Hayes
(74) *Attorney, Agent, or Firm* — Birch, Stewart, Kolasch & Birch, LLP

(57) ABSTRACT

The present invention relates to Glial Cell Line-Derived Neurotrophic Factor (GDNF) protein and gene and is, in particular, directed to a novel splice variant of GDNF protein, which is encoded by a novel splice variant pre-(γ) pro-GDNF, and secreted under biological regulation.

7 Claims, 14 Drawing Sheets

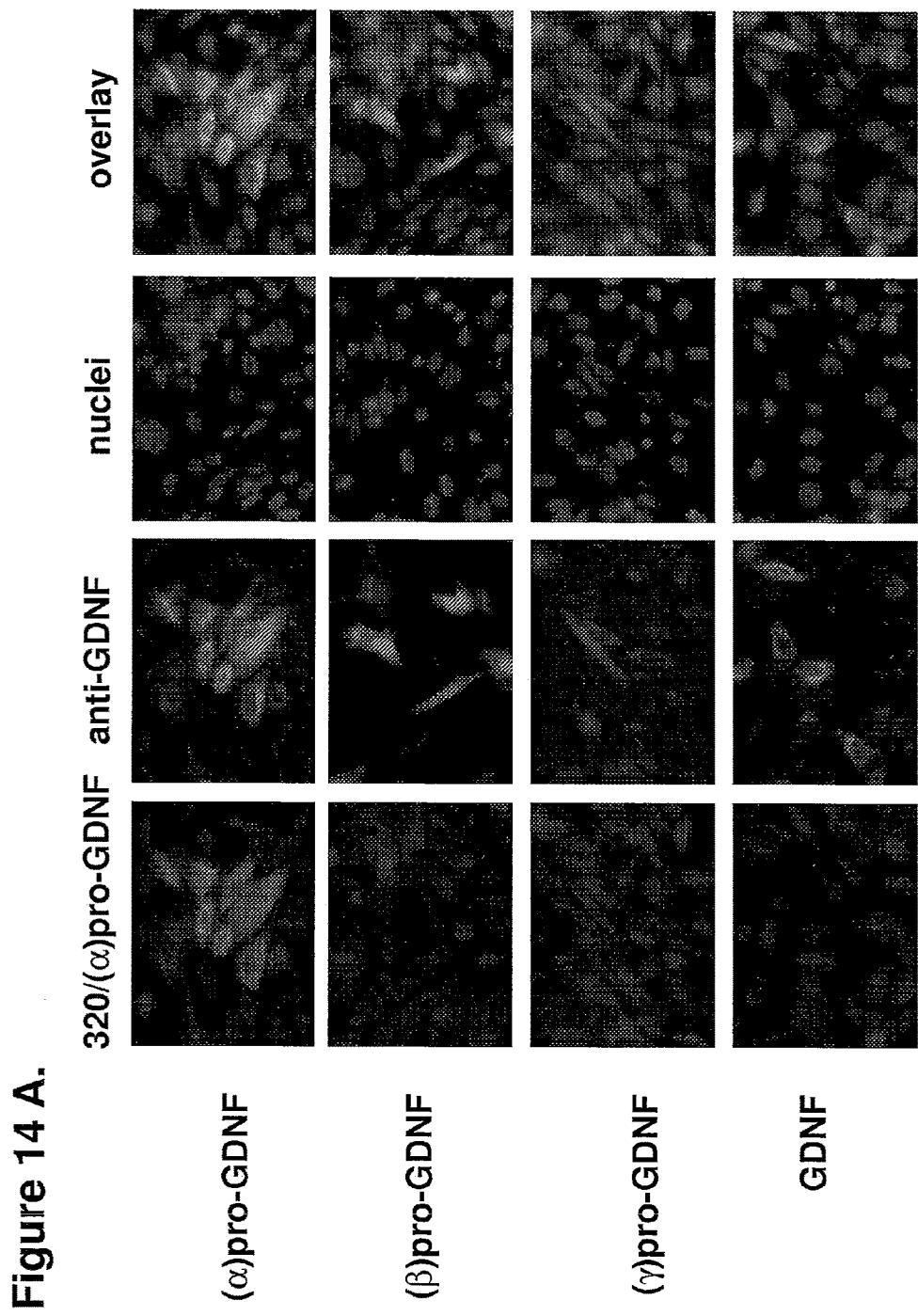

SPLICE VARIANTS OF GDNF AND USES THEREOF

This Non-Provisional application is the National Phase of PCT/FI2008/050599 filed Oct. 24, 2008, which claims priority under 35 U.S.C. §119(e) to U.S. Provisional Application No. 60/983,281 filed on Oct. 29, 2007, and under 35 U.S.C. §119(a) to Patent Application No. 20070808 filed in Finland on Oct. 25, 2007, all of which are hereby expressly incorporated by reference into the present application.

FIELD OF THE INVENTION

The present invention relates to Glial Cell Line-Derived Neurotrophic Factor (GDNF) protein and its cDNA and is, in particular, directed to a novel splice variant of GDNF protein, named as (γ)pro-GDNF, which is encoded by a novel mRNA splice variant pre-(γ)pro-GDNF, and secreted in a neuronal activity-dependent manner. The present invention relates to the use of (γ)pro-GDNF protein, its cDNA and its parts.

BACKGROUND OF THE INVENTION

GDNF is a neurotrophic factor that supports the development and survival of peripheral sympathetic, parasympathetic, enteric and sensory neurons as well as midbrain dopamine neurons and motoneurons. In various animal models of Parkinson's disease (PD) GDNF can prevent the neurotoxin-induced death of dopamine neurons and can promote axonal sprouting leading to functional recovery. Two GDNF splice variants, called pre-(α)pro-GDNF (previously called GDNFα) and pre-(β)pro-GDNF (previously called GDNFβ), have been described (Suter-Crazzolara and Unsicker, Neuroreport, 5:2486-2488 (1994)). These splice variants are produced by alternative splicing of the GDNF mRNA.

Many secreted proteins, including neurotrophic factors, are synthesized in the forms of precursors, pre-pro-mature proteins. The pre-region, consisting of the ER signal peptide, is clipped off during translation by a signal peptidase, and the pro-mature protein is released into the lumen of the ER immediately after being synthesized. The proteolytic cleavage of the mature protein can occur either inside the cell or in the extracellular matrix, or both. The pro-mature protein can also remain uncleaved and have different function than the cleaved mature protein. For example, both mature brain-derived neurotrophic factor (BDNF) and pro-BDNF are secreted from neuronal cells. Mature BDNF binds to TrkB receptor inducing neuronal survival, differentiation and synaptic modulation, whereas pro-BDNF binds to $p75^{NTR}$ and sortilin receptors inducing apoptosis (to review, see Thomas and Davies, Curr. Biol., 15:262-264 (2005); Teng et al., J. Neurosci., 25:5455-5463 (2005)).

The GDNF splice variants contain an amino terminal signal sequence (pre-region) and a pro-sequence which is cleaved from the mature domain (Lin et al., Science, 260:1130-1132 (1993)) (FIG. 1). The pro-region of (β)pro-GDNF is 26 amino acids (aa) shorter than the pro-region of (α)pro-GDNF (Trupp et al., J. Cell Biol., 130:137-148 (1995)). The mature GDNF proteins produced by both of these splice variants are most likely identical. Mature GDNF consists of 134 amino acids (aa) and contains two putative N-glycosylation sites as well as seven conserved cysteines in the same relative spacing as the other members of the TGF-β protein family (Lin et al., Science, 260:1130-1132 (1993); Eigenbrot and Gerber, Nat. Struct. Biol., 4:435-438 (1997); Chang et al., Endocri. Rev., 23:787-823 (2002)) (FIG. 1). The biologically active mature GDNF dimer is formed by a covalent disulfide bond between the unpaired cysteines in the monomers (Eigenbrot and Gerber, Nat. Struct. Biol. 4:435-438 (1997)).

In the scientific text, the names GDNF mRNA and GDNF protein have been used for the full-length pre-(α)pro-GDNF mRNA and for the mature GDNF protein that is produced by proteolytic cleavage of the (α)pro-GDNF protein. This mature GDNF protein has been extensively studied, and in PubMed more than 2500 citations are available for GDNF. GDNF was identified based on its ability to increase neurite length, cell size, and the number of dopaminergic neurons as well as their high affinity dopamine uptake in culture (Lin et al., Science, 260:1130-1132 (1993)). GDNF is a potent factor for the protection of nigral dopaminergic neurons against their toxin-induced degeneration in animal models of PD and also in the treatment of patients with PD (reviewed in Airaksinen and Saarma, Nat. Rev. Neurosci. 3:383-394 (2002) and Bespalov and Saarma, Trends Pharmacol. Sci. 28:68-74 (2007)). In addition, GDNF has a therapeutic role in the treatment of animal models of amyotrophic lateral sclerosis (ALS), addiction, alcoholism and depression (reviewed in Bohn, Exp. Neurol., 190:263-275 (2004); Messer et al., Neuron, 26:247-257 (2000); He et al., J. Neurosci., 25:619-628 (2005); Angelucci et al., Int. J. Neuropsychopharmacol., 6:225-231 (2003)). GDNF has important roles also outside the nervous system. It acts as a morphogen in kidney development and regulates the differentiation of spermatogonia (reviewed in Sariola and Saarma, J. Cell Sci. 116:3855-3862 (2003)).

The (α)pro-GDNF protein is disclosed in, e.g., U.S. Pat. No. 6,362,319 and European Patent No. 0 610 254, and a truncated form of GDNF in U.S. Pat. No. 6,184,200 and European Patent No. 0 920 448. Clinical trials for the treatment of Parkinson's disease have been carried out using the mature GDNF protein. Preclinical studies gave promising results (Gill et al., Nat. Med., 9:589-595 (2003); Slevin et al., J. Neurosurg., 102:401 (2005)), but the outcome of the Phase I/II trial was found disappointing. It was reported that improvements in Parkinson's symptoms were not statistically significant, and that there were potential safety risks. Therefore, the clinical trials with mature GDNF protein were totally halted (Lang et al., Ann Neurol., 59:459-466 (2006)).

The existence of the pre-(β)pro-GDNF mRNA splice variant was first described in rat tissues in 1994 by Suter-Crazzolara and Unsicker (Neuroreport, 5:2486-2488), in mouse tissues in 1997 by Matsushita et al. (Gene, 203:149-157 (1997)) and in human tissues in 1998 by Grimm et al. (Hum. Mol. Genet., 12:1873-1886 (1998)). In addition to mRNA expression data, Trupp et al. (J. Cell Biol., 130:137-148 (1995)) showed that the secreted GDNF protein, encoded by the pre-(β)pro-GDNF cDNA, promoted robust survival, extensive neurite outgrowth and increased cell body size in E10 chick paravertebral sympathetic neurons.

SUMMARY OF THE INVENTION

The present invention described in this application shows that, in addition to the prior known GDNF mRNA splice variants called pre-(α)pro-GDNF and pre-(β)pro-GDNF, a third alternative splice variant, named as pre-(γ)pro-GDNF, exists (FIGS. 3 and 4). The open reading frames (ORFs) of human pre-(α)pro-GDNF and pre-(β)pro-GDNF start from exon 2, whereas the pre-(γ)pro-GDNF splice variant lacks the entire exon 2 sequence and contains an alternative protein translation initiation codon CTG in exon 1 (FIG. 2).

The pre-pro region of (γ)pro-GDNF protein, encoded by pre-(γ)pro-GDNF mRNA, is 47 amino acids (aa) long and is 30 aa shorter than the pre-pro region of (α)pro-GDNF (FIG. 1). The 26 C-terminal aa of the pre-pro region of pre-(γ) pro-GDNF are encoded by exon 3 and are thus identical to the corresponding regions in pre-(α)pro-GDNF and pre-(β) pro-GDNF. The first 21 aa of the (γ)pro-GDNF, encoded by exon 1, are unique for this splice variant (FIG. 2). The mature GDNF proteins produced by all of the three GDNF splice variants are most likely identical (FIG. 1).

Our results show that (α)pro-GDNF, (β)pro-GDNF and (γ)pro-GDNF are secreted as pro-GDNF proteins as well as mature proteins, which are generated by proteolytic cleavage of pro-GDNF. The secretion of (α)pro-GDNF and mature GDNF is constitutive, whereas the secretion of (β)pro-GDNF and (γ)pro-GDNF is neuronal activity-dependent i.e. regulated by neuronal and neurophysiological stimuli. This makes (β)pro-GDNF and (γ)pro-GDNF and their encoding cDNAs much more potential therapeutic molecules for gene therapy treatment of PD than (α)pro-GDNF and its cDNA.

Consequently, the primary object of the present invention is a purified and isolated human (γ)pro-GDNF protein splice variant comprising the amino acid sequence as set forth in SEQ ID NO:2, and encoded by the human pre-(γ)pro-GDNF splice variant. As a comparison we have also purified and isolated the mouse (γ)pro-GDNF protein splice variant, comprising the amino acid sequence as set forth in SEQ ID NO:4, and encoded by the mouse pre-(γ)pro-GDNF splice variant.

A further object of the invention is a modification of the human (γ)pro-GDNF protein splice variant, wherein the amino terminal leucine residue has been replaced with a methionine residue. The amino acid sequence of said modification is set forth in SEQ ID NO:6.

Another object of the invention is the mature polypeptide moiety of human pre-(γ)pro-GDNF comprising amino acids 1 through 134 of SEQ ID NO:2, together with the (γ)pro-sequence, i.e. the moiety of the sequence of amino acids −47 through −1 of SEQ ID NO:2 which has the regulatory function but lacks the signal sequence.

An object of the invention is the pre-pro amino acid sequence of human (γ)pro-GDNF protein splice variant, as well as the modified pre-pro sequence, the amino acid sequences of which are set forth in SEQ ID NO:19 and SEQ ID NO:21, respectively. The (γ)pro moiety of the pre-pro sequence as set forth in SEQ ID NO:21 which has the regulatory function is also included in the invention.

Truncated forms of the human (γ)pro-GDNF protein splice variant, lacking 38 amino acids from the N-terminus of the mature polypeptide moiety (SEQ ID NO:24), and the Leu-Met modification thereof as described above (SEQ ID NO:26), are further objects of the invention.

Also V34M mutations of the human (γ)pro-GDNF splice variant (SEQ ID NO:27), and the Leu-Met modification thereof as described above (SEQ ID NO:29), are objects of the invention.

A still further aspect of the invention is a purified, isolated and V38M mutated human Glial Cell Line-Derived Neurotrophic Factor (GDNF) protein splice variant (pre-(β)pro-GDNF), as well as a truncated form of said pre-(β)pro-GDNF, lacking 38 amino acids from the N-terminus of the mature polypeptide moiety. The amino acid sequences of these proteins are set forth in SEQ ID NO:31 and SEQ ID NO:35, respectively. Furthermore, use of pre-(β)pro-GDNF splice variant and the polynucleotide encoding the same (as set forth in SEQ ID NO:51) for treating a neurological disorder or neurodegenerative disease, especially using gene therapy, is one specific aspect of the invention.

The invention further contemplates a purified, isolated and V64M mutated human Glial Cell Line-Derived Neurotrophic Factor (GDNF) protein splice variant (pre-(α)pro-GDNF). The amino acid sequence thereof is set forth in SEQ ID NO:33.

Still further objects of the invention are isolated polynucleotides encoding the above-indicated forms of the GDNF protein splice variants.

Antibodies that specifically bind to the (γ)pro-GDNF protein splice variant form a still further object of the invention. Antibodies which specifically bind to the pro moieties of the (α)pro-GDNF, (β)pro-GDNF and/or (γ)pro-GDNF protein splice variants are also provided. Furthermore, antibodies that specifically bind to the pre-pro regions of the pre-(α)pro-GDNF, pre-(β)pro-GDNF or pre-(γ)pro-GDNF protein splice variants are also contemplated.

One preferred option of the invention provides the protein encoded by the human pre-(γ)pro-GDNF splice variant in recombinant form.

It should be appreciated that there are homologous pre-(γ)pro-GDNF molecules and encoding sequences obtainable from other mammals. As an example mouse (γ)pro-GDNF protein splice variant comprising the amino acid sequence as set forth in SEQ ID NO:4 is provided.

BRIEF DESCRIPTION OF THE DRAWINGS

FIG. 8A: Lane 1 BHK cells transfected with pAAV-MCS vector containing human pre-(γ)pro-GDNF with ATG translation initiation codon, medium; Lane 2 BHK cells transfected with pEGFP-N1 vector containing human pre-(γ)pro-GDNF with CTG translation initiation codon and stop codon, medium. FIG. 8B: Lane 1 COS-7 cells transfected with pAAV-MCS vector containing human pre-(γ)pro-GDNF with ATG translation initiation codon, medium; Lane 2 non-transfected COS-7 cells (negative control), medium.

FIG. 9A; Quantitation of the subcellular localizations of the proteins encoded by pre-(α)pro-GDNF (white) or pre-(β)pro-GDNF (gray) in non-stimulated PC-6.3 cells. The percentage of proteins in Golgi alone or in vesicles +/− Golgi (n=3) are shown. *, P=0.0023. Error bars show SD. FIG. 9B; Quantitation of the subcellular localizations of the proteins encoded by pre-(α)pro-GDNF and pre-(β)pro-GDNF in differentiated PC-6.3 cells. The percentage of proteins in Golgi alone, in vesicles +/− Golgi or in vesicles alone (n=3) are shown. The cells were either untreated (0 h) or treated with 50 mM KCl together with 50 µg/ml cycloheximide for 2 h (2 h).

FIG. 12A; Column 1 depolarized PC-6.3 cells transfected with human pre-(α)pro-GDNF, medium; Column 2 non-depolarized PC-6.3 cells transfected with human pre-(α)pro-GDNF, medium; Column 3 depolarized PC-6.3 cells transfected with human pre-(β)pro-GDNF, medium; Column 4 non-depolarized PC-6.3 cells transfected with human pre-(β)pro-GDNF, medium. (n=3). *, P=0.092227. Error bars show SD. FIG. 12B; Column 1 depolarized PC-6.3 cells transfected with rat pre-pro-BDNF, medium; Column 2 non-depolarized PC-6.3 cells transfected with rat pre-pro-BDNF, medium. (n=3). *, P=0.00307. Error bars show SD.

FIG. 13A; Mouse (α)pro-GDNF, human (β)pro-GDNF, human (γ)pro-GDNF and human mature GDNF lacking the pro region were overexpressed in CHO cells and double immunofluorescence stained with 321/pro-GDNF (red) and anti-GDNF (green). Untransfected cells were stained as controls. Nuclei are shown in blue. FIG. 13B; GFP protein (green) was expressed in CHO cells and the cells were immunofluorescence stained with 321/pro-GDNF antibody (red). Nuclei are shown in blue.

GFP was expressed from an empty pEGFP-N1 vector. CHO cells grown in DMEM with 10% FCS and antibiotics were plated on 4-well plates with coverslips and each well was transfected with 0.8 μg of plasmid when grown up to approximately 80% confluence. The media were replaced with fresh DMEM with 10% FCS and antibiotics 4 hrs after transfection. 24 hrs post-transfection, the cells were fixed with 4% paraformaldehyde (Sigma) and permeabilized with 0.1% Triton X-100 (Sigma). Cells were incubated with primary antibodies polyclonal 320/(α)pro-GDNF for (α)pro-GDNF pro-domain (1:200 dilution) and monoclonal mouse anti-GDNF for mature GDNF (1:100 dilution) in 0.5% BSA in RT for 1 hr, washed and then repeated with secondary antibodies. Nuclei were stained with Hoechst. Images were acquired through a charge-coupled device camera (DP70; Olympus) on a microscope (AX70 Provis; Olympus). FIG. 14A; Mouse (α)pro-GDNF, mouse (β)pro-GDNF, human (γ)pro-GDNF and human mature GDNF lacking the pro region were overexpressed in CHO cells and double immunofluorescence stained with 320/(α)-proGDNF (red) and anti-GDNF (green). Nuclei are shown in blue. FIG. 14B; GFP protein (green) was expressed in CHO cells and the cells were immunofluorescence stained with 320/(α)pro-GDNF antibody (red). Nuclei are shown in blue.

FIG. 15A; Mouse (α)pro-GDNF, mouse (β)pro-GDNF, human (γ)pro-GDNF and human mature GDNF lacking the pro region were overexpressed in CHO cells and double immunofluorescence stained with 322/(β)pro-GDNF (red) and anti-GDNF (green). Nuclei are shown in blue. FIG. 15B; GFP protein (green) was expressed in CHO cells and the cells were immunofluorescence stained with 322/(β)pro-GDNF antibody (red). Nuclei are shown in blue.

FIG. 16A; samples detected with 321/pro-GDNF antibody. FIG. 16B; samples detected with D20 antibody. FIG. 16C; (α)pro-GST and (β)pro-GST fusion proteins detected with 321/pro-GDNF antibody.

FIG. 17B; CHO cells detected with 320/(α)pro-GDNF antibody, media. FIG. 17C; CHO cells detected with D20 antibody, cells. FIG. 17D; CHO cells detected with D20 antibody, media.

DETAILED DESCRIPTION OF THE INVENTION

Figure 1:
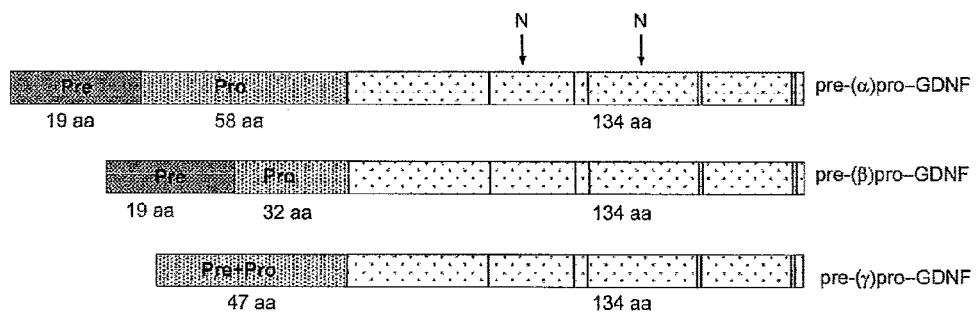
FIG. 1 is a schematic illustration of the structures of the proteins encoded by pre-(α)pro-GDNF, pre-(β)pro-GDNF and pre-(γ)pro-GDNF mRNA. For clarity, amino terminal signal sequences (pre-regions) are included, although they are cleaved during the protein translation. The number of amino acids in mature molecules as ▓, pro-regions as ▓ and pre-regions ▓ are shown. In pre-(γ)pro-GDNF the pre-pro region is indicated as ▓ Relative positions of the seven conserved cysteine residues are shown as black bars. The two putative N-glycosylation sites of GDNF are marked with arrows.
Figure 2:
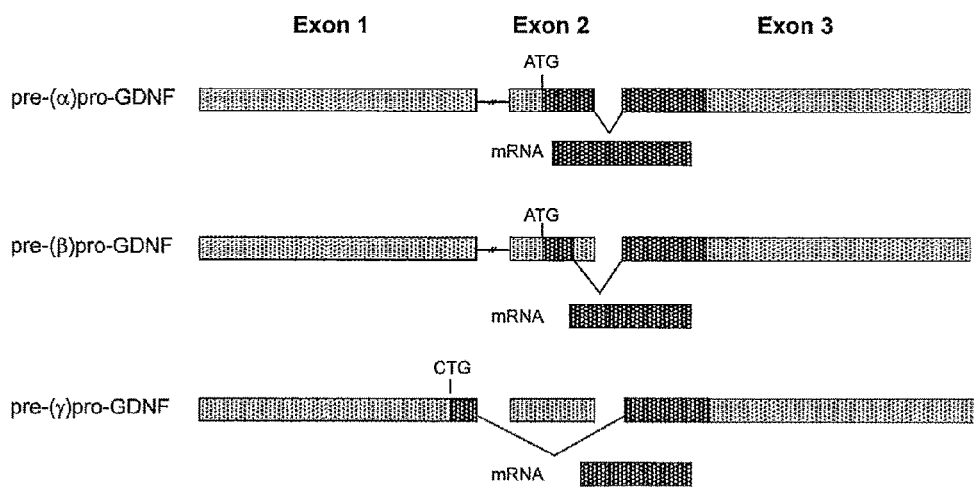
FIG. 2 shows the characteristics of pre-(α)pro-GDNF, pre-(β)pro-GDNF and pre-(γ)pro-GDNF splice variants. In the GDNF cDNA, the ORFs of the splice variants are shown as ▓ and the untranslated (UTR) regions as ▓. The ORFs of pre-(α)pro-GDNF and pre-(β)pro-GDNF are divided into exons 2 and 3 and in pre-(γ)pro-GDNF into exons 1 and 3. The pre-(β)pro-GDNF splice variant lacks 78 bp in the 3' region of exon 2. The pre-(γ)pro-GDNF splice variant contains an alternative protein translation start codon CTG, as well as a unique sequence of 61 bp in exon 1. The mature GDNF is encoded by exon 3 and is most likely identical in all three splice variants.

Abbreviations aa amino acid
ALS Amyotrophic lateral sclerosis
AtT-20 cell line mouse pituitary tumor cell line
BDNF Brain-Derived Neurotrophic Factor BHK-21 Baby hamster kidney cell line
bp base pair
BSA bovine serum albumin
CDR complementary determining region
CHO cell line Chinese Hamster Ovary cell line
COS-7 SV40 transformed monkey kidney cell line
DMEM Dulbecco's modified Eagle's medium
ELISA Enzyme-linked immunosorbent assay
ER endoplasmatic reticulum
FCA Freund's complete adjuvant
FCS fetal calf serum
FIA Freund's incomplete adjuvant
GDNF Glial Cell Line-Derived Neurotrophic Factor
GFP green fluorescent protein
HC hippocampal
HEK-293 cell line Human embryonic kidney cell line
HPLC High Performance Liquid Chromatography
HRP horse radish peroxidase
HS horse serum
KLH keyhole limpet hemocyanin
LTR long terminal repeat
MALDI TOF-MS Matrix Assisted Laser Desorption Ionization Time-of-flight Mass Spectrometry
MPL-TDM monophosphoryl Lipid A, synthetic trehalose dicorynomycolate
NGF nerve growth factor
nt nucleotide
ORF open reading frame
PBS phosphate buffered saline
PC-6.3 cell line Rat pheochromocytoma cell line PC12 clone
PD Parkinson's disease
PFA paraformaldehyde
RT room temperature
RT-PCR Reverse Transcriptase-Polymerase Chain Reaction
SD standard deviation
TMB 3,3',5,5'-tetramethylbenzidine
TGF-β Transforming growth factor β
UTR region untranslated region Using RT-PCR analysis we identified three cDNAs encoding GDNF mRNA splice variants, named pre-(α)pro-GDNF, pre-(β)pro-GDNF and pre-(γ)pro-GDNF, from mouse kidney and brain tissues as well as from human brain, kidney and uterus tissues. To characterize these cDNA molecules further, we cloned them into transfer and expression vectors and sequenced.

The differences between the three GDNF splice variant mRNAs are in exons 1 and 2 encoding the pre-pro regions of the GDNF proteins, whereas the ORF in exon 3 encoding the last 26 aa of the pro-region and the mature GDNF is identical in all three GDNF splice variants. The pre-(β)pro-GDNF mRNA lacks 78 bp in the 3' end of exon 2 compared to pre-(α)pro-GDNF (Grimm et al., Hum. Mol. Genet., 7:1873-1886 (1998)). The pre-(γ)pro-GDNF mRNA lacks the entire exon 2 and includes 61 bp of unique sequence from the 3' end of exon 1 compared to pre-(α)pro-GDNF and pre-(β)pro-GDNF.

To study if human and mouse (β)pro-GDNF and (γ)pro-GDNF are secreted, we analyzed their expression and secretion in different cell lines using transient transfections with cDNAs encoding respective GDNF splice variants and Western blot analysis. It was found that both human and mouse (β)pro-GDNF and their mature GDNFs are secreted from CHO, HEK-293, PC-6.3 and AtT-20 cell lines. In addition, mouse (γ)pro-GDNF and its mature GDNF are secreted from CHO, PC-6.3 and BHK-21 cell lines and human (γ)pro-GDNF, where CTG translation start codon was replaced with ATG start codon, and its mature GDNF are secreted from BHK-21 cell line.

To analyse if the secretion of mouse and human (α)pro-GDNF and (β)pro-GDNF is constitutive or stimulated by neuronal activity, i.e. is activity-dependent, we analyzed their expression and secretion in non-depolarized and depolarized differentiated PC-6.3 cells using transient cDNA transfections, Western blot analysis, ELISA analysis and in rat HC primary cells using transient transfections and ELISA analysis. The results show that (α)pro-GDNF is secreted constitutively, whereas the secretion of (β)pro-GDNF is activity-dependent indicating that the 26 bp deletion in the (β)pro-GDNF pro region is essential for activity-dependent secretion. The (γ)pro-GDNF lacks the same 26 bp in the pro-region suggesting that also its secretion is activity-dependent.

Definitions

Unless otherwise defined, all technical and scientific terms have the same meaning as is commonly understood by one of skill in the art to which this invention belongs. The definitions below are presented for clarity.

"Isolated", when referred to a molecule, refers to a molecule that has been identified and separated and/or recovered from a component of its natural environment and thus is altered "by the hand of man" from its natural state. For example, an isolated polynucleotide could be part of a vector or a composition of matter, or could be contained within a cell, and still be "isolated" because that vector, composition of matter, or particular cell is not the original environment of the polynucleotide. The term "isolated" does not refer to genomic or cDNA libraries, whole cell total or mRNA preparations, genomic DNA preparations, sheared whole cell genomic DNA preparations or other compositions where the art demonstrates no distinguishing features of the polynucleotide sequences of the present invention.

"Nucleic acid molecule", includes DNA molecules (e.g. cDNA or genomic DNA), RNA molecules (e.g., mRNA), analogs of the DNA or RNA generated using nucleotide analogs, and derivatives, fragments and homologs. The nucleic acid molecule may be single-stranded or double-stranded, but preferably comprises double-stranded DNA.

"Isolated nucleic acid molecule" is separated from other nucleic acid molecules which are present in the natural source of the nucleic acid. Preferably, an isolated nucleic acid is free of sequences that naturally flank the nucleic acid (i.e. sequences located at the 5'- and 3'-termini of the nucleic acid) in the genomic DNA of the organism from which the nucleic acid is derived. Moreover, an isolated nucleic acid molecule, such as a cDNA molecule, can be substantially free of other cellular material or culture medium when produced by recombinant techniques, or of chemical precursors or other chemicals when chemically synthesized.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "genomic DNA" is a DNA strand which has a nucleotide sequence homologous with a gene. It is thus the full complement of DNA contained in the genome of a cell or organism.

"Oligonucleotide" comprises a series of linked nucleotide residues, which oligonucleotide has a sufficient number of nucleotide bases to be used in a PCR reaction or another application. A short oligonucleotide sequence may be based on, or designed from, a genomic or cDNA sequence and is used to amplify, confirm, or reveal the presence of an identical, similar or complementary DNA or RNA in a particular cell or tissue. Oligonucleotides comprise portions of a nucleic acid.

"Variant" refers to a polynucleotide or polypeptide differing from the polynucleotide or polypeptide of the present invention, but retaining essential properties thereof. Generally, variants are overall closely similar, and, in many regions, identical to the polynucleotide or polypeptide of the present invention.

"Splice variants" are different mature mRNA molecules that are transcribed from one gene. The splicing process is called alternative splicing and it can occur in eukaryotic cells. The functions of different splice variant proteins, transcribed and translated from one gene, can vary significantly.

"Stringency" homologs (i.e., nucleic acids of pre-(γ)pro-GDNF splice variant molecule derived from species other than human) or other related sequences (e.g., paralogs) can be obtained by low, moderate or high stringency hybridization with all or a portion of the particular human sequence as a probe using methods well known in the art for nucleic acid hybridization and cloning.

Polymerase chain reaction (PCR) amplification techniques can be used to amplify pre-(γ)pro-GDNF splice variant using cDNA, mRNA or, alternatively, genomic DNA as a template and appropriate oligonucleotide primers. Such nucleic acids can be cloned into an appropriate vector and characterized by DNA sequence analysis. Furthermore, oligonucleotides corresponding to pre-(γ)pro-GDNF sequences can be prepared by standard synthetic techniques, e.g., an automated DNA synthesizer.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded.

Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

By the term "vector" as used herein, is meant any plasmid or virus encoding an exogenous nucleic acid. The term should also be construed to include non-plasmid and non-viral compounds which facilitate transfer of nucleic acid into virions or cells, such as, for example, polylysine compounds and the like. The vector may be a viral vector which is suitable as a delivery vehicle for delivery of the nucleic acid encoding the desired protein, or mutant thereof, to a cell, or the vector may be a non-viral vector which is suitable for the same purpose. Examples of viral and non-viral vectors for delivery of DNA to cells and tissues are well known in the art and are described, for example, in Ma et al. (Proc. Natl. Acad. Sci. USA, 94:12744-12746 (1997)). Examples of viral vectors include, but are not limited to, a recombinant vaccinia virus, a recombinant adenovirus, a recombinant retrovirus, a recombinant adeno-associated virus, a recombinant avian pox virus, a recombinant baculovirus, a recombinant papilloma virus, a recombinant lentivirus and the like (Cranage et al., EMBO J., 5:3057-3063 (1986); PCT Application No. WO 94/17810 and PCT Application No. WO 94/23744). Examples of non-viral vectors include, but are not limited to, bacterial, fungal, mammalian, insect, plant or yeast vectors or liposomes, polyamine derivatives of DNA, and the like.

"Probes" are nucleic acid sequences of variable length, preferably between at least about 10 nucleotides (nt), 100 nt, or many (e.g., 6000 nt) depending on the specific use. Probes are used to detect identical, similar, or complementary nucleic acid sequences. Longer length probes can be obtained from a natural or recombinant source, are highly specific, and much slower to hybridize than shorter-length oligomer probes. Probes may be single or double-stranded and designed to have specificity in PCR, membrane-based hybridization technologies, or ELISA-like technologies. Probes will also hybridize to nucleic acid molecules in biological samples, thereby enabling immediate applications in chromosome mapping, linkage analysis, tissue identification and/or typing, and a variety of forensic and diagnostic methods of the invention.

"Homologs" are nucleic acid sequences or amino acid sequences of a particular gene that are derived from different species.

"Percent (%) nucleic acid sequence identity" is defined as the percentage of nucleotides in a candidate sequence that are identical with the nucleotides in the particular protein, after aligning the sequences and introducing gaps, if necessary, to achieve the maximum percent sequence identity.

An ORF is a nucleotide sequence that has a start codon (ATG or CTG) and terminates with one of the three "stop" codons (TAA, TAG, or TGA).

The term "antibody" is used in the broadest sense and specifically covers monoclonal antibodies, antibody compositions with polyepitopic specificity, bispecific antibodies, diabodies, and single-chain molecules, as well as antibody fragments (e.g., Fab, F(ab') and Fv), so long as they exhibit the desired biological activity. It also covers DNA fragments and cDNAs encoding the above-mentioned antibodies and their derivatives.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Köhler et al., Nature, 256: 495 (1975), or may be made by recombinant DNA methods (see, e.g., U.S. Pat. No. 4,816,567 (Cabilly et al.). The "monoclonal antibodies" may also be isolated from phage antibody libraries using the techniques described in Clackson et al., Nature, 352:624-628 (1991) and Marks et al., J. Mol. Biol., 222:581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (Cabilly et al., Proc. Natl. Acad. Sci. USA, 81:3273-3277 (1984); Cabilly et al., Gene, 40:157-161 (1985); Cabilly et al., Gene, 85:553-557 (1989); Morrison et al., Proc. Natl. Acad. Sci. USA, 81:6851-6855 (1984)).

The antibodies of the invention may also comprise polyclonal antibodies. Methods of preparing polyclonal antibodies are known to a man skilled in the art. Polyclonal antibodies can be raised in a mammal, for example, by administering an immunizing agent and, if desired, an adjuvant to various host animals including, but not limited to, rabbits, mice, rats, etc., to induce the production of sera containing polyclonal antibodies specific for the antigen. Typically, the immunizing agent and/or adjuvant will be injected in the mammal by multiple subcutaneous or intraperitoneal injections. The immunizing agent may include the pre-pro-GDNF polypeptide, an appropriate fraction or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation. The mammal can then be bled, and the serum assayed for pre-pro-GDNF antibody titer. If desired, the mammal can be boosted until the antibody titer increases.

"Humanized" forms of non-human (e.g., murine) antibodies are chimeric immunoglobulins, immunoglobulin chains or fragments thereof (such as Fv, Fab, Fab', F(ab') or other antigen-binding subsequences of antibodies) which contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies may comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., Nature, 321:522-525 (1986); Reichmann et al., Nature, 332:323-329 (1988); and Presta, Curr. Op. Struct. Biol., 2:593-596 (1992). The humanized antibody includes a Primatized antibody wherein the antigen-binding region of the antibody is derived from an antibody produced by immunizing macaque monkeys with the antigen of interest.

Polymerase chain reaction (PCR) is a technique for enzymatically replicating DNA without using a living organism. The technique allows a small amount of DNA to be amplified exponentially using the temperature-mediated enzyme DNA polymerase. Reverse transcription-PCR (RT-PCR) is a technique for amplifying a defined piece of a ribonucleic acid (RNA) molecule. The RNA strand is first reverse transcribed into its complementary DNA (cDNA), followed by amplification using PCR.

DNA sequencing is the process of determining the nucleotide order of a given DNA fragment, called the sequence.

An expression vector is a circular DNA molecule that is used to introduce and express a specific DNA sequence into a target cell. Construction of expression plasmids is the process of cloning a specific DNA fragment, containing e.g. the ORF of a desired gene, into an expression vector.

Transfection is the introduction of foreign DNA into cells. Transfection involves opening transient holes in cells to allow the entry of expression plasmid. Once the expression plasmid is inside the cell, the protein that is encoded by this DNA sequence is produced by the cellular transcription and translation machinery. The plasmid DNA is not incorporated into the cell's genome, but is only transiently expressed.

Cell culture is the process by which cell lines or primary cells isolated from tissues are grown under controlled conditions. Cells are grown and maintained in a culture medium at an appropriate temperature and gas mixture in a cell incubator.

A western blot analysis is a method to detect protein in a given sample. It uses gel electrophoresis to separate denatured proteins by mass. After separation, the proteins are transferred onto a membrane, where they are detected using antibodies recognizing the protein.

Enzyme-Linked ImmunoSorbent Assay (ELISA) analysis is a technique to detect the presence of an antibody or an antigen in a sample using two antibodies. One antibody is specific to the antigen and the other reacts to antigen-antibody complexes, and is coupled to an enzyme. This second antibody can cause a chromogenic, radioactive or fluorogenic substrate to produce a signal.

In immunofluorescence analysis, a primary antibody is used to detect a specific protein epitope. Detection of this primary antibody is accomplished by secondary antibody that is labeled using an enzyme, radiolabel or fluorophore. Immunofluorescently labeled cell and tissue samples are analysed using a fluorescence or confocal microscopy.

The present invention is based on the discovery of the new splice variant of the GDNF gene, pre-(γ)pro-GDNF. The examples described herein demonstrate that the pre-(γ)pro-GDNF mRNA is expressed in human brain (FIG. 4), and that the secretion of the protein encoded by this splice variant is strictly under biological and physiological regulation, indicating that (γ)pro-GDNF protein is much more potent therapeutic molecule for treatment of Parkinson's disease, ALS, addiction, alcoholism, ischemia, epilepsy and depression than the (α)pro-GDNF. In addition, the expression of pre-(γ)pro-GDNF mRNA was also characterized in lung and uterus (data not shown).

Treatment

The pre-(β)pro-GDNF and pre-(γ)pro-GDNF find in vivo gene therapeutic use for administration to mammals, particularly humans, in the treatment of diseases or disorders related to GDNF activity or benefited by GDNF-responsiveness. Particularly preferred are neurological disorders, preferably central nervous system disorders, Parkinson's disease, Alzheimer's disease, ALS, spinal cord injury, addiction and alcoholism.

Genetic manipulations to achieve modulation of protein expression or activity are specifically contemplated. Any suitable vector may be used to introduce a transgene of interest into an animal. Exemplary vectors that have been described in the literature include replication-deficient retroviral vectors, including but not limited to lentivirus vectors (Kim et al., J. Virol., 72: 811-816 (1998); Kingsman & Johnson, Scrip Magazine, October, 1998, pp. 43-46.); adenoviral (see, for example, U.S. Pat. No. 5,824,544; U.S. Pat. No. 5,707,618; U.S. Pat. No. 5,792,453; U.S. Pat. No. 5,693,509; U.S. Pat. No. 5,670,488; U.S. Pat. No. 5,585,362; Quantin et al., Proc. Natl. Acad. Sci. USA, 89: 2581-2584 (1992); Stratford-Perricadet et al., J. Clin. Invest., 90: 626-630 (1992); and Rosenfeld et al., Cell, 68: 143-155 (1992)), retroviral (see, for example, U.S. Pat. No. 5,888,502; U.S. Pat. No. 5,830,725; U.S. Pat. No. 5,770,414; U.S. Pat. No. 5,686,278; U.S. Pat. No. 4,861,719), adeno-associated viral (see, for example, U.S. Pat. No. 5,474,935; U.S. Pat. No. 5,139,941; U.S. Pat. No. 5,622,856; U.S. Pat. No. 5,658,776; U.S. Pat. No. 5,773,289; U.S. Pat. No. 5,789,390; U.S. Pat. No. 5,834,441; U.S. Pat. No. 5,863,541; U.S. Pat. No. 5,851,521; U.S. Pat. No. 5,252,479; Gnatenko et al., J. Investig. Med., 45: 87-98 (1997), an adenoviral-adeno-associated viral hybrid (see, for example, U.S. Pat. No. 5,856,152) or a vaccinia viral or a herpesviral (see, for example, U.S. Pat. No. 5,879,934; U.S. Pat. No. 5,849,571; U.S. Pat. No. 5,830,727; U.S. Pat. No. 5,661,033; U.S. Pat. No. 5,328,688); Lipofectin-mediated gene transfer (BRL); liposomal vectors [See, e.g., U.S. Pat. No. 5,631,237 (Liposomes comprising Sendai virus proteins)]; as well as viral vectors in which the gene expression can be regulated in vivo; and combinations thereof. All of the foregoing documents are incorporated herein by reference in their entirety. Replication-deficient adenoviral vectors, adeno-associated viral vectors and lentiviruses constitute preferred embodiments.

Semipermeable, implantable membrane devices are useful as means for delivering drugs in certain circumstances. For example, cells that secrete soluble (β)pro-GDNF or (γ)pro-GDNF or chimeras can be encapsulated, and such devices can be implanted into a patient. For example, into the brain of patients suffering from Parkinson's Disease. See, U.S. Pat. No. 4,892,538 of Aebischer et al.; U.S. Pat. No. 5,011,472 of Aebischer et al.; U.S. Pat. No. 5,106,627 of Aebischer et al.; PCT Application WO 91/10425; PCT Application WO 91/10470; Winn et al., Exper. Neurology, 113:322-329 (1991); Aebischer et al., Exper. Neurology, 111:269-275 (1991); and Tresco et al., ASAIO, 38:17-23 (1992).

Accordingly, also included is a method for preventing or treating damage to a nerve or damage to other (β)pro-GDNF or (γ)pro-GDNF responsive cells, which comprises implanting cells that secrete (β)pro-GDNF or (γ)pro-GDNF into the body of patients in need thereof. Finally, the present invention includes a device for preventing or treating nerve damage or damage to other cells as taught herein by implantation into a patient comprising a semipermeable membrane, and a cell that secretes (β)pro-GDNF or (γ)pro-GDNF encapsulated within said membrane and said membrane being permeable to (β)pro-GDNF or (γ)pro-GDNF and impermeable to factors from the patient detrimental to the cells. The patient's own cells, transformed to produce (β)pro-GDNF or (γ)pro-GDNF ex vivo, could be implanted directly into the patient, optionally without such encapsulation. The methodology for the membrane encapsulation of living cells is familiar to those of ordinary skill in the art, and the preparation of the encapsulated cells and their implantation in patients may be accomplished without undue experimentation.

The present invention includes, therefore, a method for preventing or treating nerve damage by implanting cells, into the body of a patient in need thereof; cells either selected for their natural ability to generate or engineered to secrete (β)pro-GDNF or (γ)pro-GDNF. Preferably, the secreted (β)pro-GDNF or (γ)pro-GDNF being soluble, human (β)pro-GDNF or (γ)pro-GDNF when the patient is human. The implants are preferably non-immunogenic and/or prevent immunogenic implanted cells from being recognized by the immune system. For CNS delivery, a preferred location for the implant is the striatum.

In embodiments employing a viral vector, preferred polynucleotides include a suitable promoter and polyadenylation sequence to promote expression in the target tissue of interest. For the present invention, suitable promoters/enhancers for mammalian cell expression include, e.g., cytomegalovirus promoter/enhancer (Lehner et al., J. Clin. Microbiol., 29:2494-2502 (1991); Boshart et al., Cell, 41:521-530 (1985)); Rous sarcoma virus promoter (Davis et al., Hum. Gene Ther., 4:151 (1993)); simian virus 40 promoter, long terminal repeat (LTR) of retroviruses, keratin 14 promoter, and a myosin heavy chain promoter.

In gene therapy applications, genes are introduced into cells in order to achieve in vivo synthesis of a therapeutically effective genetic product, for example for replacement of a defective gene. "Gene therapy" includes both conventional gene therapy, where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., Proc. Natl. Acad.

Sci. USA, 83:4143-4146 (1986)). The oligonucleotides can be modified to enhance their uptake, e.g., by substituting their negatively charged phosphor-diester groups by uncharged groups.

There are a variety of techniques available for introducing nucleic acids into viable cells. The techniques vary depending upon whether the nucleic acid is transferred into cultured cells in vitro, ex vivo, or in vivo in the cells of the intended host. Techniques suitable for the transfer of nucleic acid into mammalian cells in vitro include the use of liposomes (Nicolau and Sene, Biochim. Biophys. Acta, 721:185-190 (1982); Fraley, et al., Proc. Natl. Acad. Sci. USA, 76:3348-3352 (1979); Feigner, Sci. Am., 276(6):102-106 (1997); Feigner, Hum. Gene Ther., 7(15):1791-1793, (1996)), electroporation (Tur-Kaspa, et al., Mol. Cell Biol., 6:716-718 (1986); Potter, et al., Proc. Nat. Acad. Sci. USA, 81:7161-7165 (1984)), direct microinjection (Harland and Weintraub, J. Cell Biol., 101:1094-1099 (1985)), cell fusion, DEAE-dextran (Gopal, Mol. Cell Biol., 5:1188-1190 (1985), the calcium phosphate precipitation method (Graham and Van Der Eb, Virology, 52:456-467 (1973); Chen and Okayama, Mol. Cell Biol., 7:2745-2752, (1987); Rippe, et al., Mol. Cell Biol., 10:689-695 (1990), cell sonication (Fechheimer, et al., Proc. Natl. Acad. Sci. USA, 84:8463-8467 (1987)), gene bombardment using high velocity microprojectiles (Yang, et al., Proc. Natl. Acad. Sci. USA, 87:9568-9572 (1990). The currently preferred in vivo gene transfer techniques include transfection with viral (typically retroviral) vectors and viral coat protein-liposome mediated transfection (Dzau et al., Trends in Biotechnology, 11: 205-210 (1993)). In some situations it is desirable to provide the nucleic acid source with an agent that targets the target cells, such as an antibody specific for a cell surface membrane protein of the target cell, a ligand for a receptor on the target cell. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, and proteins that target intracellular localization and enhance intracellular half-life. The technique of receptor-mediated endocytosis is described, for example, by Wu et al., J. Biol. Chem., 262:4429-4432 (1987); and Wagner et al., Proc. Natl. Acad. Sci. USA, 87:3410-3414 (1990). For review of the currently known gene marking and gene therapy protocols see Anderson et al., Science, 256: 808-813 (1992).

In a particular embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, "In Liver Diseases, Targeted Diagnosis And Therapy Using Specific Receptors And Ligands," Wu, G., Wu, C., ed., New York: Marcel Dekker, pp. 87-104 (1991)). The addition of DNA to cationic liposomes causes a topological transition from liposomes to optically birefringent liquid-crystalline condensed globules (Radler, et al., Science, 275: 810-814 (1997)). These DNA-lipid complexes are potential non-viral vectors for use in gene therapy and delivery.

Also contemplated in the present invention are various commercial approaches involving "lipofection" technology.

In certain embodiments of the invention, the liposome may be complexed with a hemagglutinating virus (HVJ). This has been shown to facilitate fusion with the cell membrane and promote cell entry of liposome-encapsulated DNA (Kaneda, et al., Science, 243:375-378 (1989)). In other embodiments, the liposome may be complexed or employed in conjunction with nuclear nonhistone chromosomal proteins (HMG-1) (Kato, et al., J. Biol. Chem., 266:3361-3364 (1991)). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention.

Other vector delivery systems that can be employed to deliver a nucleic acid encoding a therapeutic gene into cells include receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, Adv. Drug Del. Rev., 12:159-167 (1993)).

In another embodiment of the invention, the expression construct may simply consist of naked recombinant DNA or plasmids. Transfer of the construct may be performed by any of the methods mentioned above that physically or chemically permeabilize the cell membrane. This is applicable particularly for transfer in vitro, however, it may be applied for in vivo use as well. Dubensky, et al., Proc. Nat. Acad. Sci. USA, 81:7529-7533 (1984) successfully injected polyomavirus DNA in the form of $CaPO_4$ precipitates into liver and spleen of adult and newborn mice demonstrating active viral replication and acute infection. Benvenisty and Neshif, Proc. Nat. Acad. Sci. USA, 83:9551-9555 (1986) also demonstrated that direct intraperitoneal injection of $CaPO_4$ precipitated plasmids results in the expression of the transfected genes.

Another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein, et al., Nature, 327:70-73 (1987)). Several devices for accelerating small particles have been developed. One such device relies on a high voltage discharge to generate an electrical current, which in turn provides the motive force (Yang, et al., Proc. Natl. Acad. Sci USA, 87:9568-9572 (1990)). The microprojectiles used have consisted of biologically inert substances such as tungsten or gold beads.

Those of skill in the art are aware of how to apply gene delivery to in vivo and ex vivo situations. For viral vectors, one generally will prepare a viral vector stock. Depending on the type of virus and the titer attainable, one will deliver $1\times10^4$, $1\times10^5$, $1\times10^6$, $1\times10^7$, $1\times10^8$, $1\times10^9$, $1\times10^{10}$, $1\times10^{11}$ or $1\times10^{12}$ infectious particles to the patient. Similar figures may be extrapolated for liposomal or other non-viral formulations by comparing relative uptake efficiencies. Formulation as a pharmaceutically acceptable composition is discussed below.

Various routes are contemplated for various cell types. For practically any cell, tissue or organ type, systemic delivery is contemplated. In other embodiments, a variety of direct, local and regional approaches may be taken. For example, the cell, tissue or organ may be directly injected with the expression vector or protein.

In a different embodiment, ex vivo gene therapy is contemplated. In an ex vivo embodiment, cells from the patient are removed and maintained outside the body for at least some period of time. During this period, a therapy is delivered, after which the cells are reintroduced into the patient.

The strategy for transferring genes into target cells in vivo includes the following basic steps: (1) selection of an appropriate transgene or transgenes whose expression is correlated with CNS disease or dysfunction; (2) selection and development of suitable and efficient vectors for gene transfer; (3) demonstration that in vivo transduction of target cells and transgene expression occurs stably and efficiently; (4) demonstration that the in vivo gene therapy procedure causes no serious deleterious effects; and (5) demonstration of a desired phenotypic effect in the host animal.

Although other vectors may be used, preferred vectors for use in the methods of the present invention are viral and non-viral vectors. The vector selected should meet the following criteria: 1) the vector must be able to infect targeted cells and thus viral vectors having an appropriate host range must be selected; 2) the transferred gene should be capable of persisting and being expressed in a cell for an extended period of time (without causing cell death) for stable maintenance and expression in the cell; and 3) the vector should do little, if any, damage to target cells.

Because adult mammalian brain cells are non-dividing, the recombinant expression vector chosen must be able to transfect and be expressed in non-dividing cells. At present, vectors known to have this capability include DNA viruses such as adenoviruses, adeno-associated virus (AAV), and certain RNA viruses such as HIV-based lentiviruses, feline immunodeficiency virus (FIV) and equine immunodeficiency virus (EIV). Other vectors with this capability include herpes simplex virus (HSV). However, some of these viruses (e.g., AAV and HSV) can produce toxicity and/or immunogenicity. Recently, an HIV-based lentiviral vector system has been developed which, like other retroviruses, can insert a transgene into the nucleus of host cells (enhancing the stability of expression) but, unlike other retroviruses, can make the insertion into the nucleus of non-dividing cells. Lentiviral vectors have been shown to stably transfect brain cells after direct injection, and stably express a foreign transgene without detectable pathogenesis from viral proteins (see, Naldini, et al., Science, 272:263-267 (1996), the disclosure of which is incorporated herein by reference). Following the teachings of the researchers who first constructed the HIV-1 retroviral vector, those of ordinary skill in the art will be able to construct lentiviral vectors suitable for use in the methods of the invention (for more general reference concerning retrovirus construction, see, e.g., Kriegler, Gene Transfer and Expression, A Laboratory Manual, W. Freeman Co. (NY 1990) and Murray, E J, ed., Methods in Molecular Biology, Vol. 7, Humana Press (NJ 1991)).

The use of recombinant AAV vectors is efficient; their infection is relatively long-lived and is generally non-toxic, unless a toxic transgene is recombined therein. AAV is a helper-dependent parvovirus consisting of a single strand 4.7 kb DNA genome surrounded by a simple, non-enveloped icosahedral protein coat. About 85% of the adult human population is seropositive for AAV. Nonetheless, no pathology has been associated with AAV infection. AAV is dependent on Adenovirus or herpes virus as a helper virus to establish productive infection by AAV. In the absence of helper virus, the AAV genome also amplifies in response to toxic challenge (UV irradiation, hydroxyurea exposure). If there is no toxic challenge or helper virus, wild-type AAV integrates into human chromosome 19 site-specifically. This is driven by the AAV Rep proteins that mediate the formation of an AAV-chromosome complex at the chromosomal integration site. Most of the viral genome (96%) may be removed, leaving only the two 145 base pair (bp) inverted terminal repeats (ITRs) for packaging and integration of the viral genome. Techniques for efficient propagation of recombinant AAV, rAAV, have been developed in the art: the use of mini-adenoviral genome plasmids, plasmids encoding AAV packaging functions and adenovirus helper functions in single plasmids. Moreover, methods of rAAV for isolation of highly purified rAAV are a relatively straightforward and rapid undertaking, as is titration of rAAV stocks. To trace rAAV-mediated transgene expression the green fluorescent protein (GFP), a well-characterized 238 amino acid fluorescent protein, is frequently used in a bicistronic arrangement in rAAV. Selective and specific expression of rAAV mediated gene transfer through different promoters has also been identified. We use a commercially available AAV Helper-free system (Stratagene) to construct our recombinant AAVs. Pre-(β)pro-GDNF and pre-(γ)pro-GDNF will be cloned into vectors/plasmids of the AAV system using conventional recombinant DNA techniques.

Viral Vectors Expressing pre-(β)pro-GDNF and pre-(γ)pro-GDNF-ATG

Construction of vectors for recombinant expression of nervous system growth factors for use in the invention may be accomplished using conventional techniques which do not require detailed explanation to one of ordinary skill in the art. Specifics for construction of AAV vector is set forth in here. For further review, those of ordinary skill may wish to consult Maniatis et al., in Molecular Cloning: A Laboratory Manual, Cold Spring Harbor Laboratory, (NY 1982).

Briefly, construction of recombinant expression vectors employs standard ligation techniques. For analysis to confirm correct sequences in vectors constructed, the ligation mixtures may be used to transform a host cell and successful transformants selected by antibiotic resistance, where appropriate. Vectors from the transformants are prepared, analyzed by restriction and/or sequenced by, for example, the method of Messing et al., (Nucleic Acids Res., 9:309 (1981)), the method of Maxam et al., (Methods in Enzymology, 65:499 (1980)), or other suitable methods which will be known to those skilled in the art. Size separation of cleaved fragments is performed using conventional gel electrophoresis as described, for example, by Maniatis et al., (Molecular Cloning, pp. 133-134 (1982)).

Expression of a cDNA (pre-(β)pro-GDNF and pre-(γ)pro-GDNF-ATG) is controlled at the transcription, translation or post-translation levels. Transcription initiation is an early and critical event in gene expression. This depends on the promoter and enhancer sequences and is influenced by specific cellular factors that interact with these sequences. The transcriptional unit of many prokaryotic genes consists of the promoter and in some cases enhancer or regulator elements (Banerji et al., Cell 27:299 (1981); Corden et al., Science, 209:1406 (1980); and Breathnach and Chambon, Ann. Rev. Biochem. 50:349 (1981)). For retroviruses, control elements involved in the replication of the retroviral genome reside in the long terminal repeat (LTR) (Weiss et al., eds., The molecular biology of tumor viruses: RNA tumor viruses, Cold Spring Harbor Laboratory, (NY 1982)). Moloney murine leukemia virus (MLV) and Rous sarcoma virus (RSV) LTRs contain promoter and enhancer sequences (Jolly et al., Nucleic Acids Res., 11:1855 (1983); Capecchi et al., In: Enhancer and eukaryotic gene expression, Gulzman and Shenk, eds., pp. 101-102, Cold Spring Harbor Laboratories (NY 1991)). Other potent promoters include those derived from cytomegalovirus (CMV) and other wild-type viral promoters.

Methods of making and using rAAV and delivery of rAAV to various cells in vivo are found in U.S. Pat. Nos. 5,720,720; 6,027,931; 6,071,889; as well as WO 99/61066; all of which are hereby incorporated by reference for this purpose. Different serotypes of AAV are available, and they show tissue tropism. Thus, the use of the accurate serotype depends on which tissue is to be transduced.

With regard to methods for the successful, localized, long-term and non-toxic transgene expression in the nervous system using adeno-associated virus (AAV) and selected promoters, reference is made to Klein et al., Experimental Neurology, 150:183-194 (1998), "Neuron-Specific Transduction in the Rat Septohippocampal or Nigrostriatal Pathway by Recombinant Adeno-associated Virus Vectors".

With respect to a method of gene therapy using recombinant AAV with significant persistence through stable expression of the neurotrophic factors NGF, GDNF, BDNF, and resultant neurochemically quantifiable therapeutic effects, reference is made to Klein et al., Neuroscience, 90:815-821 (1999), "Long-term Actions of Vector-derived Nerve Growth Factor or Brain-derived Neurotrophic Factor on Choline Acetyltransferase and Trk Receptor Levels in the Adult Rat Basal Forebrain."

A further important parameter is the dosage of pre-(β)pro-GDNF and pre-(γ)pro-GDNF to be delivered into the target tissue. For viral vectors, pre-(β)pro-GDNF and pre-(γ)pro-GDNF concentrations may be defined by the number of viral particles/ml of neurotrophic composition. Optimally, for delivery of pre-(β)pro-GDNF and pre-(γ)pro-GDNF using viral expression vectors, each unit dosage of pre-(γ)pro-GDNF will comprise 2.5 to 25 µl of pre-(γ)pro-GDNF composition, wherein the composition includes viral expression vector in pharmaceutically acceptable fluid and provides from $10^{10}$ to $10^{15}$ pre-(β)pro-GDNF or pre-(γ)pro-GDNF expressing viral particles per ml of pre-(β)pro-GDNF or pre-(γ)pro-GDNF composition. Such high titers are particularly useful for AAV. For lentivirus, the titer is normally lower, from $10^8$ to $10^{10}$ transducing units per ml (TU/ml).

EXPERIMENTAL

Example 1

Figure 3:
FIG. 3. Analysis of mouse GDNF mRNA expression in kidney tissues analysed by RT-PCR. Lane 1 embryonic day 13 (E13) kidney tissue; Lane 2 E15 kidney tissue; Lane 3 E17 kidney tissue; Lane 4 postnatal day 1 (P1) kidney tissue; Lane 5 P5 kidney tissue; Lane 6 P6 kidney tissue; Lane 7 empty lane; Lane 8 negative PCR control. The pre-(α)pro-GDNF, pre-(β)pro-GDNF and pre-(γ)pro-GDNF variants are marked with arrows. The pre-(α)pro-GDNF and pre-(β) pro-GDNF variants are detected in samples E13-P1. The pre-(γ)pro-GDNF variant is detected in samples E13, E15 and P1.
Figure 4:
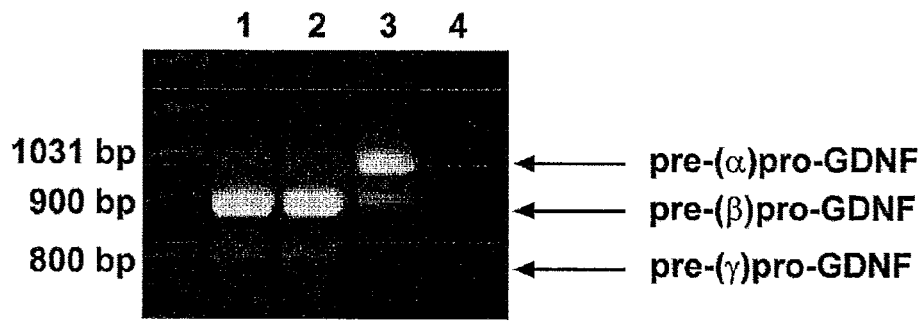
FIG. 4. Analysis of human GDNF mRNA expression in adult brain tissue analysed by RT-PCR. Lanes 1 and 2 human adult brain tissue; Lane 3 positive PCR control; Lane 4 negative PCR control. The pre-(α)pro-GDNF, pre-(β)pro-GDNF and pre-(γ)pro-GDNF variants are marked with arrows.

Cloning of GDNF Splice Variant cDNAs and Expression Analyses of GDNF Splice Variant mRNAs by RT-PCR We cloned pre-(α)pro-GDNF, pre-(β)pro-GDNF and pre-(γ)pro-GDNF cDNAs by RT-PCR from mouse (by using first pair primers 42 and 43 and nested primers 46 and 47) kidney and brain cells as well as from human (by using first pair primers 53 and 49 and nested primers 48 and 54) kidney, uterus and brain cells (FIGS. 3 and 4). Mouse total RNA was isolated using RNA extraction kit (Ambion), human RNAs were obtained from Clontech. First strand cDNAs were synthesized with reverse transcriptase (Superscript$^{II}$, Invitrogen) using oligo(dT) (Promega) primed total RNA (5 µg) from different tissues as a template.

The primers used in cloning of mouse pre-(α)pro-GDNF, pre-(β)pro-GDNF and pre-(γ)pro-GDNF and human pre-(α)pro-GDNF, pre-(β)pro-GDNF and pre-(γ)pro-GDNF were:

```
The first primer at the 5'orientation of the
mouse Gdnf gene (primer 42)
5'-GCTCCTGCCCGAGGTC-3'        (SEQ ID NO: 7)

The first primer at the 3'orientation of the
mouse Gdnf gene (primer 43)
5'-CCTTTCTTCGCACTGTAGCAG-3'   (SEQ ID NO: 8)

The nested primer at the 5'orientation of the
mouse Gdnf gene (primer 46)
5'-GTCCGGATGGGTCTCCTGG-3'     (SEQ ID NO: 9)

The nested primer at the 3'orientation of the
mouse Gdnf gene (Primer 47)
5'-CACAGCAGTCTCTGGAGCCG-3'    (SEQ ID NO: 10)

The first primer at the 5'orientation of the
human GDNF gene (primer 53)
5'-GACCTGTTGGGCGGGGCTC-3'     (SEQ ID NO: 11)

The first primer at the 3'orientation of the
human GDNF gene (primer 49)
5'-CCTGGGAACCTTGGTCCCTTTC-3'  (SEQ ID NO: 12)

The nested primer at the 5'orientation of the
human GDNF gene (primer 48)
5'-GCTCCAGCCATCAGCCCGG-3'     (SEQ ID NO: 13)

The nested primer at the 3'orientation of the
human GDNF gene (primer 54)
5'-CACAGCAGTCTCTGGAGCCGG-3'   (SEQ ID NO: 14)
```

PCR reactions were performed in the volume of 500 or 250 containing 2/5 or 1/5 of RT reaction as a template and 3.75 or 1.86 units of enzyme mix containing thermostable Taq DNA polymerase and Tgo DNA polymerase (Roche), respectively, and the Expand Long Distance Template PCR System kit (Roche) according to manufacturer's instructions. The first PCR reaction was followed by nested PCR reaction, where 1-2 µl of the first PCR reaction was used as a template. In both first and nested PCR reactions, DNA was amplified using the following conditions: 94° C. (2 minutes); 10 cycles of 94° C. (10 s), 62° C. (30 s), 68° C. (1 minute); 25 cycles of 94° C. (15 s), 62° C. (30 s), 68° C. (1 minute 20 s); 1 cycle of 68° C. (7 minutes), 4° C. (5 minutes). The amplified RT-PCR products were resolved on 2% agarose gel, followed by either direct sequencing of PCR fragments or cloning of the fragments into pCR2.1 vector (Invitrogen) followed by verification by sequencing. The DNA fragments were sequenced with an ABI 3100 Capillary Sequencer using Dye Terminator (v3.1) kit (Applied Biosystems) as recommended by the manufacturer.

The primers used for sequencing of gel extracted human PCR fragments were at the 5' orientation of the GDNF gene 5'GCTCCAGCCATCAGCCCGG-3' (SEQ ID NO:15) and at the 3' orientation of the GDNF gene 5'-CACAGCAGTCTCTGGAGCCGG-3' (SEQ ID NO:16). The primers used for sequencing of mouse PCR fragments were at the 5' orientation of the GDNF gene 5'-GTCCGGATGGGTCTCCTGG-3' (SEQ ID NO:9) and at the 3' orientation of the GDNF gene 5'-CACAGCAGTCTCTGGAGCCG-3' (SEQ ID NO:10).

For expression analysis of respective mRNAs, mouse and human pre-(α)pro-GDNF, pre-(β)pro-GDNF and pre-(γ)pro-GDNF were cleaved from pCR2.1 vector with restriction enzymes XhoI and HindIII and ligated into an pEGFP-N1 expression vector cleaved with the same restriction enzymes. The primers used for sequencing of the inserted PCR fragment were at the 5' orientation 5'-CAACGGGACTTTCCAAAATG-3' (SEQ ID NO:37) and at the 3' orientation 3'-GGACACGCTGAACTTGTGG-5' (SEQ ID NO:38).

For further expression analysis the human pre-(α)pro-GDNF and pre-(β)pro-GDNF were cloned into pAAV-MCS and pAAV-IRES-hrGFP expression vectors (Stratagene) resulting in pAAV-MCS-pre-(α)pro-GDNF, pAAV-MCS-pre-(β)pro-GDNF, pAAV-IRES-hrGFP-pre-(α)pro-GDNF and pAAV-IRES-hrGFP-pre-(β)pro-GDNF constructs. The primers used in cloning were:

```
The primer at the 5'orientation (89)
                                   (SEQ ID NO: 39)
5'-CAACAAGGATCCATGAAGTTATGGGATGTCGTGG-3'

The primer at the 3'orientation (90)
                                   (SEQ ID NO: 40)
3'-CCACCACTCGAGTCAGATACATCCACACCTTTTAG-5'
```

For the expression analysis the translation start codon CTG of the human pre-(γ)pro-GDNF was replaced with conventional ATG translation start codon and the cDNA was cloned into pAAV-MCS expression vector (Stratagene) resulting in pAAV-MCS-pre-(γ)pro-GDNF-ATG construct. The primers used in cloning were:

```
The primer at the 5'orientation (91)
                                   (SEQ ID NO: 17)
5'-CAACAAGGATCCATGGGACTTGGGGCACCTGGAGTTAATG-3'

The primer at the 3'orientation (92)
                                   (SEQ ID NO: 18)
5'-CCACCACTCGAGTCAGATACATCCACACCTTTTAGCGG-3'
```

Primers 89 and 90 or 91 and 92 were used in PCR with Dynazyme DNA polymerase (Finnzymes) and Dynazyme 10× buffer. Total volume of PCR reaction was 50 μA containing 40 ng of human pre-(α)pro-GDNF or pre-(β)pro-GDNF in pEGFP-N1 vector as a template. DNA was amplified using the following conditions: 95° C. (5 minutes); 25 cycles of 95° C. (45 s), 56° C. (45 s), 72° C. (1 minute); 1 cycle of 72° C. (7 minutes), 4° C. (7 minutes). The amplified PCR product was cleaved with restriction enzymes BamHI and XhoI and ligated into the pAAV-MCS vector (Stratagene) cleaved with the same restriction enzymes followed by verification by sequencing.

The primers used for sequencing of the inserted PCR fragment were at the 5'orientation 5'-ATTCTGAGTC-CAAGCTAGGC-3' (SEQ ID NO:41) and at the 3'orientation 3'-TAGAAGGACACCTAGTCAGA-5' (SEQ ID NO:42).

Example 2

Cell Culture

CHO, HEK-293, PC-6.3 and AtT-20 cell lines were grown in Dulbecco's modified Eagle's medium (DMEM) containing antibiotics together with 10% FCS (Gibco) (CHO and HEK-293 cells), 10% HS (Gibco) and 5% FCS (PC-6.3 cells), 10% FCS, 4.5 g/l glucose and 1.5 g/l sodium carbonate (AtT-20 cells). BHK-21 cell line was grown in Minimum essential medium (MEM) containing antibiotics, 7.5% FCS, 0.04% tryptose phosphate broth (Difco) and 1% glutamate (Gibco). Cells were transfected with pEGFP-N1 (Invitrogen) expression vector containing mouse pre-(α)pro-GDNF, pre-(β)pro-GDNF or pre-(γ)pro-GDNF or human pre-(α) pro-GDNF, pre-(β)pro-GDNF or pre-(γ)pro-GDNF cDNA. Alternatively, cells were transfected with pAAV-MCS or pAAV-IRES-hrGFP vector containing human pre-(α)pro-GDNF, pre-(β)pro-GDNF or pre-(γ)pro-GDNF-ATG cDNA by using Lipofectamine 2000 (Invitrogen) transfection protocol. In Western blot analysis, transfected cells were grown for 48 h in OptiMEM (Sigma) medium followed by collection of the media and preparation of protein extracts from cells. Secreted proteins (medium) were concentrated using Amicon Ultra-4 Centrifugal Filter Units (Millipore) or GDNF was immunoprecipitated using mouse anti-GDNF antibody. Protein extracts were resolved on 15% SDS-polyacrylamide gel and analyzed by Western blot using D20 antibody (Santa Cruz). In immunofluorescence analysis, transfected cells were grown 24 h in normal growth medium followed by fixation and permeabilization. Cells were stained with primary and secondary antibodies and images were acquired through a charge-coupled device camera (DP70; Olympus) on a microscope (AX70 Provis; Olympus).

Results

Figure 5:
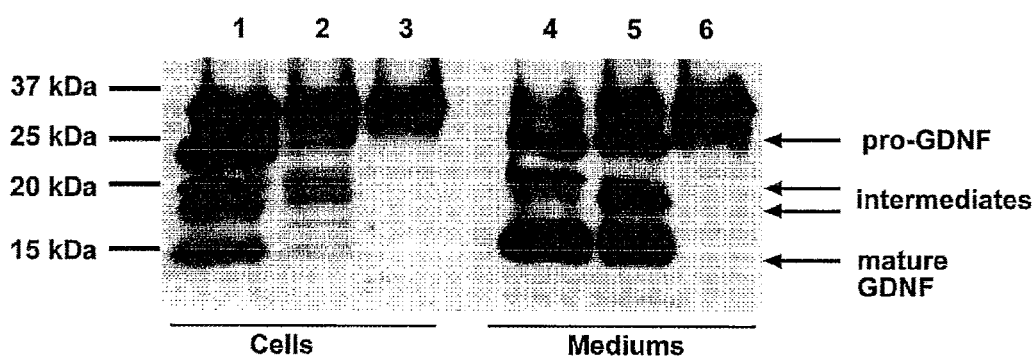
FIG. 5. Analysis of mouse (α)pro-GDNF and (β)pro-GDNF proteins as expressed in CHO cells. Expression constructs containing mouse pre-(α)pro-GDNF or pre-(β)pro-GDNF were generated by cloning of cDNAs with stop-codons into pEGFP-N1 expression vector (Invitrogen). CHO cells grown in DMEM with 10% FCS and antibiotics were plated on 6-well plates and each well was transfected with 4 µg of plasmid when grown up to approximately 80% confluence. The media were replaced with OptiMEM media 4 hrs after transfection. The cells and media (supernatant) were collected 48 hrs post-transfection and GDNF was immunoprecipitated using mouse anti-GDNF antibody (3.3 µg/sample), separated using 15% denaturing SDS-PAGE gel followed by blotting into nylon membrane and blocking with 5% milk in TBS-Tween (0.1%). GDNF was detected with rabbit anti-GDNF antibody (Santa Cruz, 1:500 dilution) and HRP-conjugated donkey anti-rabbit immunoglobulin secondary antibody (1:2000 dilution) by using ECL method. Lane 1 mouse pre-(α)pro-GDNF transfected cells, cell lysate; Lane 2 mouse pre-(β)pro-GDNF transfected cells, cell lysate; Lane 3 Non-transfected cells (negative control), cell lysate; Lane 4 mouse pre-(α)pro-GDNF transfected cells, medium; Lane 5 mouse pre-(β)pro-GDNF transfected cells, medium; Lane 6 non-transfected cells (negative control), medium.
Figure 6:
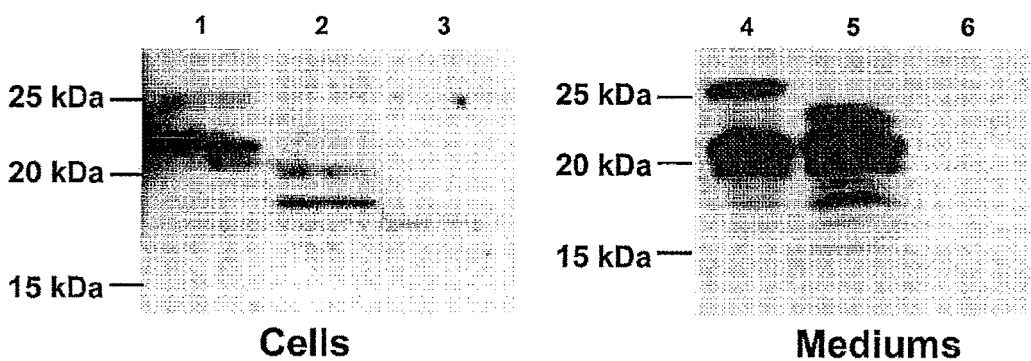
FIG. 6. Analysis of human (α)pro-GDNF and (β)pro-GDNF proteins as expressed in CHO cells. Expression constructs containing human pre-(α)pro-GDNF or pre-(β)pro-GDNF were generated by cloning of cDNAs with stop-codons into pEGFP-N1 expression vector (Invitrogen). CHO cells grown in DMEM with 10% FCS and antibiotics were plated on 6-well plates and each well was transfected with 4 µg of plasmid when grown up to approximately 80% confluence. The media were replaced with OptiMEM medium 4 hrs after transfection. The cells and media (supernatant) were collected 48 hrs post-transfection and separated using 15% denaturing SDS-PAGE gel followed by blotting into nylon membrane and blocking with 5% milk in TBS-Tween (0.1%). GDNF was detected with rabbit anti-GDNF antibody (Santa Cruz, 1:500 dilution) and HRP-conjugated donkey anti-rabbit immunoglobulin secondary antibody (1:2000 dilution) by using ECL method. Lane 1 human pre-(α)pro-GDNF transfected cells, cell lysate; Lane 2 human pre-(β)pro-GDNF transfected cells, cell lysate; Lane 3 non-transfected cells (negative control), cell lysate; Lane 4 human pre-(α)pro-GDNF transfected cells, medium; Lane 5 human pre-(β)pro-GDNF transfected cells, medium; Lane 6 non-transfected cells (negative control), medium.
Figure 7:
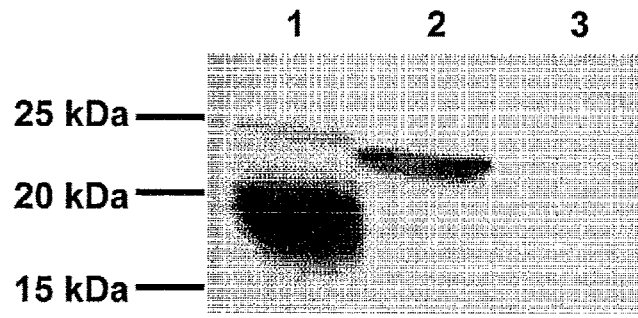
FIG. 7. Analysis of mouse (γ)pro-GDNF protein as expressed in BHK cells. Expression constructs containing mouse pre-(β)pro-GDNF or pre-(γ)pro-GDNF were generated by cloning of cDNAs with stop-codons into pEGFP-N1 expression vector (Invitrogen). BHK cells grown in DMEM with 10% FCS and antibiotics were plated on 6 well plates and each well was transfected with 4 µg of plasmid when grown up to approximately 80% confluence. The media were replaced with OptiMEM medium 4 hrs after transfection. The media (supernatant) were collected 48 hrs post-transfection and separated using 15% denaturing SDS-PAGE gel followed by blotting into nylon membrane and blocking with 5% milk in TBS-Tween (0.1%). GDNF was detected with rabbit anti-GDNF antibody (Santa Cruz, 1:500 dilution) and HRP-conjugated donkey anti-rabbit immunoglobulin secondary antibody (1:2000 dilution) by using ECL method. Lane 1 mouse pre-(β)pro-GDNF transfected cells, medium; Lane 2 mouse pre-(γ)pro-GDNF transfected cells, medium; Lane 3 non-transfected cells (negative control), medium.
Figure 8A:
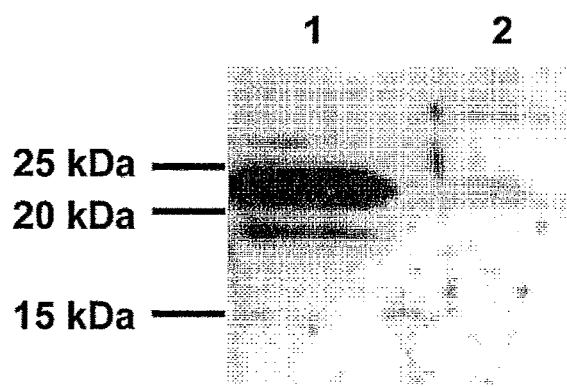
FIGS. 8A and 8B. Analysis of human (γ)pro-GDNF protein as expressed in BHK and COS-7 cells. Expression constructs containing human pre-(γ)pro-GDNF were generated by cloning of pre-(γ)pro-GDNF cDNAs with stop-codons, containing either ATG or CTG as a protein coding initiation codon, into pAAV-MCS (Stratagene) or pEGFP-N1 expression vectors (Invitrogen). BHK cells grown in DMEM with 10% FCS and antibiotics were plated on 6 well plates and each well was transfected with 4 µg of plasmid when grown up to approximately 80% confluence. The media were replaced with OptiMEM media 4 hrs after transfection. The media (supernatant) were collected 48 hrs postransfection and separated using 15% denaturing SDS-PAGE gel followed by blotting into nylon membrane and blocking with 5% milk in TBS-Tween (0.1%). GDNF was detected with rabbit anti-GDNF antibody (Santa Cruz, 1:500 dilution) and HRP-conjugated donkey anti-rabbit immunoglobulin secondary antibody (1:2000 dilution) by using ECL method.
Figure 8B:
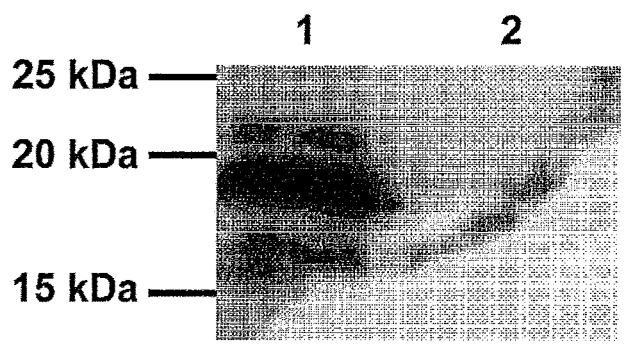

The results show that both human and mouse (α)pro-GDNF and (β)pro-GDNF and their mature GDNFs are secreted from CHO cell line (FIGS. 5 and 6). In addition they are secreted from HEK-293, PC-6.3 and AtT-20 cell lines. Mouse (γ)pro-GDNF and its mature GDNF are secreted from BHK-21 (FIG. 7), CHO and PC-6.3 cell lines and human (γ)pro-GDNF-ATG, where CTG translation start codon was replaced with ATG, and its mature GDNF are secreted from BHK-21 and COS-7 cell lines (FIG. 8).

Example 3

Secretion of Human pre-(α)pro-GDNF and pre-(β)pro-GDNF from Differentiated PC-6.3 Cells and Hippocampal Primary Cells Differentiation and Stimulation of PC-6.3 Cells After transfection, PC-6.3 cells were grown in differentiation medium containing Dulbecco's modified Eagle's medium (DMEM), 5% HS (Gibco), 2.5% FCS and 50 ng/ml NGF. After 72 h the medium was removed and replaced with serum-free DMEM with or without 50 mM KC1. Expression constructs used in transfections were human and mouse pre-(α)pro-GDNF and pre-(β)pro-GDNF in pEGFP. In ELISA analysis, pEGFP-N1 expression vector (Invitrogen) containing rat pre-pro-BDNF without a stop codon (a gift from Dr. Volkmar Lessman, University of Johannes-Gutenberg, Mainz, Germany) was used as a positive control for activity-dependent secretion (Haubensak et al., J. Cell Sci., 111:1483-93 (1998)). This construct was cloned similarly than other constructs used. In Western blot analysis, the media (supernatant) were collected after 5 h and concentrated using Amicon Ultra-4 Centrifugal Filter Units (Millipore). Protein extracts were resolved on 15% SDS-polyacrylamide gel and analyzed by Western blot using D20 antibody recognizing GDNF (Santa Cruz). In ELISA analysis the media were collected after 2 h and analysed using GDNF $E_{max}$ ImmunoAssay System (Promega) or BDNF $E_{max}$ ImmunoAssay System (Promega).

Immunofluorescence Analysis of Transfected, Differentiated PC-6.3 Cells

Expression constructs containing human pre-(α)pro-GDNF or pre-(β)pro-GDNF were generated by cloning of cDNAs with stop-codons into pEGFP-N1 expression vector (Invitrogen). PC-6.3 cells were differentiated in differentiation medium containing Dulbecco's modified Eagle's medium (DMEM), 5% HS (Gibco), 2.5% FCS and 50 ng/ml NGF for 3 days before transfection. Expression constructs used in transfections were human and mouse pre-(α)pro-GDNF and pre-(β)pro-GDNF in pEGFP. 24 h after transfections, cells were either fixed with 4% PFA or first stimulated 2 h with 50 mM KCl and 50 µg/ml cycloheximide, which stops the protein synthesis, and then fixed with 4% PFA. All cells were blocked with 0.5% BSA (Sigma) and permeabilized with 0.1% Triton X-100 (Sigma). Cells were incubated with primary antibodies polyclonal anti-GDNF (GeneWay Biotech Inc.; 1:750 dilution) and monoclonal anti-GM130 for mature Golgi (Abeam; 1:100 dilution) in 0.5% BSA in RT for 1 hr, washed and then repeated with secondary antibodies Cy2 conjugated donkey anti-mouse IgG (Jackson ImmunoResearch laboratories) and Cy3-conjugated donkey anti-rabbit IgG (Jackson ImmunoResearch laboratories). Finally, coverslips were mounted with Immumount (Thermo electron corporation). Images were acquired through a charge-coupled device camera (DP70; Olympus) on a microscope (AX70 Provis; Olympus).

Hippocampal Primary Neuronal Cultures, Transfections and Depolarization of the Cells For hippocampal neuron preparations, hippocampi from E18 rats were dissected. Tissue was digested with 0.25% trypsin in HBSS for 10-15 min at 37° C. DNaseI (1 mg/ml) was added, and sample was triturated with siliconized glass pipette. Cells were washed three times with HBBS containing 10 mM glucose (Sigma). In suspension, cells were transfected with pEGFP-N1 (Invitrogen) expression vector containing human or mouse pre-(α)pro-GDNF or pre-(β) pro-GDNF cDNA by using Rat Neuron Nucleofector Kit (Amaxa biosystems) as recommended by the manufacturer. The cells were plated on poly-D-lysine hydrobromide (Sigma) coated culture dishes and the cultures were grown in Neurobasal medium (Gibco Invitrogen) supplemented with L-glutamate (Gibco Invitrogen) and 1×B-27 (Gibco Invitrogen). After 4 days culture, the medium was removed and replaced with Neurobasal medium (Gibco Invitrogen) with or without 50 mM KCl. 15-30 min later the media were collected and GDNF concentrations were analysed by GDNF $E_{max}$® ImmunoAssay System (Promega) as recommended by the manufacturer.

Results

Figure 9:
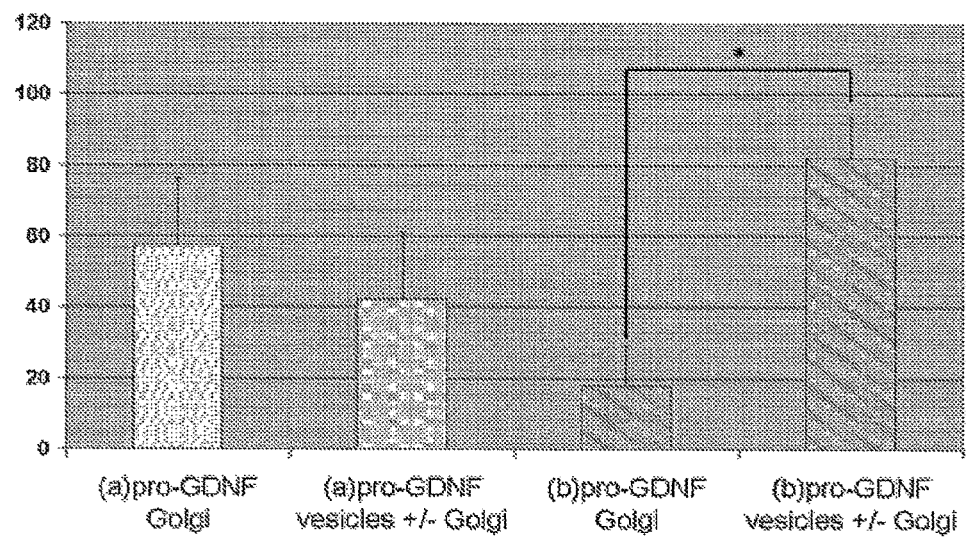
FIGS. 9A and 9B. Immunofluorescence analysis of subcellular localization of GDNF in differentiated PC-6.3 cells. Expression constructs containing human pre-(α)pro-GDNF or pre-(β)pro-GDNF were generated by cloning of cDNAs with stop-codons into pEGFP-N1 expression vector (Invitrogen). PC-6.3 cells were differentiated in differentiation medium containing Dulbecco's modified Eagle's medium (DMEM), 5% HS (Gibco), 2.5% FCS and 50 ng/ml nerve growth factor (NGF) for 3 days before transfection. 24 h after transfection, cells were either fixed with 4% PFA or first stimulated 2 h with 50 mM KCl and 50 µg/ml cycloheximide, which stops the protein synthesis, and then fixed with 4% PFA. All cells were blocked with 0.5% BSA (Sigma) and permeabilized with 0.1% Triton X-100 (Sigma). Cells were incubated with primary antibodies polyclonal anti-GDNF (GeneWay Biotech Inc.; 1:750 dilution) and monoclonal anti-GM130 for mature Golgi (Abcam; 1:100 dilution) in 0.5% BSA in RT for 1 hr, washed and then repeated with secondary antibodies. Images were acquired through a charge-coupled device camera (DP70; Olympus) on a microscope (AX70 Provis; Olympus).
Figure 9:
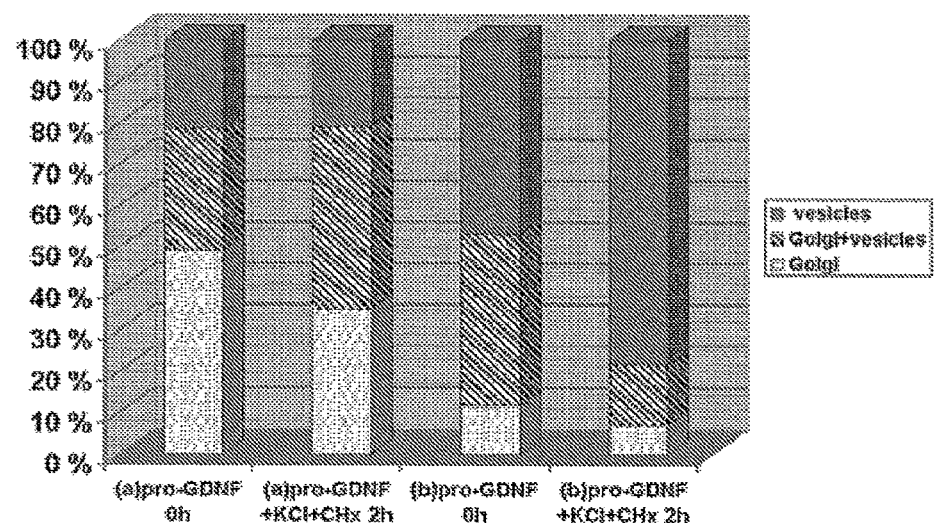
Figure 10:
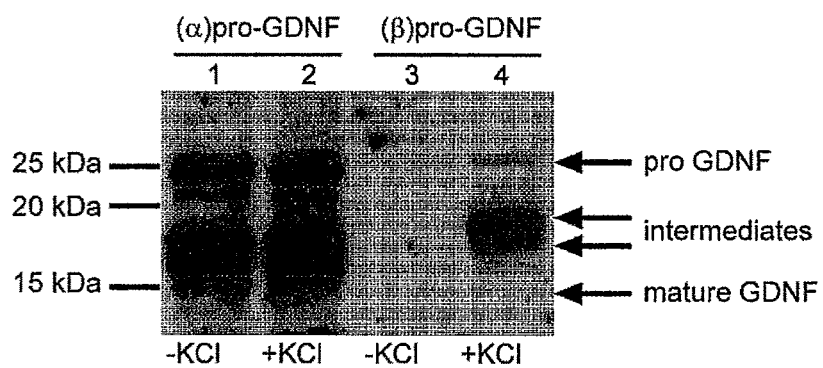
FIG. 10. Western blot analysis of mouse GDNF in cell medium collected from differentiated PC-6.3 cells. Expression constructs containing mouse pre-(α)pro-GDNF or pre-(β)pro-GDNF were generated by cloning of cDNAs with stop-codons into pEGFP-N1 expression vector (Invitrogen). PC-6.3 cells grown in DMEM with 10% Horse serum (HS) and 5% Fetal calf serum (FCS) and antibiotics were plated on 6-well plates and each well was transfected with 4 µg of plasmid when grown up to approximately 80% confluence. 4 hrs after post-transfection the media were replaced with differentiation medium containing DMEM with 5% HS and 2.5% FCS, 50 mg/ml nerve growth factor (NGF) and antibiotics. After 72 hours the PC-6.3 cells were depolarized with 25 mM KCl in DMEM for 5 hrs. The control (non-depolarized) cells were treated with DMEM. The media (supernatant) were collected and separated using 15% denaturating SDS-PAGE gel followed by blotting into nylon membrane and blocking with 5% milk in TBS-Tween (0.1%). GDNF was detected with rabbit anti-GDNF antibody (Santa Cruz, 1:500 dilution) and HRP-conjugated donkey anti-rabbit immunoglobulin secondary antibody (1:2000 dilution) by using ECL method. In the cell medium, pro-GDNF, processed intermediate pro-GDNF and mature GDNF bands are marked with arrows. Lane 1 non-depolarized PC-6.3 cells transfected with mouse pre-(α)pro-GDNF, medium; Lane 2 depolarized PC-6.3 cells transfected with mouse pre-(α)pro-GDNF, medium; Lane 3 non-depolarized PC-6.3 cells transfected with mouse pre-(β)pro-GDNF, medium; Lane 4 depolarized PC-6.3 cells transfected with mouse pre-(β)pro-GDNF, medium.
Figure 11:
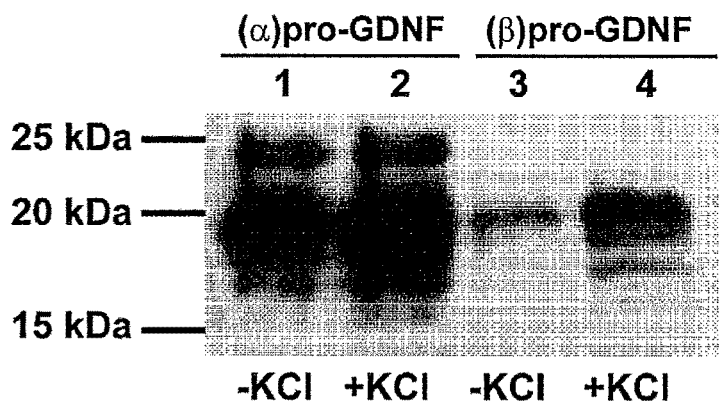
FIG. 11. Western blot analysis of human GDNF in cell medium collected from differentiated PC-6.3 cells. Expression constructs containing human pre-(α)pro-GDNF or pre-(β)pro-GDNF were generated by cloning of cDNAs with stop-codons into pAAV-MCS expression vector (Stratagene). PC-6.3 cells grown in DMEM with 10% HS and 5% FCS and antibiotics were plated on 6-well plates and each well was transfected with 4 µg of plasmid when grown up to approximately 80% confluence. 4 hrs after post-transfection the medium was replaced with differentiation medium containing DMEM with 5% HS and 2.5% FCS, 50 mg/ml NGF and antibiotics. After 72 hours the PC-6.3 cells were depolarized with 50 mM KCl in DMEM for 5 hrs. The control (non-depolarized) cells were treated with DMEM. The media (supernatant) were collected and separated using 15% denaturating SDS-PAGE gel followed by blotting into nylon membrane and blocking with 5% milk in TBS-Tween (0.1%). GDNF was detected with rabbit anti-GDNF antibody (Santa Cruz, 1:500 dilution) and HRP-conjugated donkey anti-rabbit immunoglobulin secondary antibody (1:2000 dilution) by using ECL method. Lane 1 non-depolarized PC-6.3 cells transfected with human pre-(α)pro-GDNF, medium; Lane 2 depolarized PC-6.3 cells transfected with human pre-(α)pro-GDNF, medium; Lane 3 non-depolarized PC-6.3 cells transfected with human pre-(β)pro-GDNF, medium; Lane 4 depolarized PC-6.3 cells transfected with human pre-(β)pro-GDNF, medium.
Figure 12:
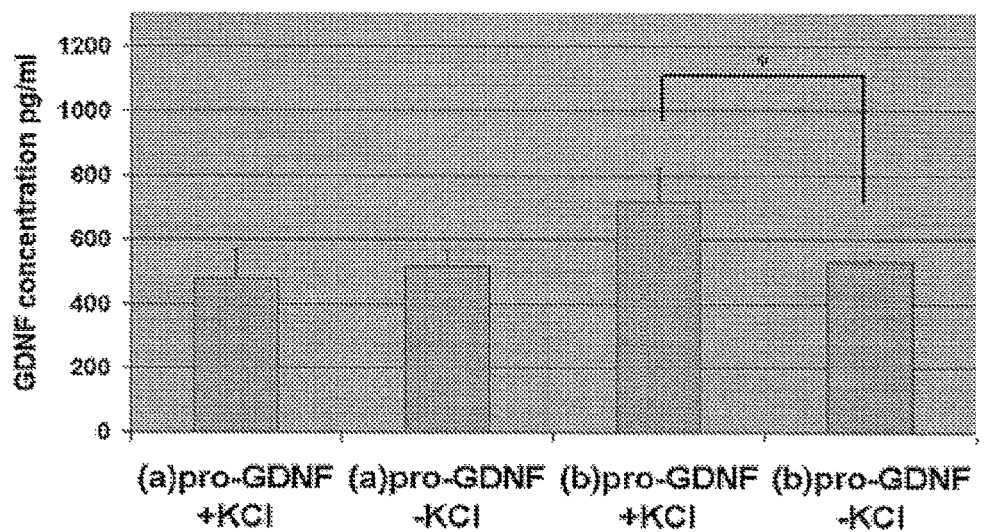
FIGS. 12A and 12B. Determination of GDNF concentration in PC-6.3 cell medium by ELISA analysis. Expression constructs containing mouse pre-(α)pro-GDNF or pre-(β)pro-GDNF were generated by cloning of cDNAs with stop-codons into pEGFP-N1 expression vector (Invitrogen). Expression construct containing rat pre-pro-BDNF without a stop codon in pEGFP-N1 expression vector (Invitrogen) was used as a control. PC-6.3 cells grown in DMEM with 10% HS and 5% FCS and antibiotics were plated on 24-well plates and each well was transfected with 0.8 µg of plasmid when grown up to approximately 80% confluence. 4 hrs after post-transfection medium was replaced with differentiation medium containing DMEM with 5% HS and 2.5% FCS, 50 mg/ml NGF and antibiotics. After 72 hours the PC-6.3 cells were depolarized with 50 mM KCl in DMEM for 2 hrs. The control (non-depolarized) cells were treated with DMEM. The media (supernatant) were collected and analysed using GDNF $E_{max}$ ImmunoAssay System (Promega) for GDNF and BDNF $E_{max}$ ImmunoAssay System (Promega) for BDNF.
Figure 12:
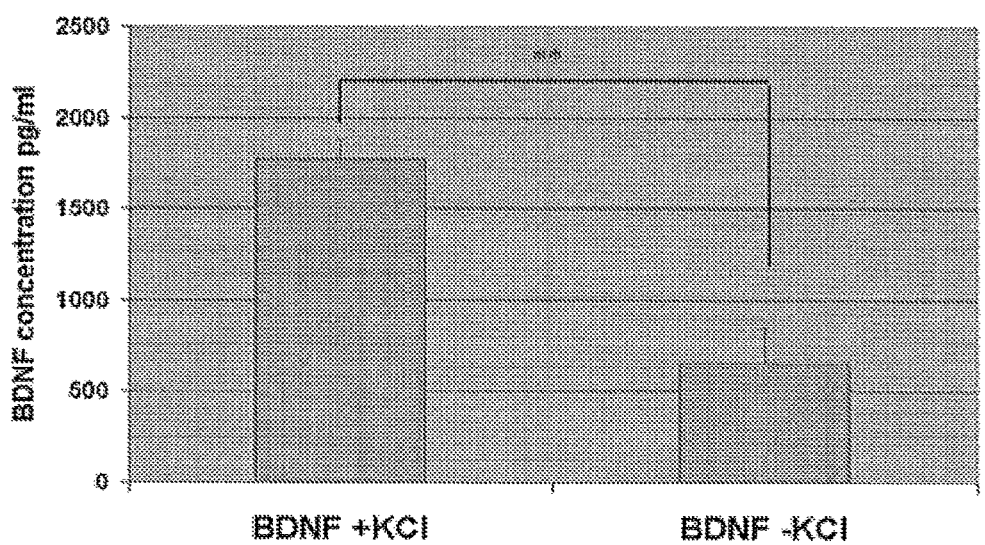

The results from immunofluorescence analysis show that, in differentiated PC-6.3 cells, there are clear differences between the localization of proteins encoded by pre-(α)pro-GDNF and pre-(β)pro-GDNF before and after stimulation. In non-stimulated PC-6.3 cells, GDNF encoded by pre-(α) pro-GDNF localized more frequently to the Golgi complex alone than to vesicles +/– Golgi (FIG. 9). In contrast, the majority of GDNF encoded by pre-(β)pro-GDNF localized in vesicles +/– Golgi and minority in Golgi alone. After KCl stimulation, (β)pro-GDNF and its mature GDNF form moved more rapidly to the vesicle compartment than (α)pro-GDNF and its mature GDNF form (FIG. 9). The results from Western blot analysis show that from differentiated neuronal-like PC-6.3 cells both mouse and human GDNF encoded by pre-(α)pro-GDNF cDNA are secreted constitutively, whereas the secretion of GDNF encoded by (β)pro-GDNF cDNA is activity-dependent (FIGS. 10 and 11). This result was further confirmed by ELISA analysis in which the secretion of rat BDNF was used as a positive control (FIG. 12). These results suggest that (β)pro-GDNF and its encoding cDNA may be much more potential therapeutic molecule for gene therapy treatment of PD than (α)pro-GDNF and its cDNA.

Discussion

Long-term in vivo expression of pre-(α)pro-GDNF by recombinant lentiviral vector delivery in the intact nigrostriatal dopamine system causes selective downregulation of tyrosine hydroxylase protein, a key enzyme in dopamine synthesis (Georgievska, et al., J. Neurosci., 24:6437-6445 (2004); Sajadi, et al., J. Neurochem., 93:1482-1486 (2005)). Moreover, continuous in vivo expression of pre-(α)pro-GDNF by recombinant lentiviral vector delivery to the striatum of 6-hydroxydopamine lesioned Parkinsonian rats induces down-regulation of tyrosine hydroxylase in the preserved striatal dopamine terminals (Georgievska, et al., Exp. Neurol., 177:461-474 (2002)). This is most likely due to a compensatory mechanism in which dopamine neurons under continuous GDNF stimulation are able to compensate for increased dopamine synthesis and release by decreasing tyrosine hydroxylase enzyme activity. Persephin is the member of GDNF family of neurotrophic factors. Experiments very clearly demonstrate that at high concentrations persephin is neurotoxic (Tomac, et al., Proc. Natl. Acad. Sci. USA, 99:9521-9526 (2002)). Recent experiments on non-human primates also indicate that high concentrations of GDNF induce cerebellar toxicity (Lang, et al., Ann Neurol., 59:459-466 (2006)). Therefore, future therapies should avoid high concentrations of GDNF and prefer systems, where the level of GDNF can be physiologically regulated. Our in vitro results show that the secretion of GDNF encoded by pre-(β)pro-GDNF is regulated by biological stimuli whereas the secretion of GDNF encoded by pre-(α) pro-GDNF is constitutive. This makes (β)pro-GDNF and its encoding cDNA much more potential therapeutic molecule for gene therapy treatment of PD than (α)pro-GDNF and its cDNA.

Example 4

Virus Vector Construction and Viral Particle Production

For viral vector construction, AAV Helper-Free System (Stratagene) is used according to manufacturer's instruction manual. By using appropriate restriction enzymes, the coding sequences for human pre-(α)pro-GDNF, pre-(β)pro-GDNF and pre-(γ)pro-GDNF-ATG are inserted into the multiple cloning site of pAAV-MCS or alternatively, into pAAV-IRES-hrGFP vector resulting in the vectors pAAV-MCS-pre-(α)pro-GDNF, pAAV-MCS-pre-(β)pro-GDNF, pAAV-MCS-pre-(γ)pro-GDNF-ATG or pAAV-IRES-hrGFP-pre-(α)pro-GDNF, pAAV-IRES-hrGFP-pre-(β)pro-GDNF, pAAV-IRES-hrGFP-pre-(γ)pro-GDNF-ATG, respectively. Above-mentioned vectors are co-transfected with pHelper and pAAV-RC vector into AAV-293 cells, which results to the production of pre-(α)pro-GDNF, pre-(β)pro-GDNF and pre-(γ)pro-GDNF-ATG expressing recombinant AAV particles. Vector pAAV-IRES-hrGFP is used accordingly to produce GFP expressing control virus particles.

Recombinant virus particles are produced and purified according to manufacturer's instruction manual for AAV Helper Free System (Stratagene). Aliquots of the recombinant viruses are stored at −80° C. The number of viral particles is determined using Southern dot blotting.

Example 5

In Vivo Gene Transfer in a Neuroprotective Animal Model of Parkinson's Disease

Animals.

Male Wistar rats (Harlan) weighing 250-280 g are housed in groups of three to four rats under a 12:12-h light:dark cycle at an ambient temperature of 22° C. Tap water and rat chow (Altromin 1324, Chr. Petersen A/S) are available ad libitum.

Viral Injections and 6-OHDA Lesioning.

All stereotaxic injections are done into the left striatum using coordinates relative to the bregma and dura (A/P+1.0, L/M+2.7, D/V −4) according to the atlas of Paxinos and Watson (The Rat Brain in Stereotaxic Coordinates. Academic press, San Diego, 1997). Stereotaxic surgery under isoflurane anaesthesia (4.5% during induction and 2.5% during surgery) is performed in two sessions essentially as described previously (Kearns et al., J. Neurosci., 17:7111-7118 (1997)). Animals are injected with recombinant AAV vector carrying the cDNA for GFP or pre-(α)pro-GDNF, pre-(β)pro-GDNF or pre-(γ)pro-GDNF-ATG (n=5-7/group). 14 days after rAAV injections the animals are re-anesthetized and a single deposit of 20 μg 6-OHDA (Sigma; calculated as free base and dissolved in 3 or 4 μl of ice-cold saline supplemented with 0.02% ascorbic acid) is injected into the striatum using coordinates relative to the bregma and dura (A/P+1.0, L/M+2.7, D/V −4). The injection rate is 1 μl/min and syringe is left in place for additional 3 min before withdrawal. Desipramine (Sigma; 15 mg/kg, i.p., 1 ml/kg) is administered prior to 6-OHDA injections in order to prevent the uptake of 6-OHDA into noradrenergic nerve endings, and thus to protect these nerve terminals from destruction.

Behavioral Testing.

At 10 days after rAAV injections and again 4 weeks after the 6-OHDA injections, rats are injected with amphetamine (2.5 mg/kg i.p.) and monitored for turning response in automated rotometer bowls (Colbourn Instruments, Inc., Allentown, Pa.) over 120 min After the rotational studies, the brains are perfused and collected for the immunohistochemistry.

Tyrosine Hydroxylase Immunohistochemistry.

At 28 days after the 6-OHDA injection the animals are deeply anesthetized with sodium pentobarbital and transcardially perfused with PBS followed by 200 ml ice-cold 4% paraformaldehyde (PFA). The brains are dissected and post-fixed in the same fixative for 3-4 h and transferred into 25% sucrose for 48 h. Series of 40 μm sections are cut on a freezing microtome. Immunohistochemistry for tyrosine hydroxylase (TH) is performed as described previously (Kirik et al., Eur. J. Neurosci., 13:1589-1599 (2001)).

Morphological Analysis: SN Cell Counts.

The number of TH-positive cells in SNpc is estimated using the optical fractionator method (West, et al., Anat. Rec., 231:482-497 (1991)). The SNpc is analyzed as described previously (Sauer, et al., Proc. Natl. Acad. Sci., 92:8935-8939 (1995)) with Stereo Investigator platform (MicroBrightField) attached to Olympus BX51 microscope. Briefly, from each animal, 3 sections from the central portion of the SNpc, where the medial terminal nucleus (MTN) was present (level A/P −5.3 mm in the atlas of Paxinos and Watson (Paxinos, G. & Watson, C., 1997, *The Rat Brain in Stereotaxic Coordinates*. Academic press, San Diego) are selected for quantitative analysis. Each reference space is outlined at low power (4×), and cells are counted using a high magnification (60×, oil immersion) objective. Cell numbers are expressed as the mean number/section. Cells are counted using the optical fractionator method in combination with the dissector principle and unbiased counting rules.

Statistical Analysis.

All the numbers of ipsilateral rotations and the numbers of TH-positive cells in the neuroprotection studies are analyzed by using one-way ANOVA followed by Tukey/Kramer's post-hoc test.

Example 6

In Vivo Gene Transfer in a Neurorestorative Animal Model of Parkinson's Disease

Animals.

Male Wistar rats (Harlan) weighing 250-280 g are housed in groups of three to four rats under a 12:12-h light:dark cycle at an ambient temperature of 22° C. Tap water and rat chow (Altromin 1324, Chr. Petersen A/S) are available ad libitum.

Viral Injections and 6-OHDA Lesioning.

All stereotaxic injections are done into the left striatum using coordinates relative to the bregma and dura (A/P+1.0, L/M+2.7, D/V-4) according to the atlas of Paxinos and Watson (*The Rat Brain in Stereotaxic Coordinates*. Academic press, San Diego, 1997). Stereotaxic surgery under isoflurane anaesthesia (4.5% during induction and 2.5% during surgery) is performed in two sessions essentially as described previously (Kearns et al., J. Neurosci., 17:7111-7118 (1997)). Each animal receives a single injection of 20 μg 6-OHDA (Sigma; calculated as free base and dissolved in 3 μl ice-cold saline supplemented with 0.02% ascorbic acid) is injected into the striatum using coordinates relative to the bregma and dura (A/P+1.0, L/M+2.7, D/V −4). The injection rate is 1 μl/min and syringe is left in place for additional 3 min before withdrawal. Desipramine (Sigma; 15 mg/kg, i.p., 1 ml/kg) is administered prior to 6-OHDA injections in order to prevent the uptake of 6-OHDA into noradrenergic nerve endings, and thus to protect these nerve terminals from destruction. Twenty eight days after 6-OHDA injections the animals are re-anesthetized and injected with recombinant AAV vector carrying the cDNA for GFP, pre-(α)pro-GDNF, pre-(β)pro-GDNF or pre-(γ)pro-GDNF-ATG (n=5-7/group). At 21 days after 6-OHDA injection, as well as 1, 2, 4 and 8 weeks after rAAV-pre-(α)pro-GDNF, rAAV-pre-(β)pro-GDNF or rAAV-pre-(γ)pro-GDNF-ATG delivery, rats are injected with amphetamine (2.5 mg/kg i.p.) and monitored for turning response in automated rotometer bowls (Colbourn Instruments, Inc., Allentown, Pa.) over 120 min. After the rotational studies, the brains are perfused and collected for the immunohistochemistry. Behavioral testing, tyrosine hydroxylase immunohistochemistry, morphological analysis and substantia nigra cell counts are carried as described here:

Tyrosine Hydroxylase Immunohistochemistry.

At 8 weeks after the AAV injection the animals are deeply anesthetized with sodium pentobarbital and transcardially perfused with PBS followed by 200 ml ice-cold 4% PFA. The brains are dissected and post-fixed in the same fixative for 3-4 h and transferred into 25% sucrose for 48 h. Series of 40 μm sections are cut on a freezing microtome. Immunohistochemistry for tyrosine hydroxylase (TH) is performed as described previously (Kirik et al., Eur. J. Neurosci., 13:1589-1599 (2001)).

Morphological Analysis: SN Cell Counts.

The number of TH-positive cells in SNpc is estimated using the optical fractionator method (West, et al., Anat. Rec., 231:482-497 (1991)). The SNpc is analyzed as described previously (Sauer et al., Proc. Natl. Acad. Sci., 92:8935-8939 (1995)) with Stereo Investigator platform (MicroBrightField) attached to Olympus BX51 microscope.

Briefly, from each animal, 3 sections from the central portion of the SNpc, where the medial terminal nucleus (MTN) is present (level A/P −5.3 mm in the atlas of Paxinos and Watson (Paxinos, G. & Watson, C., 1997, *The Rat Brain in Stereotaxic Coordinates*. Academic press, San Diego) are selected for quantitative analysis. Each reference space is outlined at low power (4×), and cells are counted using a high magnification (60×, oil immersion) objective. Cell numbers are expressed as the mean number/section. Cells are counted using the optical fractionator method in combination with the dissector principle and unbiased counting rules.

Example 7

Use of Viral Delivery of pre-(α)pro-GDNF, pre-(β) pro-GDNF or pre-(γ)pro-GDNF-ATG in the Animal Model of Epilepsy Electrode Implantation and Intraventricular Injection of the Virus.

Male Sprague Dawley rats (200-300 g) are anesthetized with sodium pentobarbital (50 mg/kg) and placed in a stereotaxic frame. Bipolar electrodes made from teflon-coated stainless steel wire are implanted into the right basolateral amygdala (from bregma: −2.8 mm anteroposterior; +4.9 mm lateral; and −8.6 mm dorsal) (Paxinos and Watson, The Rat Brain in Stereotaxic Coordinates. New York: Academic Press, Paper Back, 1997). The control rats are administered 4-8 µl of control virus (AAV-GFP) and the other rats are injected either with 4-8 µl of AAV expressing pre-(α)pro-GDNF, pre-(β)pro-GDNF or pre-(γ)pro-GDNF-ATG stereo-taxically with the tip in the right lateral ventricle (−0.8 mm anteroposterior; +1.5 mm lateral; and −3.6 mm dorsal) (Paxinos and Watson, The Rat Brain in Stereotaxic Coordinates. New York: Academic Press, Paper Back, 1997). Cannula and electrode are secured firmly to the skull with dental cement and anchor screws, and a ground wire was attached to one anchor screw (Binder et al. J. Neurosci., 19:1424-1436 (1999)). Animals are allowed to recover for 4 d after surgery before initiation of kindling stimulations.

Kindling Procedure.

Each kindling stimulation consists of a 60 Hz 1 sec train of 1 msec biphasic rectangular pulses at an amplitude 100 µA above the electrographic seizure threshold (EST). The EST is determined by increasing stimulation intensity on the first day of stimulation by 100 µA increments at 1 min intervals starting at 100 µA (Kokaia et al. Eur. J. Neurosci., 11:1202-1216 (1999)). Animals are stimulated twice per day for 11 d (22 total stimulations). Behavioral (seizure class) and electrophysiological [electrographic seizure duration (ESD)] parameters are recorded for each stimulation by an observer blinded to treatment. Behavioral seizure class is scored according to Racine's classification (Racine, 1972): class 0, no behavioral change; class 1, facial clonus; class 2, head nodding; class 3, unilateral forelimb clonus; class 4, rearing with bilateral forelimb clonus; and class 5, rearing and falling (loss of postural control).

Analysis of Animals.

Animals are decapitated at 4 or 24 h or 1 week after the last stimulation. Tissue is stained with triphenyltetrazolium chloride. In situ labeling analysis is used to detect apoptotic cells in cortical tissues.

Example 8

In Vivo rAAV-pre-(α)pro-GDNF, rAAV-pre-(β)pro-GDNF and rAAV-pre-(γ)pro-GDNF-ATG Gene Transfer in an Animal Model of Stroke rAAV-pre-(α)pro-GDNF, rAAV-pre-(β)pro-GDNF or rAAV-pre-(γ)pro-GDNF-ATG Delivery to Cortex.

To explore the potential of using the recombinant rAAV vector, expressing pre-(α)pro-GDNF, pre-(β)pro-GDNF or pre-(γ)pro-GDNF-ATG as the gene therapy for stroke, rAAV vector expressing pre-(α)pro-GDNF, pre-(β)pro-GDNF or pre-(γ)pro-GDNF-ATG is injected into the cortex of rats which have been experiencing transient bilateral common carotid artery ligation for 30 or 90 min (Arvidsson et al., Neurobiol. Dis., 14:542-556 (2003)). If pre-(α)pro-GDNF, pre-(β)pro-GDNF or pre-(γ)pro-GDNF-ATG levels in cortical tissues of rAAV-injected animals are significantly higher than in the control animals injected with rAAV expressing GFP (rAAV-GFP), this indicates that rAAV can deliver and express the pre-(α)pro-GDNF, pre-(β)pro-GDNF or pre-(γ)pro-GDNF-ATG gene in cortical tissues.

Induction of Global Forebrain Ischemia.

23 male Wistar rats (Taconic M&B A/S) weighing 280 to 290 g at the time of the ischemic insult are housed under 12-hour light/12-hour dark conditions with ad libitum access to food and water. After fasting overnight, animals are anaesthetized by inhalation of 3.5% halothane and then artificially ventilated with 1-2% halothane in $N_2O:O_2$ (70: 30). The tail artery and vein are cannulated for blood sampling and pressure recording, and drug infusion, respectively. A rectally placed thermometer is used to measure body temperature, which is maintained around 37° C. by a heating pad. The common carotid arteries are isolated. Fifty IU of heparin are then administered, the halothane concentration is decreased to 0.5%, and vecuronium bromide (Organon Teknika B.V., Boxtel, The Netherlands) is infused intravenously at 2 mg/h as muscle relaxant. A steady state period of 30 min follows, during which physiological parameters and electroencephalogram (EEG) are monitored. Ischemia is induced by bilateral occlusion of the common carotid arteries combined with hypotension (arterial blood pressure 40-50 mm Hg) achieved by blood withdrawal from the jugular vein. Circulation is restored after 10 min by reinfusion of blood and removal of the occluding clasps. In the immediate recirculation period, sodium bicarbonate (0.5 ml intravenously, 50 mg/ml) is given to prevent systemic acidosis (Arvidsson et al., Neuroscience, 106:27-41 (2001)).

Analysis of Animals.

Animals are decapitated at 4 and 24 h and 1 week after reperfusion (n=6 for each group). Sham-operated animals (n=5) are treated identically, but the common carotid arteries are not occluded. Tissue is stained with triphenyltetrazolium chloride. In situ labeling analysis is used to detect apoptotic cells in cortical tissues.

Example 9

In Vivo Gene Transfer in the Animal Model of Cholinergic Cell Death

Animals receive injections of viral vector into an in vivo rat model of cholinergic cell death, to determine the extent and parameters of pre-(α)pro-GDNF, pre-(β)pro-GDNF or pre-(γ)pro-GDNF-ATG vector delivery to prevent neuronal degeneration using in vivo gene delivery. To prepare the animal model, adult male Wistar rats undergo formix transections to induce basal forebrain cholinergic neuronal death. Pre-(α)pro-GDNF, pre-(β)pro-GDNF or pre-(γ)pro-GDNF-ATG vector (pAAV-MCS-pre-(α)pro-GDNF, pAAV-MCS-pre-(β)pro-GDNF or pAAV-MCS-pre-(γ)pro-GDNF-ATG) or control EGFP vector is injected into the cholinergic basal forebrain at a range of 2.5 to 10 µl of stock vector solution containing from $10^{10}$-$10^{12}$ particles per ml (neurotrophic composition). Particles are injected over a time period of 3-5 min into the right hemisphere at the following coordinates: AP-0.3; ML-0.5; DV-6 from brain surface. The skin is closed and animals are allowed to survive for 2-4 weeks.

Example 10

In Vivo Gene Transfer in the Animal Model of Familial Amyotrophic Lateral Sclerosis (ALS)

General.

Amyotrophic lateral sclerosis (ALS) is a relentlessly progressive lethal disease that involves selective degeneration of motoneurons. GDNF is proposed to be a promising therapeutic agent for ALS and other motor neuron diseases. Because AAV has been developed as an attractive gene delivery system with proven safety, we explore the therapeutic efficacy of intramuscular delivery of the GDNF cDNAs mediated by an AAV vector in the G93 A mouse model of ALS. G1H transgenic mouse model of familial ALS is carrying a human superoxide dismutase (SOD1) with a Gly93Ala mutation (Gurney et al. Science, 264:1772-1775 (1994)). Because AAV carrying the pre-(α)-GDNF splice isoform has been developed as an attractive gene delivery system with proven safety also for ALS (Wang et al. Gene Ther., 9:381-383 (2002)), we explore the therapeutic efficacy of intramuscular delivery of the pre-(α)pro-GDNF, pre-(β)pro-GDNF and pre-(γ)pro-GDNF cDNAs mediated by an AAV vector (rAAV-pre-(α)pro-GDNF, rAAV-pre-(β)pro-GDNF and rAAV-pre-(γ)pro-GDNF) in the G93A mouse model of ALS.

Animals and Viral Injections.

Male transgenic mice with the G93A human SOD1 mutation (SOD1G93A) are obtained from The Jackson Laboratory (Bar Harbor, Me.). AAV vector plasmid is described in detail above.

At 9-10 weeks of age, ALS mice are randomly assigned to three treatment groups that are injected with rAAV-pre-(α)pro-GDNF, rAAV-pre-(β)pro-GDNF or rAAV-pre-(γ)pro-GDNF vector (n=10) or one of two control groups that are injected with AAV-GFP vector (n=5) and the vehicle (n=5), respectively, into four limbs (gastrocnemius and triceps brachii muscles). The dosage is 25 µl for gastrocnemius and 15 µl for triceps brachii muscles.

Behavioral Testing.

Mice are first given 3 days to become acquainted with the rotarod apparatus (Rota-Rod/7650; or Rota-Rod Treadmill for Mice) before the test. For detection, mice are placed on the rotating rod at the speeds of 5, 10, and 20 rpm, and the time each mouse remains on the rod is registered automatically. The onset of disease is defined as the time when the mouse can not remain on the rod for 5 min at a speed of 20 rpm, as described previously (Li et al. Science, 288: 335-339 (2000)). If the mouse remains on the rod for >5 min, the test is completed and scored as 5 min. Mice are tested every 2 d until they can no longer perform the task. Mortality is scored as the age of death when the mouse is unable to right itself within 30 sec when placed on its back in a supine position (Li et al. Science, 288: 335-339 (2000)).

Morphological Analysis.

Muscle sections (10 µm) are fixed in cold acetone, followed by incubation with rabbit anti-GDNF D20 polyclonal antibody (1:500; Santa Cruz) as primary antibody and biotinylated anti-rabbit antibody as a secondary one (1:400; Santa Cruz). Sections are visualized by the avidin-biotin-peroxidase complex procedure (Vectastain ABC kits; Vector Laboratories) using 3,3-diaminobenzidine as a chromogen.

For double-immunofluorescence staining of muscles, sections are sequentially incubated with blocking solution, polyclonal rabbit anti-GDNF D20 antibody (1:500; Santa Cruz), FITC-conjugated goat anti-rabbit IgG (1:200; Santa Cruz), and tetramethylrhodamine-conjugated α-bungarotoxin (Molecular Probes). Sections are examined and photographed under a confocal laser scanning microscope (TCS NT; Leica, Heidelberg, Germany).

For morphological analysis of the spinal cord, serial transverse sections (30 µm) are obtained for Nissl, SMI-32, or CTB immunostaining. Free-floating sections are immunohistochemically stained for SMI-32 with a Mouse-on-Mouse kit (M.O.M kit) (Vector Laboratories), according to the protocol of the manufacturer. Sections processed for CTB immunoreactivity are blocked with 5% rabbit serum, followed by incubation with anti-CTB antibodies (1:10000, goat antiserum to CTB). Sections are visualized by standard ABC methods.

Morphometric Analysis and Cell Counting.

Morphometric analysis is performed on images captured with a CCD camera using Olympus BX51 microscope and KS 400 image analysis software (Zeiss). The mean area of muscle fibers is calculated from counts of >1000 fibers in randomly selected areas. To compare the number of motoneurons in the spinal cord, we count neurons in Nissl-stained and SMI-32- and CTB-immunostained sections spanning the cervical and lumbrosacral enlargements in each group, as described previously (Lewis et al. Nat. Genet., 25:402-405 (2000)). For each mouse, at least 20 sections in each sixth serial section are subjected to counting. Only large cell profiles meeting the following criteria are included: location in the ventral horn below a lateral line from the central canal, containing a distinct nucleus with a nucleolus, and possession of at least one thick process.

Example 11

In Vivo Gene Transfer in the Animal Model of Spinal Cord Injury

General.

Delivery of neurotrophic factors to the injured spinal cord has been shown to stimulate neuronal survival and regeneration. This indicates that a lack of sufficient trophic support is one factor contributing to the absence of spontaneous regeneration in the mammalian spinal cord. Previously the delivery of pre-(α)pro-GDNF was mediated by a recombinant adenovirus (AdCMVgdnf or AdCMVlacZ) and tested for the functional recovery and central neuronal atrophy in adult rats with spinal cord injury. The results revealed that adenovirus-mediated delivery of pre-(α)pro-GDNF could prevent the retrograde atrophy of corticospinal motoneurons and improve the motor function in rats with spinal cord injury (Tang et al. Neuroreport; 15:425-429 (2004)).

Using the gene delivery approach that provides trophic support, we inject the AAV vector expressing the pre-(α)pro-GDNF, pre-(β)pro-GDNF or pre-(γ)pro-GDNF (rAAV-pre-(α)pro-GDNF, rAAV-pre-(b)pro-GDNF or rAAV-pre-(γ)

pro-GDNF) into spinal cord lesion sites. We analyze on adult spinal cord injured rats anatomically for corticospinal tract (CST) regeneration and behaviorally for improvement of sensory-motor functions.

Animals.

All experiments are performed in Laboratory Animal Center of the University of Helsinki where all laboratory animal studies and protocols follow the Finnish national legislation, EU directive (86/609), European Convention (ETS 123) and national gene technology. Adult female Lewis rats (160-190 gm) are kept as groups of four to six animals in standardized cages on a 12-hour-light 12-hour-dark cycle on a standard regimen with food and water ad libitum. Animals are anesthetized with a subcutaneous injection of Hypnorm (120 µl/200 g of body weight; Janssen Pharmaceutics) and Dormicum (0.75 mg in 150 µl per 200 g of body weight; Roche Pharmaceuticals). Vitamin A-containing eye pointment is applied to protect the eyes from dehydration during the relatively long procedure. A T-shaped lesion that included the dorsal half of the spinal cord with the main CST as well as the dorsolateral and ventromedial parts of the CST is made at thoracic level T8 with iridectomy scissors and a sharp, pointed blade following the procedure by Liebscher et al. (Liebscher et al. Ann. Neurol., 58:706-719 (2005)).

Delivery of the Virus.

Animals are operated on in four (rAAV-pre-(α)pro-GDNF, rAAV-pre-(β)pro-GDNF, rAAV-pre-(γ)pro-GDNF and AAV-GFP) batches and undergo an identical surgical and behavioral procedure. The experiment is performed in a fully double-blind manner: the rats are coded with random numbers and the groups are mixed in the cages. All experimenters are blind to the treatments throughout all phases of the experiment, which includes operation, health care, behavioral, and evaluation of regeneration, sprouting, and lesion size.

Before surgery, all animals are handled and trained for the behavioral tests for 4 weeks before baseline measurements are taken. For AAV injections, rats are randomly divided into the experimental groups: lesion+rAAV-pre-(α)pro-GDNF, lesion+rAAV-pre-(β)pro-GDNF, lesion+rAAV-pre-(γ)pro-GDNF, lesion+control AAV-GFP. AAV injection starts immediately after the lesion by rinsing the wound with 1 µl of the physiological solution. After 2 weeks the behavioral assessments start and are repeated at weekly intervals. After 5 weeks, the CST is unilaterally traced. Nine weeks after surgery, at the end of the behavioral protocol, the morphological analysis is carried out.

BBB Locomotor Score.

All tests are monitored by a digital video camera and analyzed in a double-blind manner. Before the surgery, after 4 weeks of pretraining, baseline measurements are taken. After the operation, behavioral assessments are taken at weekly intervals. Rats are allowed to move freely and are scored during 4 minutes by two observers for their ability to use the hindlimbs. Joint movements, paw placement, weight support, and fore/hindlimb coordination are judged according to the 21-point BBB locomotion scale (Basso et al. J. Neurotrauma, 12:1-12 (1995)).

Swim Test.

The setup for the Swim Test consists of a rectangular Plexiglas basin (150×40×13 cm). The level of the water (23-25° C.) is high enough to prevent the rats from touching the bottom of the basin. Intact animals swim by paddling with their hindlimbs and the tail, holding their forelimbs immobile under the chin (Stolz et al. Behav. Brain Res., 106:127-132 (1999)). A total of five runs per rat are monitored using a mirror at 45 degrees at the bottom of the pool to film the rats from the side and the bottom simultaneously. The swimming performance is analyzed by scoring their movements according to the following criteria: forelimb usage: 2 points=no use (normal), 1 point=1 arm for the whole distance or both for half the distance, 0 points=both arms used all the time; hind-paw distance (base of support): 2 points=small distance, hindlegs are underneath the body, 1 point=legs are outside the body, but feet still remain underneath, 0 points=large distance, legs and feet are outside the body; hindlimb stroke: 2 points=powerful strokes, 1 point=moderate strokes, 0 points=weak or no strokes; tail movement: 2 points=regular strong movements of the whole tail; 1 point=partial movements; 0 points=no or only very weak movements. Normal swimming thus results in seven to eight score points, a value that was routinely reached by well-trained rats.

Fiber Counting and Sprouting Scores

The number of regenerating fibers originating from the main CST is counted on complete series of sagittal sections at a final magnification of 400× in three defined areas of 0.25 mm rostrocaudal width, at 0.5 mm, 2 mm, and 5 mm caudal to the lesion site. Scores (0=absence of sprouting, 3=very strong sprouting) are assigned by experienced, blinded observers judging the density, abnormal course, curving toward and around the lesion, length, and arborization of CST sprouts immediately rostral to the lesion.

Example 12

Raising Antibodies 320/(α)pro-GDNF, 321/pro-GDNF and 322/(β)pro-GDNF Against the GDNF Pre-Pro Region Peptide Synthesis Three peptides were prepared, one for each of the antibodies to be raised. The peptides are as follows:

```
                                          (SEQ ID NO: 46)
peptide A320: CGKRLLEAPAEDHSLGHRRVP
for 320/(α)pro-GDNF,
                                          (SEQ ID NO: 47)
peptide A321: CPEDYPDQFDDVMD
for 321/pro-GDNF and
                                          (SEQ ID NO: 48)
peptide A322: CHTASAFPLPAANM
for 322/(β)pro-GDNF.
```

The preparation of the peptides is based on the solid phase peptide synthesis (SPPS) technique using Fmoc-chemistry. Fmoc stands for 9-fluorenylmethyl chloroformate (9H(f)luoren-9-yl(m)eth(o)xy(c)arbonyl) which describes the Fmoc protecting group added to $N^\alpha$ of an amino acid, to prevent unwanted reactions, and is stable under acidic conditions. The synthesis was carried out from the C-terminus to the N-terminus of peptide using automated synthesis in 0.1 mmol scale following the standard procedure (Benoiton, Chemistry of Peptide Synthesis, Taylor & Francis Group, 2005). During synthesis, functional groups of the amino acid side chains were protected with permanent protecting groups, which were also cleaved after completion of the synthesis, but they are stable to all chemical reagents during the synthesis. After cleavage, peptide purity was controlled with HPLC (High Performance Liquid Chromatography) technology (peptide was dissolved in acetonitrile), mass of different fractions from HPLC controlled with MALDI TOF-MS (Matrix Assisted Laser Desorption Ionization Time-of-flight Mass Spectrometry) and freeze-dried in lyophilization equipment. Additionally, 2 mg of peptide was purified in HPLC for immunization (>95% pure). Peptide-resin is stored at −20° C. and peptide powder at +4° C.

KLH Conjugation 2 mg of pure peptide was conjugated to carrier protein KLH (keyhole limpet hemocyanin), to stimulate an immune response in later immunization process. KLH is suitable, because it has a large molecular mass (MW $4.5 \times 10^5$ to $1.3 \times 10^7$), strong immunogenicity and many available lysines for conjugation process. For conjugation to peptides, maleimide activated KLH was used. The maleimide group reacts with SH-groups of Cysteine, which was added to N-terminus of the peptide—only one Cys per peptide and internal Cys was avoided, to assure site-directed conjugation and unshadowed peptide for immune process. Reaction was carried out under neutral conditions and later purified using dialysis. Final solution was in PBS with concentration 0.5 mg/ml of conjugate. Conjugation step was controlled with Ellman test using samples, collected before and after the conjugation step (peptide with and without KLH). Ellman test was made to estimate the efficiency of conjugation of sulfhydryl-containing peptide to KLH by using Ellman's reagent (5,5'-dithiobis(2-nitrobenzoic acid) or DTNB) (Walker, The Protein Protocols Handbook, 2nd edition, Humana Press inc. 2002, pp 595-596).

Immunization

Immunization timetable: Day 0—preimmune serum and I immunization; Day 14—second immunization; Day 35—III immunization: Day 45—preliminary bleeding and ELISA testing; Day 56—IV immunization; Day 66—final bleeding and ELISA testing. First immunization was made with Freund's Complete Adjuvant (FCA), other immunizations with Freund's Incomplete Adjuvant (FIA). Freund's Adjuvants are water-in-oil emulsions, FCA containing also killed *Mycobacterium tuberculosis* and they are used to enhance immune response. Adjuvant was carefully mixed with KLH-peptide conjugate solution to 1:1 and injected subcutaneously into two sites. In one project 2 rabbits were used. Blood was collected from air vain and clotted-centrifuged for serum preparation. The amount of preimmune serum was ~1 ml, preliminary serum for ELISA testing ~0.3 ml and final serum ~30 ml.

ELISA

Appropriate amount of peptide A320, A321 or A322 was conjugated to Bovine Serum Albumin (BSA) (same procedure as for KLH conjugation). This peptide-BSA conjugate was then coated onto a high-capacity protein-binding microtiter plate (each sample in 2 reps). Preimmune, preliminary and final serum were detected by standard ELISA using an anti-rabbit IgG antibody as secondary antibody conjugated to Horse Radish Peroxidase (HRP) and 3,3',5,5'-tetramethylbenzidine (TMB) as a substrate. The optical density was measured at 450 nm with ELISA-reader.

IgG-Specific Purification

For IgG-purification MAbsorbent® technology was used. MAbsorbent® synthetic affinity ligand absorbent is validated for the purification of antibodies from serum, plasma, ascitic fluid, mammalian cell culture supernatant or transgenic sources and are the innovative alternative to Protein A purification. The purification of the antibodies from the blood antiserum is carried out by binding them with the MAbsorbent A1P/A2P. MAbsorbent synthetic affinity ligand absorbent "mimics" recombinant and natural Protein A. However, they are very different in that MAbsorbents bind to all subclasses of IgG. It effectively binds a wide variety of human and mammalian polyclonal antibodies (including bovine, mouse, sheep, goat, horse and rabbit) as well as whole monoclonal antibodies, humanized antibody chimeras and antibody fragments.

As first part, the column was prepared according to instructions supplied with the empty column and with the MAbsorbent. Briefly, the slurry of absorbent was mixed gently, added to the column and column was equilibrated with binding buffer.

Secondly, appropriate amount of antiserum diluted in binding buffer was added to the column, incubated and was let to flow through. Antibodies from serum bound to MAbsorbent A1P/A2P. Column was then washed, antibodies were eluted from the affinity absorbent and collected into 2 ml fractions. After that, column was equilibrated again for new purification. This step can be repeated, till needed amount of antiserum is purified. Equilibration and binding are made at neutral pH, elution under acidic conditions. After collection, all fractions were dialysed against PBS and antibody concentration was measured with BCA™ protein assay technology. Finally, antibodies are in phosphate buffered saline (PBS) and stored at −20° C.

Epitope-Specific Purification

For epitope-specific affinity purification NHS-activated Sepharose® matrix technology was used. NHS-activated sepharose gives stable amide bond with antigen, at this time with peptide, which will later bind antibodies from serum. Antibodies will be eluted and collected. This method helps to purify antibodies in the serum against given peptide.

As first part, the column was prepared according to instructions supplied with the empty column and NHS-activated Sepharose® matrix. Briefly, NHS-activated Sepharose® matrix was put into the empty column and washed to remove store solution. The antigen, dissolved in the coupling solution, was added to the column to be bound to the active groups of the sepharose during incubation period. Any non-reacted active groups in the medium were then blocked by standing in TRIS-buffer. Then the column was washed with two different buffers, having different pH-values, e.g. 8-9 for the first buffer and 3-4 for the second buffer.

Secondly, pre-prepared column was equilibrated with binding buffer and appropriate amount of blood antiserum, diluted in PBS, was loaded into column. The slurry was kept there for some minutes to bind the antibodies with the antigens. The column was washed with binding buffer at different pH's (pH 8-6.5), then the antibodies were eluted under acid conditions and the fractions were collected by 1 ml. After collection, all fractions were dialysed against PBS and antibody concentration was measured with BCA™ protein assay technology. Finally, antibodies are in phosphate buffered saline (PBS) and stored at −20° C.

Characterization of the Specificity of the Pro-GDNF Antibodies

The specificity of pro-GDNF antibodies was verified by Western blotting and immunofluorescence analysis. In immunofluorescence analysis, CHO cells grown in DMEM with 10% FCS and antibiotics were plated on 4-well plates with coverslips and each well was transfected with 0.8 μg of plasmid when grown up to approximately 80% confluence. The constructs used for transfections were human and/or mouse pre-(α)pro-GDNF and pre-(β)pro-GDNF in pEGFP vector (Invitrogen) as well as human pre-(γ)pro-GDNF containing ATG as a protein coding initiation codon in pAAV-MCS vector. Human pre-GDNF in pAAV-MCS vector, which lacks the pro domain, was used as a control (a gift from Dr. Pia Runeberg-Roos, University of Helsinki, Finland). This construct was cloned similarly than other constructs used. Expression of recombinant GFP protein, expressed from an empty pEGFP-N1 vector, was used as a mock-transfection control. The media were replaced with fresh DMEM with 10% FCS and antibiotics 4 hrs after transfection. 24 hrs post-transfection, the cells were fixed with 4% paraformaldehyde (Sigma) and permeabilized with 0.1% Triton X-100 (Sigma). Cells were incubated with primary antibodies polyclonal 320/(α)pro-GDNF (1:200 dilution), 321/pro-GDNF (1:200 dilution) or 322/(β)pro-GDNF (1:200 dilution) for GDNF pro-domains and monoclonal mouse anti-GDNF antibody for mature GDNF (1:100 dilution) in 0.5% BSA in RT for 1 hr, washed and then repeated with secondary antibodies Cy2 conjugated donkey anti-mouse IgG (Jackson ImmunoResearch laboratories) and Cy3-conjugated donkey anti-rabbit IgG (Jackson ImmunoResearch laboratories). Nuclei were stained with Hoechst and finally coverslips were mounted with Immu-mount (Thermo electron corporation). Images were acquired through a charge-coupled device camera (DP70; Olympus) on a microscope (AX70 Provis; Olympus). In Western blot analysis, CHO cells grown in DMEM with 10% FCS and antibiotics were plated on 6-well plates and each well was transfected with 4 µg of plasmid when grown up to approximately 80% confluence. The constructs used for transfections were human and mouse pre-(α)pro-GDNF and pre-(β)pro-GDNF in pEGFP-N1 vector (Invitrogen), human pre-(α)pro-GDNF and pre-(β)pro-GDNF in pAAV-IRES-hrGFP vector (Stratagene), human pre-(α)pro-GDNF and pre-(β)pro-GDNF in pAAV-MCS vector (Stratagene). Human pre-GDNF in pAAV-MCS vector, which lacks the pro domain, was used as a control. This construct was cloned similarly than other constructs used. Expression of recombinant GFP protein, expressed from an empty pEGFP-N1 vector, was used as a mock-transfection control. The media were replaced with 2 ml OptiMEM medium 4 hrs after transfection. The cells and media (supernatant) were collected 48 hrs post-transfection, the media were concentrated and the samples were separated using 15% desaturating SDS-PAGE gel followed by blotting into nylon membrane and blocking with 5% milk in TBS-Tween (0.1%). GDNF was detected with polyclonal 320/(α)pro-GDNF (1:500 dilution) or 32 l/pro-GDNF (1:500 dilution) for GDNF pro-domains and polyclonal D20 antibody for mature GDNF (Santa Cruz, 1:500 dilution) followed by HRP-conjugated donkey anti-rabbit immunoglobuln secondary antibody (1:2000 dilution) by using ECL method.

Results

Figure 13:
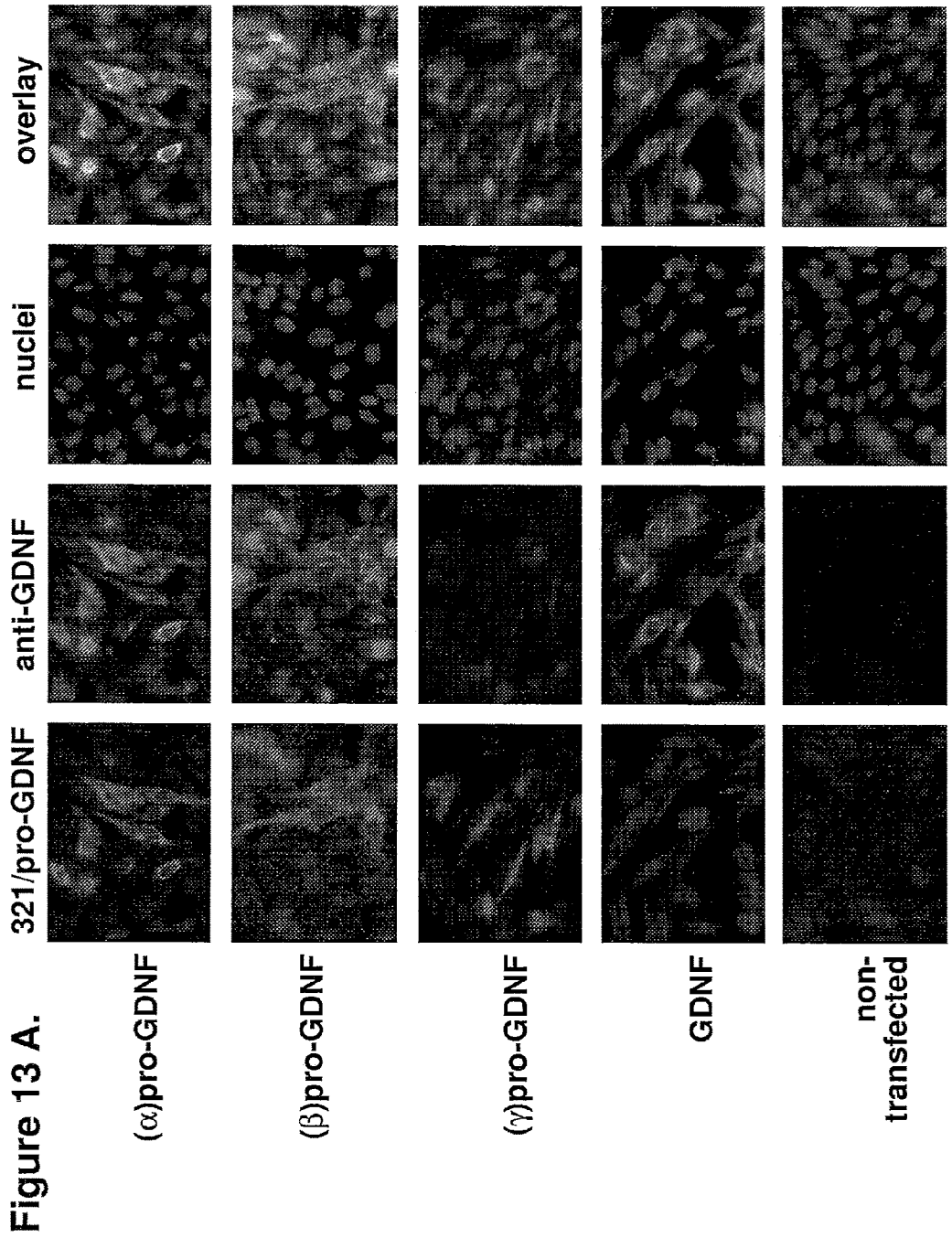
FIGS. 13A and 13B. Immunofluorescence analysis of the specificity of the 321/pro-GDNF antibody recognising the pro-domains of pre-(α)pro-GDNF, pre-(β)pro-GDNF and pre-(γ)pro-GDNF in CHO cells. Expression construct containing mouse pre-(α)pro-GDNF was generated by cloning of cDNA with stop-codons into pEGFP-N1 vector (Invitrogen). Expression constructs containing human pre-(β)pro-GDNF, human pre-(γ)pro-GDNF containing ATG as a protein coding initiation codon and human pre-GDNF were generated by cloning of cDNAs with stop-codons into pAAV-MCS expression vector (Stratagene). Green fluorescent protein (GFP) was expressed from an empty pEGFP-N1 vector. CHO cells grown in DMEM with 10% FCS and antibiotics were plated on 4-well plates with coverslips and each well was transfected with 0.8 µg of plasmid when grown up to approximately 80% confluence. The media were replaced with fresh DMEM with 10% FCS and antibiotics 4 hrs after transfection. 24 hrs post-transfection, the cells were fixed with 4% paraformaldehyde (Sigma) and permeabilized with 0.1% Triton X-100 (Sigma). Cells were incubated with primary antibodies polyclonal 321/pro-GDNF for GDNF pro-domain (1:200 dilution) and monoclonal mouse anti-GDNF for mature GDNF (1:100 dilution) in 0.5% BSA in RT for 1 hr, washed and then repeated with secondary antibodies. Nuclei were stained with Hoechst. Images were acquired through a charge-coupled device camera (DP70; Olympus) on a microscope (AX70 Provis; Olympus).
Figure 13:
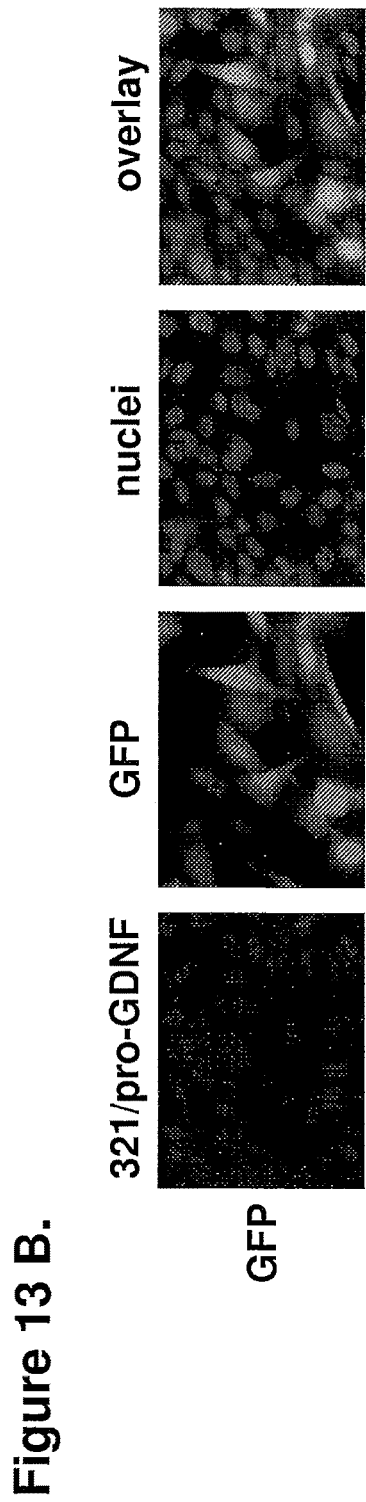
Figure 14:
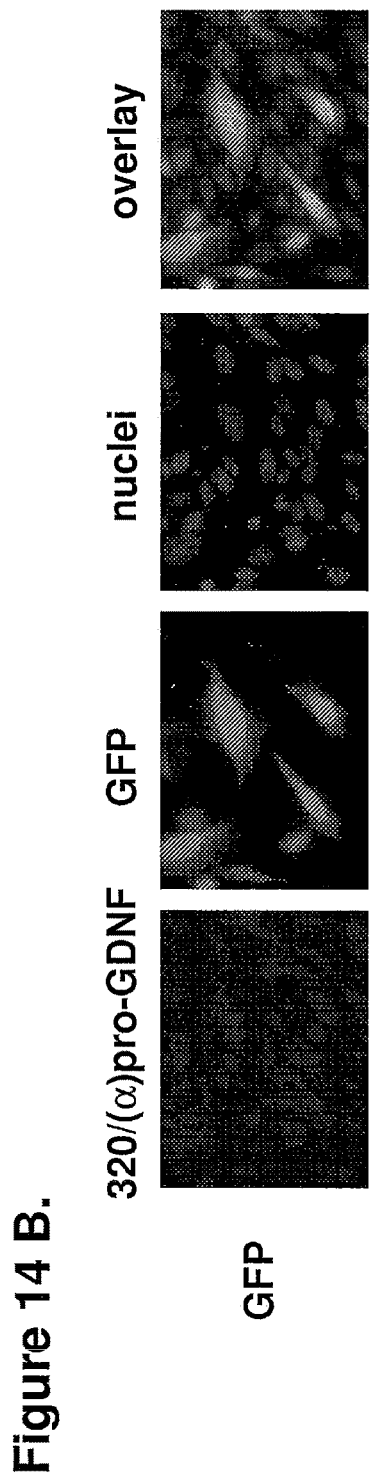
FIGS. 14A and 14B. Immunofluorescence analysis of the specificity of the 320/(α)pro-GDNF antibody recognising the pro-domain of pre-(α)pro-GDNF in CHO cells. Expression constructs containing mouse pre-(α)pro-GDNF and pre-(β)pro-GDNF were generated by cloning of cDNA with stop-codons into pEGFP-N1 vector (Invitrogen). Expression constructs containing human pre-(γ)pro-GDNF containing ATG as a protein coding initiation codon and human pre-GDNF were generated by cloning of cDNAs with stop-codons into pAAV-MCS expression vector (Stratagene).
Figure 15:
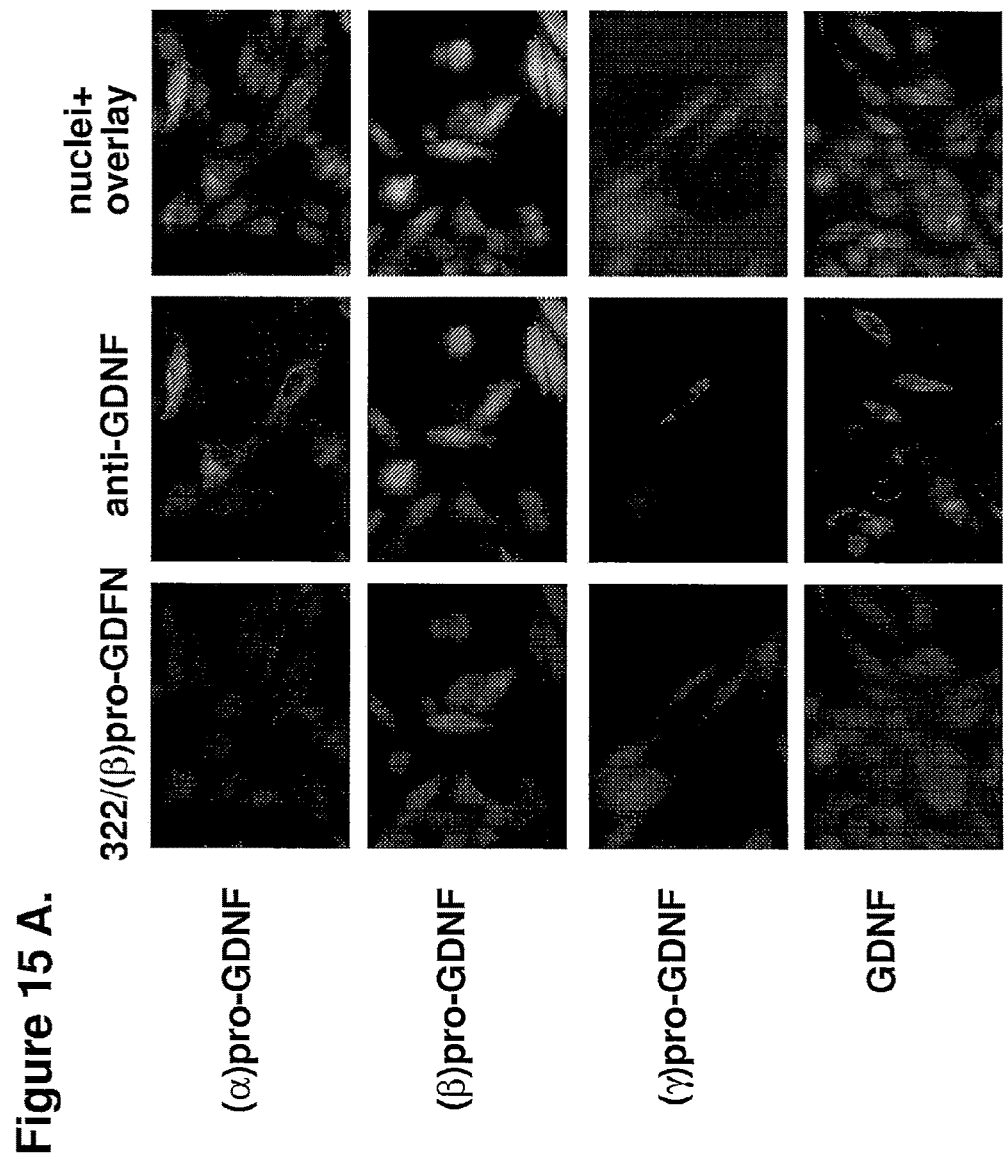
FIGS. 15A and 15B. Immunofluorescence analysis of the specificity of the 322/(β)pro-GDNF antibody recognising the pro-domain of pre-(β)pro-GDNF in CHO cells. Expression constructs containing mouse pre-(α)pro-GDNF and pre-(β)pro-GDNF were generated by cloning of cDNA with stop-codons into pEGFP-N1 vector (Invitrogen). Expression constructs containing human pre-(γ)pro-GDNF containing ATG as a protein coding initiation codon and human pre-GDNF were generated by cloning of cDNAs with stop-codons into pAAV-MCS expression vector (Stratagene). GFP was expressed from an empty pEGFP-N1 vector. CHO cells grown in DMEM with 10% FCS and antibiotics were plated on 4-well plates with coverslips and each well was transfected with 0.8 μg of plasmid when grown up to approximately 80% confluence. The media were replaced with fresh DMEM with 10% FCS and antibiotics 4 hrs after transfection. 24 hrs post-transfection, the cells were fixed with 4% paraformaldehyde (Sigma) and permeabilized with 0.1% Triton X-100 (Sigma) Cells were incubated with primary antibodies polyclonal 322/(β)pro-GDNF for (β)pro-GDNF pro-domain (1:200 dilution) and monoclonal mouse anti-GDNF for mature GDNF (1:100 dilution) in 0.5% BSA in RT for 1 hr, washed and then repeated with secondary antibodies. Nuclei were stained with Hoechst. Images were acquired through a charge-coupled device camera (DP70; Olympus) on a microscope (AX70 Provis; Olympus).
Figure 15:
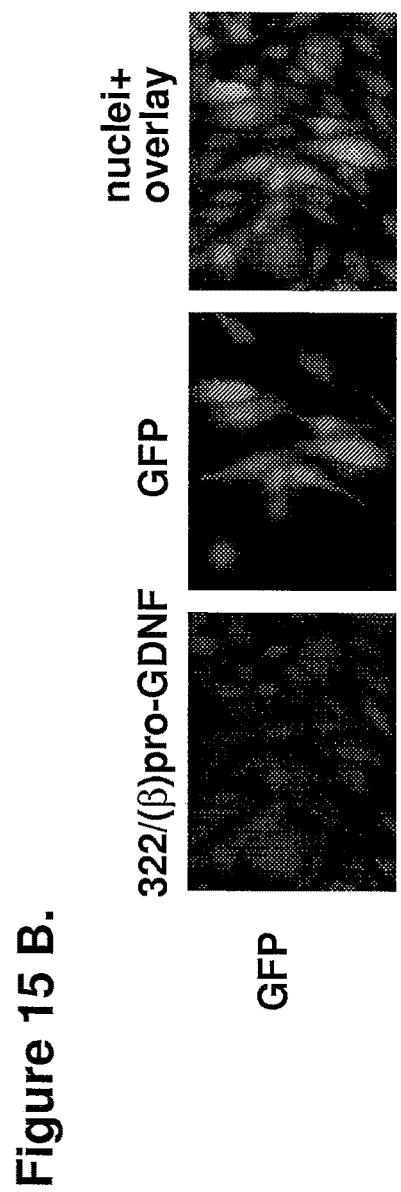

The results from immunofluorescence analysis show that the 321/pro-GDNF antibody recognises the GDNF pro-domain of (α)pro-GDNF, (β)pro-GDNF and (γ)pro-GDNF whereas it does not recognise the GDNF protein lacking the pro region or recombinant GFP protein. In addition, no specific staining is seen in non-transfected cells. (α)pro-GDNF and (β)pro-GDNF, as well as GDNF protein lacking the pro region, are also detected with mouse anti-GDNF antibody recognising the mature part of GDNF (FIG. 13). In immunofluorescence analysis, the 320/(α)pro-GDNF antibody recognises the GDNF pro-domain of (α)pro-GDNF but it does not recognise the (β)pro-GDNF, (γ)pro-GDNF, GDNF lacking the pro region or recombinant GFP protein. (α)pro-GDNF and (β)pro-GDNF, as well as GDNF protein lacking the pro region, are also detected with mouse anti-GDNF antibody recognising the mature part of GDNF. In addition to mouse anti-GDNF staining, some GFP signal (green), most likely leaking from the pEGFP-N1 vector, is seen in the cells transfected with pre-(β)pro-GDNF cDNA (FIG. 14). In immunofluorescence analysis, the 322/(β)pro-GDNF antibody recognises the GDNF pro-domain of (β)pro-GDNF but it does not recogrise the (α)pro-GDNF, (γ)pro-GDNF, GDNF lacking the pro region or recombinant GFP protein. (α)pro-GDNF and (β)pro-GDNF, as well as GDNF protein lacking the pro region, are also detected with mouse anti-GDNF antibody recognising the mature part of GDNF. In addition to mouse anti-GDNF staining, some GFP signal, most likely leaking from the pEGFP-N1 vector, is seen in the cells transfected with pre-(β)pro-GDNF cDNA (FIG. 15).

Figure 16:
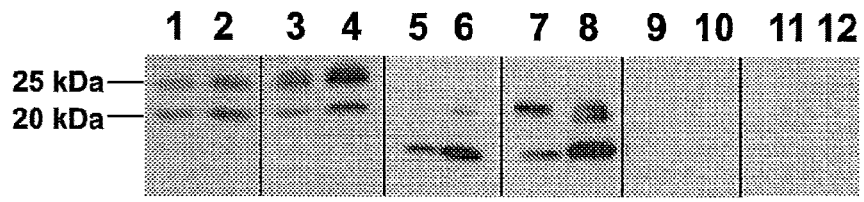
FIGS. 16A, 16B and 16C. Western blot analysis of the specificity of the 321/pro-GDNF antibody recognising the pro-domains of pre-(α)pro-GDNF, pre-(β)pro-GDNF and pre-(γ)pro-GDNF in CHO cells. CHO cells grown in DMEM with 10% FCS and antibiotics were plated on 6-well plates and each well was transfected with 4 μg of plasmid when grown up to approximately 80% confluence. The media were replaced with 2 ml OptiMEM medium 4 hrs after transfection. The cells and media (supernatant) were collected 48 hrs post-transfection, the media were concentrated and the samples were separated using 15% denaturating SDS-PAGE gel followed by blotting into nylon membrane and blocking with 5% milk in TBS-Tween (0.1%). GDNF was detected with either polyclonal 321/pro-GDNF antibody (1:500 dilution) or polyclonal D20 antibody for mature GDNF (Santa Cruz, 1:500 dilution) and HRP-conjugated donkey anti-rabbit immunoglobulin secondary antibody (1:2000 dilution) by using ECL method. Lane 1 CHO cells transfected with human pAAV-MCS-pre-(α)pro-GDNF, cells; Lane 2 CHO cells transfected with human pAAV-IRES-hrGFP-pre-(α)pro-GDNF, cells; Lane 3 CHO cells transfected with human pAAV-MCS-pre-(α)pro-GDNF, media; Lane 4 CHO cells transfected with human pAAV-IRES-hrGFP-pre-(α)pro-GDNF, media; Lane 5 CHO cells transfected with human pAAV-MCS-pre-(β)pro-GDNF, cells; Lane 6 CHO cells transfected with human pAAV-IRES-hrGFP-pre-(β)pro-GDNF, cells; Lane 7 CHO cells transfected with human pAAV-MCS-pre-(β)pro-GDNF, media; Lane 8 CHO cells transfected with human pAAV-IRES-hrGFP-pre-(β)pro-GDNF, media; Lane 9 CHO cells transfected with empty pEGFP-N1 vector expressing GFP, cells; Lane 10 CHO cells transfected with human pAAV-MCS-pre-GDNF, cells; Lane 11 CHO cells transfected with empty pEGFP-N1 vector expressing GFP, media; Lane 12 CHO cells transfected with human pAAV-MCS-pre-GDNF, media.
Figure 16:
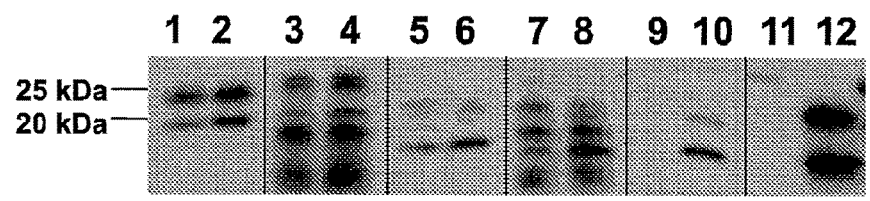
Figure 16:
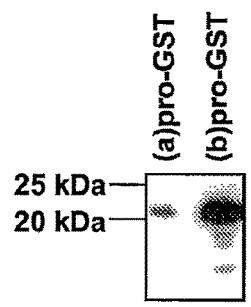
Figure 17:
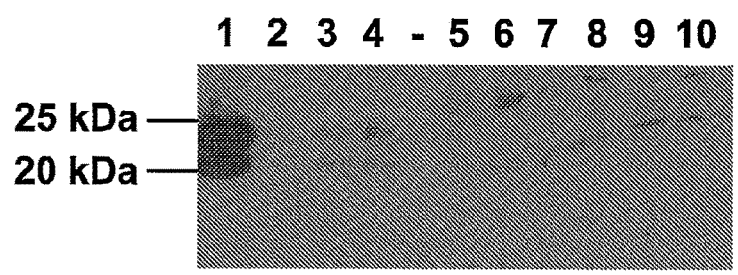
FIGS. 17A, 17B, 17C and 17D. Western blot analysis of the specificity of the 320/(α)pro-GDNF antibody recognising the pro-domain of pre-(α)pro-GDNF in CHO cells. CHO cells grown in DMEM with 10% FCS and antibiotics were plated on 6-well plates and each well was transfected with 4 μg of plasmid when grown up to approximately 80% confluence. The media were replaced with 2 ml OptiMEM medium 4 hrs after transfection. The cells and media (supernatant) were collected 48 hrs post-transfection, the media were concentrated and the samples were separated using 15% denaturating SDS-PAGE gel followed by blotting into nylon membrane and blocking with 5% milk in TBS-Tween (0.1%). GDNF was detected with either polyclonal 320/(α) pro-GDNF antibody (1:500 dilution) or polyclonal D20 antibody (Santa Cruz, 1:500 dilution) and HRP-conjugated donkey anti-rabbit immunoglobulin secondary antibody (1:2000 dilution) by using ECL method. The cells were transfected with following constructs: Lane 1 mouse pre-(α)proGDNF-pEGFP-N1; Lane 2 human pre-(α)pro-GDNF-pEGFP-N1; Lane 3 human pAAV-IRES-hrGFP-pre-(α)pro-GDNF; Lane 4 human pAAV-MCS-pre-(α)pro-GDNF; Lane 5 mouse pre-(β)pro-GDNF-pEGFP-N1; Lane 6 human pre-(β)pro-GDNF-pEGFP-N1; Lane 7 human pAAV-IRES-hrGFP-pre-(β)pro-GDNF; Lane 8 human pAAV-MCS-pre-(β)pro-GDNF; Lane 9 an empty pEGFP-N1 vector expressing GFP; Lane 10 pAAV-MCS-pre-GDNF lacking the pro region FIG. 17A; CHO cells detected with 320/(α)pro-GDNF antibody, cells.
Figure 17:
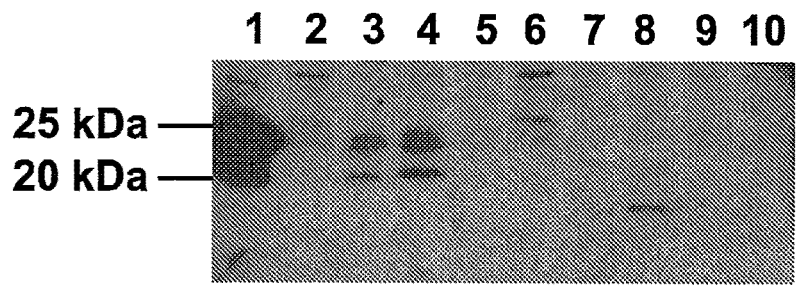
Figure 17:
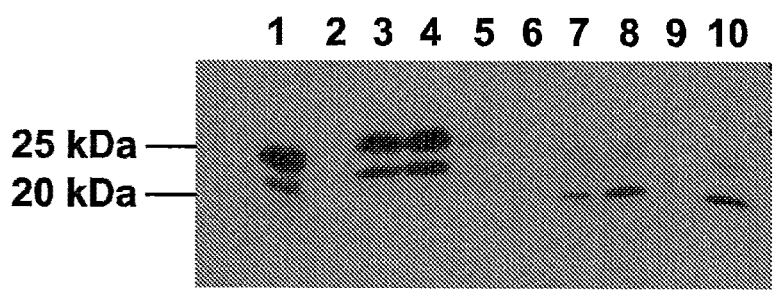
Figure 17:
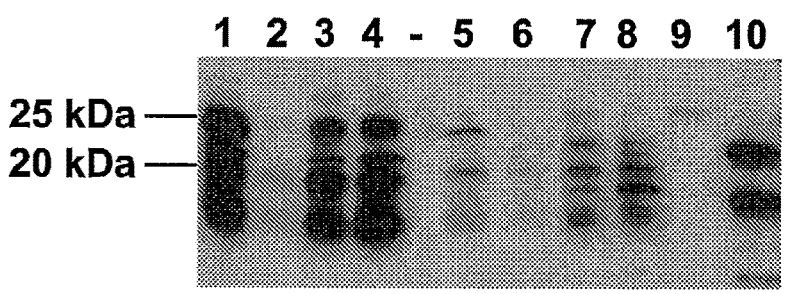

The results from Western blot analysis show that the 321/pro-GDNF antibody recognises the GDNF pro-domain of (α)pro-GDNF and (β)pro-GDNF but it does not recognise the GDNF protein lacking the pro region or recombinant GFP protein. In addition, the 321/pro-GDNF antibody recognises (α)pro-GST and (β)pro-GST fusion proteins. The anti-GDNF D20 antibody against the mature part of GDNF recognises (α)pro-GDNF, (β)pro-GDNF and GDNF protein lacking the pro region (FIG. 16). In Western blot, the 322/(α)pro-GDNF antibody recognises the GDNF pro-domain of (α)pro-GDNF but it does not recognise the (β)pro-GDNF or GDNF protein lacking the pro region. The anti-GDNF D20 antibody against the mature part of GDNF recognises (α)pro-GDNF, (β)pro-GDNF and GDNF protein lacking the pro region (FIG. 17).

Example 13

Raising an Antibody Specific to pre-(γ)pro-GDNF

A peptide comprising an amino acid sequence unique to the pre-(γ)pro-GDNF peptide is prepared according to prior known techniques as used in example 12.

Conjugation

The pure peptide is conjugated to carrier protein KLH (keyhole limpet hemocyanin), to stimulate an immune response in the subsequent immunization process. For conjugation to the peptide maleimide-activated KLH is used. The maleimide group reacts with SH-groups of cysteine, which is added to N-terminus of the peptide—only one Cys per peptide and internal Cys is avoided, to assure site-directed conjugation and unshadowed peptide for immune process. The reaction is carried out under neutral conditions and subsequently purified using dialysis. Final solution is in PBS with the concentration of 0.5 mg/ml of the conjugate. The conjugation step is controlled with Ellman test as described in Example 12 using samples collected before and after the conjugation step (peptide with and without KLH) Ellman test is made to estimate the efficiency of conjugation of sulfhydryl-containing peptide to KLH by using Ellman's reagent (5,5'-dithiobis(2-nitrobenzoic acid) or DTNB) (Walker, The Protein Protocols Handbook, 2nd edition, Humana Press inc. 2002, pp 595-596.).

Immunization

Rabbits are immunized using the following protocol: Day 0—preimmune serum and I immunization; Day 14—second immunization; Day 35—III immunization: Day 45—preliminary bleeding and ELISA testing; Day 56—IV immunization; Day 66—final bleeding and ELISA testing. First immunization is made with Freund's Complete Adjuvant (FCA), other immunizations with Freund's Incomplete Adjuvant (FIA). Freund's Adjuvants are water-in-oil emulsions, FCA containing also killed *Mycobacterium tuberculosis* and they are used to enhance immune response. The adjuvant is carefully mixed with KLH-peptide conjugate solution to 1:1 and injected subcutaneously into two sites. Blood is collected from air vain and clotted-centrifuged for serum preparation. The amount of preimmune serum is ~1 ml, preliminary serum for ELISA testing ~0.3 ml and final serum ~30 ml.

ELISA

An appropriate amount of the peptide used for immunisation is conjugated to Bovine Serum Albumin (BSA) (same procedure as for KLH conjugation). This peptide-BSA conjugate is then coated onto a high-capacity protein-binding microtiter plate (each sample in 2 reps). Subsequently, any vacant binding sites on the plate are blocked by BSA. Dilutions are then made from the preimmune, preliminary and final sera (during final ELISA) and added to the wells. The bound sample is detected using an anti-rabbit IgG antibody as a secondary antibody conjugated to Horse Radish Peroxidase (HRP), thus creating a "sandwich". As a negative control phosphate buffered saline (PBS) is used in two wells, after each step the plate is incubated and washed. Finally, colorimetric reaction with HPR occurs after adding 3,3',5,5'-tetramethylbenzidine (TMB) and optical density is measured at 450 nm with an ELISA-reader.

Antibody Purification

For IgG-purification MAbsorbent® technology is used. The purification of the antibody from the blood antiserum is carried out by binding it with the MAbsorbent A1P/A2P. MAbsorbent synthetic affinity ligand absorbent "mimics" recombinant and natural Protein A. As first part, the column is prepared according to the instructions supplied with the empty column and with the MAbsorbent. Briefly, the slurry of absorbent is mixed gently, added to the column and the column is equilibrated with binding buffer.

Then an appropriate amount of antiserum diluted in binding buffer is added to the column, incubated and let to flow through. The antibody from serum binds to MAbsorbent A1P/A2P. The column is then washed, the antibody is eluted from the affinity absorbent and collected into 2 ml fractions. After that, the column is equilibrated again for new purification. This step can be repeated, till needed amount of the antiserum is purified. Equilibration and binding are made at neutral pH, elution under acidic conditions. After collection, all fractions are dialysed against PBS and antibody concentration is measured with BCA™ protein assay technology. Finally, the antibody is in phosphate buffered saline (PBS) and stored at −20° C.

For epitope-specific affinity purification NHS-activated Sepharose® matrix technology is used. NHS-activated sepharose gives stable amide bond with antigen, at this time with peptide, which will later bind antibodies from serum. Antibodies will be eluted and collected. This method helps to purify antibodies in the serum against given peptide.

First, the column is prepared according to instructions supplied with the empty column and NHS-activated Sepharose® matrix. Briefly, NHS-activated Sepharose® matrix is put into the empty column and washed to remove the store solution. The antigen, dissolved in the coupling solution, is added to the column to be bound to the active groups of the sepharose during incubation period. Any non-reacted active groups in the medium are then blocked by standing in TRIS-buffer. Then the column is washed with two different buffers, having different pH-values, e.g. pH 8-9 for the first buffer and pH 3-4 for the second buffer.

Subsequently, the pre-prepared column is equilibrated with binding buffer and an appropriate amount of blood antiserum, diluted in PBS, is loaded into column. The slurry is kept there for some minutes to bind the antibodies with the antigens. The column is washed with binding buffer at different pH's (pH 8-6.5), then the antibodies are eluted under acid conditions and the fractions are collected by 1 ml. After collection, all fractions are dialysed against PBS and antibody concentration is measured with BCA™ protein assay technology. Finally, antibodies are in phosphate buffered saline (PBS) and stored at −20° C.

SEQUENCE LISTING FREE TEXT

SEQ ID NO:1 [223]: native human pre-gamma-pro-GDNF
SEQ ID NO:3 [223]: mouse pre-gamma-pro-GDNF
SEQ ID NO:5 [223]: human pre-gamma-pro-GDNF with ATG
SEQ ID NO:7 [223]: Primer 42
SEQ ID NO:8 [223]: Primer 43
SEQ ID NO:9 [223]: Primer 46
SEQ ID NO:10 [223]: Primer 47
SEQ ID NO:11 [223]: Primer 53
SEQ ID NO:12 [223]: Primer 49
SEQ ID NO:13 [223]: Primer 48
SEQ ID NO:14 [223]: Primer 54
SEQ ID NO:15 [223]: Human GDNF 5' primer
SEQ ID NO:16 [223]: Human GDNF 3' primer
SEQ ID NO:17 [223]: Primer 91
SEQ ID NO:18 [223]: Primer 92
SEQ ID NO:19 [223]: pre-gamma-pro aa sequence with Leu
SEQ ID NO:20 [223]: pre-gamma-pro nt sequence with CTG
SEQ ID NO:21 [223]: pre-gamma-pro aa sequence with Met
SEQ ID NO:22 [223]: pre-gamma-pro nt sequence with ATG
SEQ ID NO:23 [223]: truncated pre-gamma-pro-GDNF nt with CTG
SEQ ID NO:25 [223]: truncated pre-gamma-pro-GDNF nt with ATG
SEQ ID NO:27 [223]: V34M pre-gamma-pro-GDNF aa with Leu
SEQ ID NO:28 [223]: V34M pre-gamma-pro-GDNF nt with CTG
SEQ ID NO:29 [223]: V34M pre-gamma-pro-GDNF aa with Met
SEQ ID NO:30 [223]: V34M pre-gamma-pro-GDNF nt with ATG
SEQ ID NO:31 [223]: V38M pre-beta-pro-GDNF aa
SEQ ID NO:32 [223]: V38M pre-beta-pro-GDNF nt
SEQ ID NO:33 [223]: V64M pre-alfa-pro-GDNF aa
SEQ ID NO:34 [223]: V64M pre-alfa-pro-GDNF nt
SEQ ID NO:35 [223]: truncated pre-beta-pro-GDNF aa
SEQ ID NO:36 [223]: truncated pre-beta-pro-GD

The invention claimed is:

1. A method of treating Parkinson's disease in a human subject, said method comprising:
   administering by injection into the striatum of the brain of the subject suffering from Parkinson's disease a therapeutically effective amount of a polynucleotide encoding pre-(β)pro-GDNF protein,
   wherein the polynucleotide encoding the pre-(β)pro-GDNF protein is a polynucleotide encoding a polypeptide comprising at least one of the amino acid sequences selected from the group consisting of SEQ ID NO: 31, SEQ ID NO: 35, and SEQ ID NO: 52,
   wherein the polynucleotide is in a recombinant adeno-associated virus suitable to introduce the polynucleotide into brain cells, and
   wherein the polynucleotide is operatively linked to a cytomegalovirus promoter expression regulatory element,
   wherein the encoded pre-(β)pro-GDNF protein promotes the survival of dopaminergic neurons in Parkinson's Disease.

2. The method according to claim 1, wherein the polynucleotide encoding the pre-(β)pro-GDNF protein is selected from the group consisting of the polynucleotides as set forth in SEQ ID NO: 32, SEQ ID NO: 36 and SEQ ID NO: 51.

3. The method according to claim 1, wherein the polynucleotide encoding the pre-(β)pro-GDNF protein is a polynucleotide encoding a polypeptide selected from the group consisting of the proteins set forth in SEQ ID NO: 35 and SEQ ID NO: 52.

4. A method for promoting survival of dopamine neurons in a brain comprising:
administering a therapeutically effective amount to promote survival of dopamine neurons of a polynucleotide encoding pre-(β)pro-GDNF protein by injection into the striatum of the brain,
wherein the polynucleotide encoding the pre-(β)pro-GDNF is a polynucleotide encoding a polypeptide comprising at least one of the amino acid sequences selected from the group consisting of SEQ ID NO: 31, SEQ ID NO: 35, and SEQ ID NO: 52,
wherein the polynucleotide is operatively linked to an expression regulatory element in a recombinant adeno-associated virus suitable for introducing the polynucleotide into a neuron, and
wherein the expression regulatory element is cytomegalovirus promoter.

5. The method according to claim 4, wherein administration is to a patient afflicted with Parkinson's disease.

6. The method according to claim 4, wherein the polynucleotide encoding the pre-(β)pro-GDNF protein is selected from the group consisting of the polynucleotides as set forth in SEQ ID NO: 32, SEQ ID NO: 36 and SEQ ID NO: 51.

7. The method according to claim 4, wherein the polynucleotide encoding the pre-(β)pro-GDNF protein is a polynucleotide encoding a polypeptide selected from the group consisting of the proteins set forth in SEQ ID NO: 35 and SEQ ID NO: 52.

* * * * *

SEQUENCE LISTING

<160> NUMBER OF SEQ ID NOS: 52

<210> SEQ ID NO 1
<211> LENGTH: 546
<212> TYPE: DNA
<213> ORGANISM: Homo sapiens

```
<220> FEATURE:
<221> NAME/KEY: misc_feature
<222> LOCATION: (1)..(546)
<223> OTHER INFORMATION: native human pre-gamma-pro-GDNF
<220> FEATURE:
<221> NAME/KEY: CDS
<222> LOCATION: (1)..(543)
<220> FEATURE:
<221> NAME/KEY: misc_signal
<222> LOCATION: (1)..(141)
<220> FEATURE:
<221> NAME/KEY: mat_peptide
<222> LOCATION: (142)..(543)

<400> SEQUENCE: 1 ctg gga ctt ggg gca cct gga gtt aat gtc caa cct agg gtc tgc gga      48
Leu Gly Leu Gly Ala Pro Gly Val Asn Val Gln Pro Arg Val Cys Gly
       -45                 -40                 -35 gac ccg atc cga gca aat atg cca gag gat tat cct gat cag ttc gat      96
Asp Pro Ile Arg Ala Asn Met Pro Glu Asp Tyr Pro Asp Gln Phe Asp
   -30                 -25                 -20 gat gtc atg gat ttt att caa gcc acc att aaa aga ctg aaa agg tca     144
Asp Val Met Asp Phe Ile Gln Ala Thr Ile Lys Arg Leu Lys Arg Ser
-15                 -10                  -5                 -1  1 cca gat aaa caa atg gca gtg ctt cct aga aga gag cgg aat cgg cag     192
Pro Asp Lys Gln Met Ala Val Leu Pro Arg Arg Glu Arg Asn Arg Gln
                  5                  10                  15 gct gca gct gcc aac cca gag aat tcc aga gga aaa ggt cgg aga ggc     240
Ala Ala Ala Ala Asn Pro Glu Asn Ser Arg Gly Lys Gly Arg Arg Gly
                 20                  25                  30 cag agg ggc aaa aac cgg ggt tgt gtc tta act gca ata cat tta aat     288
Gln Arg Gly Lys Asn Arg Gly Cys Val Leu Thr Ala Ile His Leu Asn
 35                  40                  45 gtc act gac ttg ggt ctg ggc tat gaa acc aag gag gaa ctg att ttt     336
Val Thr Asp Leu Gly Leu Gly Tyr Glu Thr Lys Glu Glu Leu Ile Phe
 50                  55                  60                  65 agg tac tgc agc ggc tct tgc gat gca gct gag aca acg tac gac aaa     384
Arg Tyr Cys Ser Gly Ser Cys Asp Ala Ala Glu Thr Thr Tyr Asp Lys
                 70                  75                  80 ata ttg aaa aac tta tcc aga aat aga agg ctg gtg agt gac aaa gta     432
Ile Leu Lys Asn Leu Ser Arg Asn Arg Arg Leu Val Ser Asp Lys Val
                 85                  90                  95 ggg cag gca tgt tgc aga ccc atc gcc ttt gat gat gac ctg tcg ttt     480
Gly Gln Ala Cys Cys Arg Pro Ile Ala Phe Asp Asp Asp Leu Ser Phe
                100                 105                 110 tta gat gat aac ctg gtt tac cat att cta aga aag cat tcc gct aaa     528
Leu Asp Asp Asn Leu Val Tyr His Ile Leu Arg Lys His Ser Ala Lys
        115                 120                 125 agg tgt gga tgt atc tga                                             546
Arg Cys Gly Cys Ile
130

<210> SEQ ID NO 2
<211> LENGTH: 181
<212> TYPE: PRT
<213> ORGANISM: Homo sapiens

<400> SEQUENCE: 2

Leu Gly Leu Gly Ala Pro Gly Val Asn Val Gln Pro Arg Val Cys Gly
       -45                 -40                 -35

Asp Pro Ile Arg Ala Asn Met Pro Glu Asp Tyr Pro Asp Gln Phe Asp
   -30                 -25                 -20

Asp Val Met Asp Phe Ile Gln Ala Thr Ile Lys Arg Leu Lys Arg Ser
```

```
                -15                 -10                 -5                  -1   1
Pro Asp Lys Gln Met Ala Val Leu Pro Arg Arg Glu Arg Asn Arg Gln
            5                   10                  15

Ala Ala Ala Ala Asn Pro Glu Asn Ser Arg Gly Lys Gly Arg Arg Gly
        20                  25                  30

Gln Arg Gly Lys Asn Arg Gly Cys Val Leu Thr Ala Ile His Leu Asn
    35                  40                  45

Val Thr Asp Leu Gly Leu Gly Tyr Glu Thr Lys Glu Glu Leu Ile Phe
50                  55                  60                  65

Arg Tyr Cys Ser Gly Ser Cys Asp Ala Ala Glu Thr Thr Tyr Asp Lys
                70                  75                  80

Ile Leu Lys Asn Leu Ser Arg Asn Arg Arg Leu Val Ser Asp Lys Val
            85                  90                  95

Gly Gln Ala Cys Cys Arg Pro Ile Ala Phe Asp Asp Leu Ser Phe
        100                 105                 110

Leu Asp Asp Asn Leu Val Tyr His Ile Leu Arg Lys His Ser Ala Lys
    115                 120                 125

Arg Cys Gly Cys Ile
130

<210> SEQ ID NO 3
<211> LENGTH: 546
<212> TYPE: DNA
<213> ORGANISM: Mus musculus
<220> FEATURE:
<221> NAME/KEY: misc_feature
<222> LOCATION: (1)..(546)
<223> OTHER INFORMATION: mouse pre-gamma-pro-GDNF
<220> FEATURE:
<221> NAME/KEY: CDS
<222> LOCATION: (1)..(543)
<220> FEATURE:
<221> NAME/KEY: misc_signal
<222> LOCATION: (1)..(141)
<220> FEATURE:
<221> NAME/KEY: mat_peptide
<222> LOCATION: (142)..(543)

<400> SEQUENCE: 3 atg gga ttc ggg cca ctt gga gtt aat gtc caa ctg ggg gtc tac gga      48
Met Gly Phe Gly Pro Leu Gly Val Asn Val Gln Leu Gly Val Tyr Gly
            -45                 -40                 -35 gac cgg atc cga gcc aat atg cct gaa gat tat cct gac cag ttt gat      96
Asp Arg Ile Arg Ala Asn Met Pro Glu Asp Tyr Pro Asp Gln Phe Asp
        -30                 -25                 -20 gac gtc atg gat ttt att caa gcc acc att aaa aga ctg aaa agg tca     144
Asp Val Met Asp Phe Ile Gln Ala Thr Ile Lys Arg Leu Lys Arg Ser
-15                 -10                 -5                  -1   1 cca gat aaa caa gcg gca gcg ctt cct cga aga gag agg aat cgg cag     192
Pro Asp Lys Gln Ala Ala Ala Leu Pro Arg Arg Glu Arg Asn Arg Gln
            5                   10                  15 gct gca gct gcc agc cca gag aat tcc aga ggg aaa ggt cgc aga ggc     240
Ala Ala Ala Ala Ser Pro Glu Asn Ser Arg Gly Lys Gly Arg Arg Gly
        20                  25                  30 cag agg ggc aaa aat cgg ggg tgc gtt tta act gcc ata cac tta aat     288
Gln Arg Gly Lys Asn Arg Gly Cys Val Leu Thr Ala Ile His Leu Asn
    35                  40                  45 gtc act gac ttg ggt ttg ggc tat gaa acc aag gag gaa ctg atc ttt     336
Val Thr Asp Leu Gly Leu Gly Tyr Glu Thr Lys Glu Glu Leu Ile Phe
50                  55                  60                  65 cga tat tgc agc ggt tcc tgt gaa tcg gcc gag aca atg tat gac aaa     384
```

```
Arg Tyr Cys Ser Gly Ser Cys Glu Ser Ala Glu Thr Met Tyr Asp Lys
                70                  75                  80 ata cta aaa aac ctg tct cgg agt aga agg cta aca agt gac aaa gta       432
Ile Leu Lys Asn Leu Ser Arg Ser Arg Arg Leu Thr Ser Asp Lys Val
            85                  90                  95 ggc cag gca tgt tgc agg ccg gtc gcc ttc gac gac gac ctg tcg ttt       480
Gly Gln Ala Cys Cys Arg Pro Val Ala Phe Asp Asp Asp Leu Ser Phe
            100                 105                 110 tta gat gac aac ctg gtt tac cat att cta aga aag cat tcc gct aaa       528
Leu Asp Asp Asn Leu Val Tyr His Ile Leu Arg Lys His Ser Ala Lys
            115                 120                 125 cgg tgt gga tgt atc tga                                               546
Arg Cys Gly Cys Ile
130
```

```
<210> SEQ ID NO 4
<211> LENGTH: 181
<212> TYPE: PRT
<213> ORGANISM: Mus musculus

<400> SEQUENCE: 4

Met Gly Phe Gly Pro Leu Gly Val Asn Val Gln Leu Gly Val Tyr Gly
    -45                 -40                 -35

Asp Arg Ile Arg Ala Asn Met Pro Glu Asp Tyr Pro Asp Gln Phe Asp
        -30                 -25                 -20

Asp Val Met Asp Phe Ile Gln Ala Thr Ile Lys Arg Leu Lys Arg Ser
-15                 -10                  -5                  -1   1

Pro Asp Lys Gln Ala Ala Ala Leu Pro Arg Arg Glu Arg Asn Arg Gln
            5                   10                  15

Ala Ala Ala Ser Pro Glu Asn Ser Arg Gly Lys Gly Arg Arg Gly
            20                  25                  30

Gln Arg Gly Lys Asn Arg Gly Cys Val Leu Thr Ala Ile His Leu Asn
        35                  40                  45

Val Thr Asp Leu Gly Leu Gly Tyr Glu Thr Lys Glu Glu Leu Ile Phe
50                  55                  60                  65

Arg Tyr Cys Ser Gly Ser Cys Glu Ser Ala Glu Thr Met Tyr Asp Lys
                70                  75                  80

Ile Leu Lys Asn Leu Ser Arg Ser Arg Arg Leu Thr Ser Asp Lys Val
            85                  90                  95

Gly Gln Ala Cys Cys Arg Pro Val Ala Phe Asp Asp Asp Leu Ser Phe
            100                 105                 110

Leu Asp Asp Asn Leu Val Tyr His Ile Leu Arg Lys His Ser Ala Lys
            115                 120                 125

Arg Cys Gly Cys Ile
130
```

```
<210> SEQ ID NO 5
<211> LENGTH: 546
<212> TYPE: DNA
<213> ORGANISM: Homo sapiens
<220> FEATURE:
<221> NAME/KEY: CDS
<222> LOCATION: (1)..(543)
<220> FEATURE:
<221> NAME/KEY: misc_feature
<222> LOCATION: (1)..(546)
<223> OTHER INFORMATION: human pre-gamma-pro-GDNF with ATG
<220> FEATURE:
<221> NAME/KEY: misc_signal
<222> LOCATION: (1)..(141)
<220> FEATURE:
```

```
<221> NAME/KEY: mat_peptide
<222> LOCATION: (142)..(543)

<400> SEQUENCE: 5 atg gga ctt ggg gca cct gga gtt aat gtc caa cct agg gtc tgc gga      48
Met Gly Leu Gly Ala Pro Gly Val Asn Val Gln Pro Arg Val Cys Gly
        -45                 -40                 -35 gac ccg atc cga gca aat atg cca gag gat tat cct gat cag ttc gat      96
Asp Pro Ile Arg Ala Asn Met Pro Glu Asp Tyr Pro Asp Gln Phe Asp
    -30                 -25                 -20 gat gtc atg gat ttt att caa gcc acc att aaa aga ctg aaa agg tca     144
Asp Val Met Asp Phe Ile Gln Ala Thr Ile Lys Arg Leu Lys Arg Ser
-15                 -10                  -5                 -1  1 cca gat aaa caa atg gca gtg ctt cct aga aga gag cgg aat cgg cag     192
Pro Asp Lys Gln Met Ala Val Leu Pro Arg Arg Glu Arg Asn Arg Gln
                 5                  10                  15 gct gca gct gcc aac cca gag aat tcc aga gga aaa ggt cgg aga ggc     240
Ala Ala Ala Ala Asn Pro Glu Asn Ser Arg Gly Lys Gly Arg Arg Gly
                20                  25                  30 cag agg ggc aaa aac cgg ggt tgt gtc tta act gca ata cat tta aat     288
Gln Arg Gly Lys Asn Arg Gly Cys Val Leu Thr Ala Ile His Leu Asn
    35                  40                  45 gtc act gac ttg ggt ctg ggc tat gaa acc aag gag gaa ctg att ttt     336
Val Thr Asp Leu Gly Leu Gly Tyr Glu Thr Lys Glu Glu Leu Ile Phe
50                   55                  60                  65 agg tac tgc agc ggc tct tgc gat gca gct gag aca acg tac gac aaa     384
Arg Tyr Cys Ser Gly Ser Cys Asp Ala Ala Glu Thr Thr Tyr Asp Lys
70                   75                  80 ata ttg aaa aac tta tcc aga aat aga agg ctg gtg agt gac aaa gta     432
Ile Leu Lys Asn Leu Ser Arg Asn Arg Arg Leu Val Ser Asp Lys Val
                85                  90                  95 ggg cag gca tgt tgc aga ccc atc gcc ttt gat gat gac ctg tcg ttt     480
Gly Gln Ala Cys Cys Arg Pro Ile Ala Phe Asp Asp Asp Leu Ser Phe
                100                 105                 110 tta gat gat aac ctg gtt tac cat att cta aga aag cat tcc gct aaa     528
Leu Asp Asp Asn Leu Val Tyr His Ile Leu Arg Lys His Ser Ala Lys
                115                 120                 125 agg tgt gga tgt atc tga                                              546
Arg Cys Gly Cys Ile
    130

<210> SEQ ID NO 6
<211> LENGTH: 181
<212> TYPE: PRT
<213> ORGANISM: Homo sapiens

<400> SEQUENCE: 6

Met Gly Leu Gly Ala Pro Gly Val Asn Val Gln Pro Arg Val Cys Gly
        -45                 -40                 -35

Asp Pro Ile Arg Ala Asn Met Pro Glu Asp Tyr Pro Asp Gln Phe Asp
    -30                 -25                 -20

Asp Val Met Asp Phe Ile Gln Ala Thr Ile Lys Arg Leu Lys Arg Ser
-15                 -10                  -5                 -1  1

Pro Asp Lys Gln Met Ala Val Leu Pro Arg Arg Glu Arg Asn Arg Gln
                 5                  10                  15

Ala Ala Ala Ala Asn Pro Glu Asn Ser Arg Gly Lys Gly Arg Arg Gly
                20                  25                  30

Gln Arg Gly Lys Asn Arg Gly Cys Val Leu Thr Ala Ile His Leu Asn
    35                  40                  45
```

```
Val Thr Asp Leu Gly Leu Gly Tyr Glu Thr Lys Glu Glu Leu Ile Phe
 50                  55                  60                  65

Arg Tyr Cys Ser Gly Ser Cys Asp Ala Ala Glu Thr Thr Tyr Asp Lys
                 70                  75                  80

Ile Leu Lys Asn Leu Ser Arg Asn Arg Arg Leu Val Ser Asp Lys Val
             85                  90                  95

Gly Gln Ala Cys Cys Arg Pro Ile Ala Phe Asp Asp Leu Ser Phe
            100                 105                 110

Leu Asp Asp Asn Leu Val Tyr His Ile Leu Arg Lys His Ser Ala Lys
        115                 120                 125

Arg Cys Gly Cys Ile
130

<210> SEQ ID NO 7
<211> LENGTH: 16
<212> TYPE: DNA
<213> ORGANISM: Artificial sequence
<220> FEATURE:
<223> OTHER INFORMATION: Primer 42

<400> SEQUENCE: 7
gctcctgccc gaggtc                                                             16

<210> SEQ ID NO 8
<211> LENGTH: 21
<212> TYPE: DNA
<213> ORGANISM: Artificial sequence
<220> FEATURE:
<223> OTHER INFORMATION: Primer 43

<400> SEQUENCE: 8
cctttcttcg cactgtagca g                                                       21

<210> SEQ ID NO 9
<211> LENGTH: 19
<212> TYPE: DNA
<213> ORGANISM: Artificial sequence
<220> FEATURE:
<223> OTHER INFORMATION: Primer 46

<400> SEQUENCE: 9
gtccggatgg gtctcctgg                                                          19

<210> SEQ ID NO 10
<211> LENGTH: 20
<212> TYPE: DNA
<213> ORGANISM: Artificial sequence
<220> FEATURE:
<223> OTHER INFORMATION: Primer 47

<400> SEQUENCE: 10
cacagcagtc tctggagccg                                                         20

<210> SEQ ID NO 11
<211> LENGTH: 19
<212> TYPE: DNA
<213> ORGANISM: Artificial sequence
<220> FEATURE:
<223> OTHER INFORMATION: Primer 53

<400> SEQUENCE: 11
gacctgttgg gcggggctc                                                          19
```

```
<210> SEQ ID NO 12
<211> LENGTH: 22
<212> TYPE: DNA
<213> ORGANISM: Artificial sequence
<220> FEATURE:
<223> OTHER INFORMATION: Primer 49

<400> SEQUENCE: 12
cctgggaacc ttggtccctt tc                                              22

<210> SEQ ID NO 13
<211> LENGTH: 19
<212> TYPE: DNA
<213> ORGANISM: Artificial sequence
<220> FEATURE:
<223> OTHER INFORMATION: Primer 48

<400> SEQUENCE: 13
gctccagcca tcagcccgg                                                  19

<210> SEQ ID NO 14
<211> LENGTH: 21
<212> TYPE: DNA
<213> ORGANISM: Artificial sequence
<220> FEATURE:
<223> OTHER INFORMATION: Primer 54

<400> SEQUENCE: 14
cacagcagtc tctggagccg g                                               21

<210> SEQ ID NO 15
<211> LENGTH: 19
<212> TYPE: DNA
<213> ORGANISM: Artificial sequence
<220> FEATURE:
<223> OTHER INFORMATION: Human GDNF 5' primer

<400> SEQUENCE: 15
gctccagcca tcagcccgg                                                  19

<210> SEQ ID NO 16
<211> LENGTH: 21
<212> TYPE: DNA
<213> ORGANISM: Artificial sequence
<220> FEATURE:
<223> OTHER INFORMATION: Human GDNF 3' primer

<400> SEQUENCE: 16
cacagcagtc tctggagccg g                                               21

<210> SEQ ID NO 17
<211> LENGTH: 40
<212> TYPE: DNA
<213> ORGANISM: Artificial sequence
<220> FEATURE:
<223> OTHER INFORMATION: Primer 91

<400> SEQUENCE: 17
caacaaggat ccatgggact tggggcacct ggagttaatg                           40

<210> SEQ ID NO 18
<211> LENGTH: 38
<212> TYPE: DNA
<213> ORGANISM: Artificial sequence
<220> FEATURE:
<223> OTHER INFORMATION: Primer 92
```

<400> SEQUENCE: 18
ccaccactcg agtcagatac atccacacct tttagcgg                                   38

<210> SEQ ID NO 19
<211> LENGTH: 47
<212> TYPE: PRT
<213> ORGANISM: Homo sapiens
<220> FEATURE:
<221> NAME/KEY: MISC_FEATURE
<222> LOCATION: (1)..(47)
<223> OTHER INFORMATION: pre-gamma-pro aa sequence with Leu

<400> SEQUENCE: 19

Leu Gly Leu Gly Ala Pro Gly Val Asn Val Gln Pro Arg Val Cys Gly
1               5                   10                  15

Asp Pro Ile Arg Ala Asn Met Pro Glu Asp Tyr Pro Asp Gln Phe Asp
            20                  25                  30

Asp Val Met Asp Phe Ile Gln Ala Thr Ile Lys Arg Leu Lys Arg
        35                  40                  45

<210> SEQ ID NO 20
<211> LENGTH: 141
<212> TYPE: DNA
<213> ORGANISM: Homo sapiens
<220> FEATURE:
<221> NAME/KEY: misc_feature
<222> LOCATION: (1)..(141)
<223> OTHER INFORMATION: pre-gamma-pro nt sequence with CTG

<400> SEQUENCE: 20
ctgggacttg gggcacctgg agttaatgtc caacctaggg tctgcggaga cccgatccga    60
gcaaatatgc cagaggatta tcctgatcag ttcgatgatg tcatggattt tattcaagcc   120
accattaaaa gactgaaaag g                                             141

<210> SEQ ID NO 21
<211> LENGTH: 47
<212> TYPE: PRT
<213> ORGANISM: Homo sapiens
<220> FEATURE:
<221> NAME/KEY: MISC_FEATURE
<222> LOCATION: (1)..(47)
<223> OTHER INFORMATION: pre-gamma-pro aa sequence with Met

<400> SEQUENCE: 21

Met Gly Leu Gly Ala Pro Gly Val Asn Val Gln Pro Arg Val Cys Gly
1               5                   10                  15

Asp Pro Ile Arg Ala Asn Met Pro Glu Asp Tyr Pro Asp Gln Phe Asp
            20                  25                  30

Asp Val Met Asp Phe Ile Gln Ala Thr Ile Lys Arg Leu Lys Arg
        35                  40                  45

<210> SEQ ID NO 22
<211> LENGTH: 141
<212> TYPE: DNA
<213> ORGANISM: Homo sapiens
<220> FEATURE:
<221> NAME/KEY: misc_feature
<222> LOCATION: (1)..(141)
<223> OTHER INFORMATION: pre-gamma-pro nt sequence with ATG

<400> SEQUENCE: 22
atgggacttg gggcacctgg agttaatgtc caacctaggg tctgcggaga cccgatccga    60
gcaaatatgc cagaggatta tcctgatcag ttcgatgatg tcatggattt tattcaagcc   120

-continued

```
accattaaaa gactgaaaag g                                             141
```

<210> SEQ ID NO 23
<211> LENGTH: 432
<212> TYPE: DNA
<213> ORGANISM: Homo sapiens
<220> FEATURE:
<221> NAME/KEY: CDS
<222> LOCATION: (1)..(429)
<220> FEATURE:
<221> NAME/KEY: misc_feature
<222> LOCATION: (1)..(432)
<223> OTHER INFORMATION: truncated pre-gamma-pro-GDNF nt with CTG
<220> FEATURE:
<221> NAME/KEY: misc_signal
<222> LOCATION: (1)..(141)
<220> FEATURE:
<221> NAME/KEY: mat_peptide
<222> LOCATION: (142)..(429)

<400> SEQUENCE: 23

```
ctg gga ctt ggg gca cct gga gtt aat gtc caa cct agg gtc tgc gga     48
Leu Gly Leu Gly Ala Pro Gly Val Asn Val Gln Pro Arg Val Cys Gly
    -45                 -40                 -35 gac ccg atc cga gca aat atg cca gag gat tat cct gat cag ttc gat     96
Asp Pro Ile Arg Ala Asn Met Pro Glu Asp Tyr Pro Asp Gln Phe Asp
-30                 -25                 -20 gat gtc atg gat ttt att caa gcc acc att aaa aga ctg aaa agg cgg    144
Asp Val Met Asp Phe Ile Gln Ala Thr Ile Lys Arg Leu Lys Arg Arg
-15                 -10                 -5              -1  1 ggt tgt gtc tta act gca ata cat tta aat gtc act gac ttg ggt ctg    192
Gly Cys Val Leu Thr Ala Ile His Leu Asn Val Thr Asp Leu Gly Leu
            5                   10                  15 ggc tat gaa acc aag gag gaa ctg att ttt agg tac tgc agc ggc tct    240
Gly Tyr Glu Thr Lys Glu Glu Leu Ile Phe Arg Tyr Cys Ser Gly Ser
        20                  25                  30 tgc gat gca gct gag aca acg tac gac aaa ata ttg aaa aac tta tcc    288
Cys Asp Ala Ala Glu Thr Thr Tyr Asp Lys Ile Leu Lys Asn Leu Ser
    35                  40                  45 aga aat aga agg ctg gtg agt gac aaa gta ggg cag gca tgt tgc aga    336
Arg Asn Arg Arg Leu Val Ser Asp Lys Val Gly Gln Ala Cys Cys Arg
50                  55                  60                  65 ccc atc gcc ttt gat gat gac ctg tcg ttt tta gat gat aac ctg gtt    384
Pro Ile Ala Phe Asp Asp Asp Leu Ser Phe Leu Asp Asp Asn Leu Val
                70                  75                  80 tac cat att cta aga aag cat tcc gct aaa agg tgt gga tgt atc tga    432
Tyr His Ile Leu Arg Lys His Ser Ala Lys Arg Cys Gly Cys Ile
            85                  90                  95
```

<210> SEQ ID NO 24
<211> LENGTH: 143
<212> TYPE: PRT
<213> ORGANISM: Homo sapiens

<400> SEQUENCE: 24

```
Leu Gly Leu Gly Ala Pro Gly Val Asn Val Gln Pro Arg Val Cys Gly
    -45                 -40                 -35

Asp Pro Ile Arg Ala Asn Met Pro Glu Asp Tyr Pro Asp Gln Phe Asp
-30                 -25                 -20

Asp Val Met Asp Phe Ile Gln Ala Thr Ile Lys Arg Leu Lys Arg Arg
-15                 -10                 -5              -1  1

Gly Cys Val Leu Thr Ala Ile His Leu Asn Val Thr Asp Leu Gly Leu
            5                   10                  15
```

```
Gly Tyr Glu Thr Lys Glu Glu Leu Ile Phe Arg Tyr Cys Ser Gly Ser
            20                  25                  30

Cys Asp Ala Ala Glu Thr Thr Tyr Asp Lys Ile Leu Lys Asn Leu Ser
 35                  40                  45

Arg Asn Arg Arg Leu Val Ser Asp Lys Val Gly Gln Ala Cys Cys Arg
 50                  55                  60                  65

Pro Ile Ala Phe Asp Asp Asp Leu Ser Phe Leu Asp Asp Asn Leu Val
                 70                  75                  80

Tyr His Ile Leu Arg Lys His Ser Ala Lys Arg Cys Gly Cys Ile
             85                  90                  95

<210> SEQ ID NO 25
<211> LENGTH: 432
<212> TYPE: DNA
<213> ORGANISM: Homo sapiens
<220> FEATURE:
<221> NAME/KEY: CDS
<222> LOCATION: (1)..(429)
<220> FEATURE:
<221> NAME/KEY: misc_feature
<222> LOCATION: (1)..(432)
<223> OTHER INFORMATION: truncated pre-gamma-pro-GDNF nt with ATG
<220> FEATURE:
<221> NAME/KEY: misc_signal
<222> LOCATION: (1)..(141)
<220> FEATURE:
<221> NAME/KEY: mat_peptide
<222> LOCATION: (142)..(429)

<400> SEQUENCE: 25 atg gga ctt ggg gca cct gga gtt aat gtc caa cct agg gtc tgc gga      48
Met Gly Leu Gly Ala Pro Gly Val Asn Val Gln Pro Arg Val Cys Gly
            -45                 -40                 -35 gac ccg atc cga gca aat atg cca gag gat tat cct gat cag ttc gat      96
Asp Pro Ile Arg Ala Asn Met Pro Glu Asp Tyr Pro Asp Gln Phe Asp
        -30                 -25                 -20 gat gtc atg gat ttt att caa gcc acc att aaa aga ctg aaa agg cgg     144
Asp Val Met Asp Phe Ile Gln Ala Thr Ile Lys Arg Leu Lys Arg Arg
    -15                 -10                  -5                 -1   1 ggt tgt gtc tta act gca ata cat tta aat gtc act gac ttg ggt ctg     192
Gly Cys Val Leu Thr Ala Ile His Leu Asn Val Thr Asp Leu Gly Leu
                  5                  10                  15 ggc tat gaa acc aag gag gaa ctg att ttt agg tac tgc agc ggc tct     240
Gly Tyr Glu Thr Lys Glu Glu Leu Ile Phe Arg Tyr Cys Ser Gly Ser
            20                  25                  30 tgc gat gca gct gag aca acg tac gac aaa ata ttg aaa aac tta tcc     288
Cys Asp Ala Ala Glu Thr Thr Tyr Asp Lys Ile Leu Lys Asn Leu Ser
 35                  40                  45 aga aat aga agg ctg gtg agt gac aaa gta ggg cag gca tgt tgc aga     336
Arg Asn Arg Arg Leu Val Ser Asp Lys Val Gly Gln Ala Cys Cys Arg
 50                  55                  60                  65 ccc atc gcc ttt gat gat gac ctg tcg ttt tta gat gat aac ctg gtt     384
Pro Ile Ala Phe Asp Asp Asp Leu Ser Phe Leu Asp Asp Asn Leu Val
                 70                  75                  80 tac cat att cta aga aag cat tcc gct aaa agg tgt gga tgt atc tga     432
Tyr His Ile Leu Arg Lys His Ser Ala Lys Arg Cys Gly Cys Ile
             85                  90                  95

<210> SEQ ID NO 26
<211> LENGTH: 143
<212> TYPE: PRT
<213> ORGANISM: Homo sapiens
```

```
<400> SEQUENCE: 26

Met Gly Leu Gly Ala Pro Gly Val Asn Val Gln Pro Arg Val Cys Gly
        -45                 -40                 -35
Asp Pro Ile Arg Ala Asn Met Pro Glu Asp Tyr Pro Asp Gln Phe Asp
        -30                 -25                 -20
Asp Val Met Asp Phe Ile Gln Ala Thr Ile Lys Arg Leu Lys Arg Arg
        -15                 -10                  -5             -1  1
Gly Cys Val Leu Thr Ala Ile His Leu Asn Val Thr Asp Leu Gly Leu
                  5                  10                  15
Gly Tyr Glu Thr Lys Glu Leu Ile Phe Arg Tyr Cys Ser Gly Ser
                 20                  25                  30
Cys Asp Ala Ala Glu Thr Thr Tyr Asp Lys Ile Leu Lys Asn Leu Ser
         35                  40                  45
Arg Asn Arg Arg Leu Val Ser Asp Lys Val Gly Gln Ala Cys Cys Arg
 50                  55                  60                  65
Pro Ile Ala Phe Asp Asp Leu Ser Phe Leu Asp Asp Asn Leu Val
                 70                  75                  80
Tyr His Ile Leu Arg Lys His Ser Ala Lys Arg Cys Gly Cys Ile
         85                  90                  95

<210> SEQ ID NO 27
<211> LENGTH: 181
<212> TYPE: PRT
<213> ORGANISM: Homo sapiens
<220> FEATURE:
<221> NAME/KEY: MISC_FEATURE
<222> LOCATION: (1)..(181)
<223> OTHER INFORMATION: V34M pre-gamma-pro-GDNF aa with Leu

<400> SEQUENCE: 27

Leu Gly Leu Gly Ala Pro Gly Val Asn Val Gln Pro Arg Val Cys Gly
 1               5                  10                  15
Asp Pro Ile Arg Ala Asn Met Pro Glu Asp Tyr Pro Asp Gln Phe Asp
                20                  25                  30
Asp Met Met Asp Phe Ile Gln Ala Thr Ile Lys Arg Leu Lys Arg Ser
         35                  40                  45
Pro Asp Lys Gln Met Ala Val Leu Pro Arg Arg Glu Arg Asn Arg Gln
 50                  55                  60
Ala Ala Ala Ala Asn Pro Glu Asn Ser Arg Gly Lys Gly Arg Arg Gly
 65                  70                  75                  80
Gln Arg Gly Lys Asn Arg Gly Cys Val Leu Thr Ala Ile His Leu Asn
                 85                  90                  95
Val Thr Asp Leu Gly Leu Gly Tyr Glu Thr Lys Glu Leu Ile Phe
                100                 105                 110
Arg Tyr Cys Ser Gly Ser Cys Asp Ala Ala Glu Thr Thr Tyr Asp Lys
            115                 120                 125
Ile Leu Lys Asn Leu Ser Arg Asn Arg Arg Leu Val Ser Asp Lys Val
        130                 135                 140
Gly Gln Ala Cys Cys Arg Pro Ile Ala Phe Asp Asp Leu Ser Phe
145                 150                 155                 160
Leu Asp Asp Asn Leu Val Tyr His Ile Leu Arg Lys His Ser Ala Lys
                165                 170                 175
Arg Cys Gly Cys Ile
            180

<210> SEQ ID NO 28
```

```
<211> LENGTH: 546
<212> TYPE: DNA
<213> ORGANISM: Homo sapiens
<220> FEATURE:
<221> NAME/KEY: misc_feature
<222> LOCATION: (1)..(546)
<223> OTHER INFORMATION: V34M pre-gamma-pro-GDNF nt with CTG

<400> SEQUENCE: 28
ctgggacttg gggcacctgg agttaatgtc caacctaggg tctgcggaga cccgatccga      60
gcaaatatgc cagaggatta tcctgatcag ttcgatgata tgatggattt tattcaagcc     120
accattaaaa gactgaaaag gtcaccagat aaacaaatgg cagtgcttcc tagaagagag     180
cggaatcggc aggctgcagc tgccaaccca gagaattcca gaggaaaagg tcggagaggc     240
cagaggggca aaaccggggg ttgtgtctta actgcaatac atttaaatgt cactgacttg     300
ggtctgggct atgaaaccaa ggaggaactg attttaggt actgcagcgg ctcttgcgat      360
gcagctgaga caacgtacga caaaatattg aaaaacttat ccagaaatag aaggctggtg     420
agtgacaaag tagggcaggc atgttgcaga cccatcgcct tgatgatga cctgtcgttt      480 ttagatgata acctggttta ccatattcta agaaagcatt ccgctaaaag gtgtggatgt     540
atctga                                                                546

<210> SEQ ID NO 29
<211> LENGTH: 181
<212> TYPE: PRT
<213> ORGANISM: Homo sapiens
<220> FEATURE:
<221> NAME/KEY: MISC_FEATURE
<223> OTHER INFORMATION: V34M pre-gamma-pro-GDNF aa with Met

<400> SEQUENCE: 29

Met Gly Leu Gly Ala Pro Gly Val Asn Val Gln Pro Arg Val Cys Gly
1               5                   10                  15

Asp Pro Ile Arg Ala Asn Met Pro Glu Asp Tyr Pro Asp Gln Phe Asp
            20                  25                  30

Asp Met Met Asp Phe Ile Gln Ala Thr Ile Lys Arg Leu Lys Arg Ser
        35                  40                  45

Pro Asp Lys Gln Met Ala Val Leu Pro Arg Arg Glu Arg Asn Arg Gln
    50                  55                  60

Ala Ala Ala Ala Asn Pro Glu Asn Ser Arg Gly Lys Gly Arg Arg Gly
65                  70                  75                  80

Gln Arg Gly Lys Asn Arg Gly Cys Val Leu Thr Ala Ile His Leu Asn
                85                  90                  95

Val Thr Asp Leu Gly Leu Gly Tyr Glu Thr Lys Glu Glu Leu Ile Phe
            100                 105                 110

Arg Tyr Cys Ser Gly Ser Cys Asp Ala Ala Glu Thr Thr Tyr Asp Lys
        115                 120                 125

Ile Leu Lys Asn Leu Ser Arg Asn Arg Arg Leu Val Ser Asp Lys Val
    130                 135                 140

Gly Gln Ala Cys Cys Arg Pro Ile Ala Phe Asp Asp Leu Ser Phe
145                 150                 155                 160

Leu Asp Asp Asn Leu Val Tyr His Ile Leu Arg Lys His Ser Ala Lys
                165                 170                 175

Arg Cys Gly Cys Ile
            180

<210> SEQ ID NO 30
```

```
<211> LENGTH: 546
<212> TYPE: DNA
<213> ORGANISM: Homo sapiens
<220> FEATURE:
<221> NAME/KEY: misc_feature
<222> LOCATION: (1)..(546)
<223> OTHER INFORMATION: V34M pre-gamma-pro-GDNF nt with ATG

<400> SEQUENCE: 30
atgggacttg gggcacctgg agttaatgtc aacctaggg tctgcggaga cccgatccga      60
gcaaatatgc cagaggatta tcctgatcag ttcgatgata tgatggattt tattcaagcc    120
accattaaaa gactgaaaag gtcaccagat aaacaaatgg cagtgcttcc tagaagagag    180
cggaatcggc aggctgcagc tgccaaccca gagaattcca gaggaaaagg tcggagaggc    240
cagaggggca aaaccggggg ttgtgtctta actgcaatac atttaaatgt cactgacttg    300
ggtctgggct atgaaaccaa ggaggaactg atttttaggt actgcagcgg ctcttgcgat    360
gcagctgaga acgtacga caaaatattg aaaacttat ccagaaatag aaggctggtg       420
agtgacaaag tagggcaggc atgttgcaga cccatcgcct ttgatgatga cctgtcgttt    480
ttagatgata acctggttta ccatattcta agaaagcatt ccgctaaaag gtgtggatgt    540
atctga                                                              546

<210> SEQ ID NO 31
<211> LENGTH: 185
<212> TYPE: PRT
<213> ORGANISM: Homo sapiens
<220> FEATURE:
<221> NAME/KEY: MISC_FEATURE
<222> LOCATION: (1)..(185)
<223> OTHER INFORMATION: V38M pre-beta-pro-GDNF aa

<400> SEQUENCE: 31

Met Lys Leu Trp Asp Val Val Ala Val Cys Leu Val Leu Leu His Thr
 1               5                  10                  15

Ala Ser Ala Phe Pro Leu Pro Ala Ala Asn Met Pro Glu Asp Tyr Pro
            20                  25                  30

Asp Gln Phe Asp Asp Met Met Asp Phe Ile Gln Ala Thr Ile Lys Arg
        35                  40                  45

Leu Lys Arg Ser Pro Asp Lys Gln Met Ala Val Leu Pro Arg Arg Glu
    50                  55                  60

Arg Asn Arg Gln Ala Ala Ala Ala Asn Pro Glu Asn Ser Arg Gly Lys
65                  70                  75                  80

Gly Arg Arg Gly Gln Arg Gly Lys Asn Arg Gly Cys Val Leu Thr Ala
                85                  90                  95

Ile His Leu Asn Val Thr Asp Leu Gly Leu Gly Tyr Glu Thr Lys Glu
            100                 105                 110

Glu Leu Ile Phe Arg Tyr Cys Ser Gly Ser Cys Asp Ala Ala Glu Thr
        115                 120                 125

Thr Tyr Asp Lys Ile Leu Lys Asn Leu Ser Arg Asn Arg Arg Leu Val
    130                 135                 140

Ser Asp Lys Val Gly Gln Ala Cys Cys Arg Pro Ile Ala Phe Asp Asp
145                 150                 155                 160

Asp Leu Ser Phe Leu Asp Asp Asn Leu Val Tyr His Ile Leu Arg Lys
                165                 170                 175

His Ser Ala Lys Arg Cys Gly Cys Ile
            180                 185
```

-continued

<210> SEQ ID NO 32
<211> LENGTH: 558
<212> TYPE: DNA
<213> ORGANISM: Homo sapiens
<220> FEATURE:
<221> NAME/KEY: misc_feature
<222> LOCATION: (1)..(558)
<223> OTHER INFORMATION: V38M pre-beta-pro-GDNF nt

<400> SEQUENCE: 32

```
atgaagttat gggatgtcgt ggctgtctgc ctggtgctgc tccacaccgc gtccgccttc      60
ccgctgcccg ccgcaaatat gccagaggat tatcctgatc agttcgatga tatgatggat     120
tttattcaag ccaccattaa agactgaaa aggtcaccag ataaacaaat ggcagtgctt     180
cctagaagag agcggaatcg gcaggctgca gctgccaacc cagagaattc cagaggaaaa     240
ggtcggagag ccagaggggg caaaaaccgg ggttgtgtct taactgcaat acatttaaat     300
gtcactgact tgggtctggg ctatgaaacc aaggaggaac tgattttag gtactgcagc     360
ggctcttgcg atgcagctga acaacgtac gacaaaatat tgaaaactt atccagaaat     420
agaaggctgg tgagtgacaa agtagggcag gcatgttgca gacccatcgc ctttgatgat     480
gacctgtcgt ttttagatga taacctggtt taccatattc taagaaagca ttccgctaaa     540
aggtgtggat gtatctga                                                   558
```

<210> SEQ ID NO 33
<211> LENGTH: 211
<212> TYPE: PRT
<213> ORGANISM: Homo sapiens
<220> FEATURE:
<221> NAME/KEY: MISC_FEATURE
<222> LOCATION: (1)..(211)
<223> OTHER INFORMATION: V64M pre-alfa-pro-GDNF aa

<400> SEQUENCE: 33

```
Met Lys Leu Trp Asp Val Val Ala Val Cys Leu Val Leu His Thr
1               5                   10                  15

Ala Ser Ala Phe Pro Leu Pro Ala Gly Lys Arg Pro Pro Glu Ala Pro
            20                  25                  30

Ala Glu Asp Arg Ser Leu Gly Arg Arg Arg Ala Pro Phe Ala Leu Ser
        35                  40                  45

Ser Asp Ser Asn Met Pro Glu Asp Tyr Pro Asp Gln Phe Asp Asp Met
    50                  55                  60

Met Asp Phe Ile Gln Ala Thr Ile Lys Arg Leu Lys Arg Ser Pro Asp
65                  70                  75                  80

Lys Gln Met Ala Val Leu Pro Arg Arg Glu Arg Asn Arg Gln Ala Ala
                85                  90                  95

Ala Ala Asn Pro Glu Asn Ser Arg Gly Lys Gly Arg Arg Gly Gln Arg
            100                 105                 110

Gly Lys Asn Arg Gly Cys Val Leu Thr Ala Ile His Leu Asn Val Thr
        115                 120                 125

Asp Leu Gly Leu Gly Tyr Glu Thr Lys Glu Glu Leu Ile Phe Arg Tyr
    130                 135                 140

Cys Ser Gly Ser Cys Asp Ala Ala Glu Thr Thr Tyr Asp Lys Ile Leu
145                 150                 155                 160

Lys Asn Leu Ser Arg Asn Arg Arg Leu Val Ser Asp Lys Val Gly Gln
                165                 170                 175

Ala Cys Cys Arg Pro Ile Ala Phe Asp Asp Asp Leu Ser Phe Leu Asp
            180                 185                 190
```

```
Asp Asn Leu Val Tyr His Ile Leu Arg Lys His Ser Ala Lys Arg Cys
        195                 200                 205

Gly Cys Ile
    210

<210> SEQ ID NO 34
<211> LENGTH: 636
<212> TYPE: DNA
<213> ORGANISM: Homo sapiens
<220> FEATURE:
<221> NAME/KEY: misc_feature
<222> LOCATION: (1)..(636)
<223> OTHER INFORMATION: V64M pre-alfa-pro-GDNF nt

<400> SEQUENCE: 34
atgaagttat gggatgtcgt ggctgtctgc ctggtgctgc tccacaccgc gtccgccttc      60
ccgctgcccg ccggtaagag gcctcccgag gcgcccgccg aagaccgctc cctcggccgc     120
cgccgcgcgc ccttcgcgct gagcagtgac tcaaatatgc cagaggatta tcctgatcag     180
ttcgatgata tgatggattt tattcaagcc accattaaaa gactgaaaag gtcaccagat     240
aaacaaatgg cagtgcttcc tagaagagag cggaatcggc aggctgcagc tgccaaccca     300
gagaattcca gaggaaaagg tcggagaggc cagaggggca aaaaccgggg ttgtgtctta     360
actgcaatac atttaaatgt cactgacttg ggtctgggct atgaaaccaa ggaggaactg     420 attttaggt actgcagcgg ctcttgcgat gcagctgaga caacgtacga caaaatattg     480 aaaacttat ccagaaatag aaggctggtg agtgacaaag tagggcaggc atgttgcaga     540
cccatcgcct ttgatgatga cctgtcgttt ttagatgata acctggttta ccatattcta     600
agaaagcatt ccgctaaaag gtgtggatgt atctga                              636

<210> SEQ ID NO 35
<211> LENGTH: 147
<212> TYPE: PRT
<213> ORGANISM: Homo sapiens
<220> FEATURE:
<221> NAME/KEY: MISC_FEATURE
<222> LOCATION: (1)..(147)
<223> OTHER INFORMATION: truncated pre-beta-pro-GDNF aa

<400> SEQUENCE: 35

Met Lys Leu Trp Asp Val Val Ala Val Cys Leu Val Leu Leu His Thr
1               5                  10                   15

Ala Ser Ala Phe Pro Leu Pro Ala Ala Asn Met Pro Glu Asp Tyr Pro
            20                  25                  30

Asp Gln Phe Asp Asp Val Met Asp Phe Ile Gln Ala Thr Ile Lys Arg
        35                  40                  45

Leu Lys Arg Arg Gly Cys Val Leu Thr Ala Ile His Leu Asn Val Thr
50                  55                  60

Asp Leu Gly Leu Gly Tyr Glu Thr Lys Glu Glu Leu Ile Phe Arg Tyr
65                  70                  75                  80

Cys Ser Gly Ser Cys Asp Ala Ala Glu Thr Thr Tyr Asp Lys Ile Leu
                85                  90                  95

Lys Asn Leu Ser Arg Asn Arg Arg Leu Val Ser Asp Lys Val Gly Gln
            100                 105                 110

Ala Cys Cys Arg Pro Ile Ala Phe Asp Asp Asp Leu Ser Phe Leu Asp
        115                 120                 125

Asp Asn Leu Val Tyr His Ile Leu Arg Lys His Ser Ala Lys Arg Cys
    130                 135                 140
```

-continued

Gly Cys Ile
145

<210> SEQ ID NO 36
<211> LENGTH: 444
<212> TYPE: DNA
<213> ORGANISM: Homo sapiens
<220> FEATURE:
<221> NAME/KEY: misc_feature
<222> LOCATION: (1)..(444)
<223> OTHER INFORMATION: truncated pre-beta-pro-GDNF nt

<400> SEQUENCE: 36

```
atgaagttat gggatgtcgt ggctgtctgc ctggtgctgc tccacaccgc gtccgccttc      60
ccgctgcccg ccgcaaatat gccagaggat tatcctgatc agttcgatga tgtcatggat     120
tttattcaag ccaccattaa aagactgaaa aggcggggtt gtgtcttaac tgcaatacat     180
ttaaatgtca ctgacttggg tctgggctat gaaaccaagg aggaactgat ttttaggtac     240
tgcagcggct cttgcgatgc agctgagaca acgtacgaca aaatattgaa aaacttatcc     300
agaaatagaa ggctggtgag tgacaaagta gggcaggcat gttgcagacc catcgccttt     360
gatgatgacc tgtcgttttt agatgataac ctggtttacc atattctaag aaagcattcc     420
gctaaaaggt gtggatgtat ctga                                            444
```

<210> SEQ ID NO 37
<211> LENGTH: 20
<212> TYPE: DNA
<213> ORGANISM: Artificial sequence
<220> FEATURE:
<223> OTHER INFORMATION: pEGFP 5' primer

<400> SEQUENCE: 37
caacgggact tccaaaatg                                                   20

<210> SEQ ID NO 38
<211> LENGTH: 19
<212> TYPE: DNA
<213> ORGANISM: Artificial sequence
<220> FEATURE:
<223> OTHER INFORMATION: pEGFP 3' primer

<400> SEQUENCE: 38
ggacacgctg aacttgtgg                                                   19

<210> SEQ ID NO 39
<211> LENGTH: 34
<212> TYPE: DNA
<213> ORGANISM: Artificial sequence
<220> FEATURE:
<223> OTHER INFORMATION: Primer 89

<400> SEQUENCE: 39
caacaaggat ccatgaagtt atgggatgtc gtgg                                  34

<210> SEQ ID NO 40
<211> LENGTH: 35
<212> TYPE: DNA
<213> ORGANISM: Artificial sequence
<220> FEATURE:
<223> OTHER INFORMATION: Primer 90

<400> SEQUENCE: 40
ccaccactcg agtcagatac atccacacct tttag                                 35

<210> SEQ ID NO 41
<211> LENGTH: 20
<212> TYPE: DNA
<213> ORGANISM: Artificial sequence
<220> FEATURE:
<223> OTHER INFORMATION: pAAV-MCS 5' primer

<400> SEQUENCE: 41
attctgagtc caagctaggc                                              20

<210> SEQ ID NO 42
<211> LENGTH: 20
<212> TYPE: DNA
<213> ORGANISM: Artificial sequence
<220> FEATURE:
<223> OTHER INFORMATION: pAAV-MCS 3' primer

<400> SEQUENCE: 42
tagaaggaca cctagtcaga                                              20

<210> SEQ ID NO 43
<211> LENGTH: 26
<212> TYPE: PRT
<213> ORGANISM: Homo sapiens
<220> FEATURE:
<221> NAME/KEY: MISC_FEATURE
<222> LOCATION: (1)..(26)
<223> OTHER INFORMATION: The 26 amino acid C-terminal sequence of the
      prepro sequence of any of the GDNF protein splice variants alfa,
      beta or gamma

<400> SEQUENCE: 43

Asn Met Pro Glu Asp Tyr Pro Asp Gln Phe Asp Asp Val Met Asp Phe
1               5                   10                  15

Ile Gln Ala Thr Ile Lys Arg Leu Lys Arg
            20                  25

<210> SEQ ID NO 44
<211> LENGTH: 58
<212> TYPE: PRT
<213> ORGANISM: Homo sapiens
<220> FEATURE:
<221> NAME/KEY: MISC_FEATURE
<222> LOCATION: (1)..(58)
<223> OTHER INFORMATION: pro-peptide of human pre-alfa-pro-GDNF

<400> SEQUENCE: 44

Phe Pro Leu Pro Ala Gly Lys Arg Pro Pro Glu Ala Pro Ala Glu Asp
1               5                   10                  15

Arg Ser Leu Gly Arg Arg Arg Ala Pro Phe Ala Leu Ser Ser Asp Ser
            20                  25                  30

Asn Met Pro Glu Asp Tyr Pro Asp Gln Phe Asp Asp Val Met Asp Phe
        35                  40                  45

Ile Gln Ala Thr Ile Lys Arg Leu Lys Arg
    50                  55

<210> SEQ ID NO 45
<211> LENGTH: 32
<212> TYPE: PRT
<213> ORGANISM: Homo sapiens
<220> FEATURE:
<221> NAME/KEY: MISC_FEATURE
<222> LOCATION: (1)..(32)
<223> OTHER INFORMATION: pro-peptide of human pre-beta-pro-GDNF

<400> SEQUENCE: 45

```
Phe Pro Leu Pro Ala Ala Asn Met Pro Glu Asp Tyr Pro Asp Gln Phe
1               5                   10                  15

Asp Asp Val Met Asp Phe Ile Gln Ala Thr Ile Lys Arg Leu Lys Arg
            20                  25                  30

<210> SEQ ID NO 46
<211> LENGTH: 21
<212> TYPE: PRT
<213> ORGANISM: Artificial sequence
<220> FEATURE:
<223> OTHER INFORMATION: epitope for antibody 320 (based on mouse
      alfa-pro sequence)

<400> SEQUENCE: 46

Cys Gly Lys Arg Leu Leu Glu Ala Pro Ala Glu Asp His Ser Leu Gly
1               5                   10                  15

His Arg Arg Val Pro
            20

<210> SEQ ID NO 47
<211> LENGTH: 14
<212> TYPE: PRT
<213> ORGANISM: Artificial sequence
<220> FEATURE:
<223> OTHER INFORMATION: epitope for antibody 321 (based on C-terminus
      of pro-GDNF)

<400> SEQUENCE: 47

Cys Pro Glu Asp Tyr Pro Asp Gln Phe Asp Asp Val Met Asp
1               5                   10

<210> SEQ ID NO 48
<211> LENGTH: 14
<212> TYPE: PRT
<213> ORGANISM: Artificial sequence
<220> FEATURE:
<223> OTHER INFORMATION: epitope for antibody 322 (based on beta-pro
      sequence)

<400> SEQUENCE: 48

Cys His Thr Ala Ser Ala Phe Pro Leu Pro Ala Ala Asn Met
1               5                   10

<210> SEQ ID NO 49
<211> LENGTH: 77
<212> TYPE: PRT
<213> ORGANISM: Homo sapiens
<220> FEATURE:
<221> NAME/KEY: MISC_FEATURE
<222> LOCATION: (1)..(77)
<223> OTHER INFORMATION: pre-pro region of pre-alfa-pro-GDNF

<400> SEQUENCE: 49

Met Lys Leu Trp Asp Val Val Ala Val Cys Leu Val Leu Leu His Thr
1               5                   10                  15

Ala Ser Ala Phe Pro Leu Pro Ala Gly Lys Arg Pro Glu Ala Pro
            20                  25                  30

Ala Glu Asp Arg Ser Leu Gly Arg Arg Arg Ala Pro Phe Ala Leu Ser
        35                  40                  45

Ser Asp Ser Asn Met Pro Glu Asp Tyr Pro Asp Gln Phe Asp Asp Val
    50                  55                  60

Met Asp Phe Ile Gln Ala Thr Ile Lys Arg Leu Lys Arg
65                  70                  75
```

-continued

<210> SEQ ID NO 50
<211> LENGTH: 51
<212> TYPE: PRT
<213> ORGANISM: Homo sapiens
<220> FEATURE:
<221> NAME/KEY: MISC_FEATURE
<222> LOCATION: (1)..(51)
<223> OTHER INFORMATION: pre-pro region of pre-beta-pro-GDNF

<400> SEQUENCE: 50

Met Lys Leu Trp Asp Val Val Ala Val Cys Leu Val Leu Leu His Thr
 1               5                  10                  15
Ala Ser Ala Phe Pro Leu Pro Ala Ala Asn Met Pro Glu Asp Tyr Pro
            20                  25                  30
Asp Gln Phe Asp Asp Val Met Asp Phe Ile Gln Ala Thr Ile Lys Arg
        35                  40                  45
Leu Lys Arg
    50

<210> SEQ ID NO 51
<211> LENGTH: 558
<212> TYPE: DNA
<213> ORGANISM: Homo sapiens
<220> FEATURE:
<221> NAME/KEY: CDS
<222> LOCATION: (1)..(555)
<220> FEATURE:
<221> NAME/KEY: misc_feature
<222> LOCATION: (1)..(558)
<223> OTHER INFORMATION: human pre-beta-pro-GDNF
<220> FEATURE:
<221> NAME/KEY: sig_peptide
<222> LOCATION: (1)..(57)
<220> FEATURE:
<221> NAME/KEY: misc_feature
<222> LOCATION: (58)..(153)
<223> OTHER INFORMATION: pro-peptide
<220> FEATURE:
<221> NAME/KEY: mat_peptide
<222> LOCATION: (154)..(555)

<400> SEQUENCE: 51 atg aag tta tgg gat gtc gtg gct gtc tgc ctg gtg ctg ctc cac acc    48
Met Lys Leu Trp Asp Val Val Ala Val Cys Leu Val Leu Leu His Thr
 -50              -45                 -40 gcg tcc gcc ttc ccg ctg ccc gcc gca aat atg cca gag gat tat cct    96
Ala Ser Ala Phe Pro Leu Pro Ala Ala Asn Met Pro Glu Asp Tyr Pro
-35                 -30                  -25                 -20 gat cag ttc gat gat gtc atg gat ttt att caa gcc acc att aaa aga   144
Asp Gln Phe Asp Asp Val Met Asp Phe Ile Gln Ala Thr Ile Lys Arg
                -15                 -10                  -5 ctg aaa agg tca cca gat aaa caa atg gca gtg ctt cct aga aga gag   192
Leu Lys Arg Ser Pro Asp Lys Gln Met Ala Val Leu Pro Arg Arg Glu
 -1  1               5                  10 cgg aat cgg cag gct gca gct gcc aac cca gag aat tcc aga gga aaa   240
Arg Asn Arg Gln Ala Ala Ala Ala Asn Pro Glu Asn Ser Arg Gly Lys
        15                  20                  25 ggt cgg aga ggc cag agg ggc aaa aac cgg ggt tgt gtc tta act gca   288
Gly Arg Arg Gly Gln Arg Gly Lys Asn Arg Gly Cys Val Leu Thr Ala
 30                  35                  40                  45 ata cat tta aat gtc act gac ttg ggt ctg ggc tat gaa acc aag gag   336
Ile His Leu Asn Val Thr Asp Leu Gly Leu Gly Tyr Glu Thr Lys Glu
                 50                  55                  60 gaa ctg att ttt agg tac tgc agc ggc tct tgc gat gca gct gag aca   384
Glu Leu Ile Phe Arg Tyr Cys Ser Gly Ser Cys Asp Ala Ala Glu Thr

```
                        65                  70                  75
acg tac gac aaa ata ttg aaa aac tta tcc aga aat aga agg ctg gtg          432
Thr Tyr Asp Lys Ile Leu Lys Asn Leu Ser Arg Asn Arg Arg Leu Val
            80                  85                  90 agt gac aaa gta ggg cag gca tgt tgc aga ccc atc gcc ttt gat gat          480
Ser Asp Lys Val Gly Gln Ala Cys Cys Arg Pro Ile Ala Phe Asp Asp
    95                  100                 105 gac ctg tcg ttt tta gat gat aac ctg gtt tac cat att cta aga aag          528
Asp Leu Ser Phe Leu Asp Asp Asn Leu Val Tyr His Ile Leu Arg Lys
110                 115                 120                 125 cat tcc gct aaa agg tgt gga tgt atc tga                                  558
His Ser Ala Lys Arg Cys Gly Cys Ile
                130

<210> SEQ ID NO 52
<211> LENGTH: 185
<212> TYPE: PRT
<213> ORGANISM: Homo sapiens

<400> SEQUENCE: 52

Met Lys Leu Trp Asp Val Val Ala Val Cys Leu Val Leu Leu His Thr
    -50                 -45                 -40

Ala Ser Ala Phe Pro Leu Pro Ala Ala Asn Met Pro Glu Asp Tyr Pro
-35                 -30                 -25                 -20

Asp Gln Phe Asp Asp Val Met Asp Phe Ile Gln Ala Thr Ile Lys Arg
                -15                 -10                 -5

Leu Lys Arg Ser Pro Asp Lys Gln Met Ala Val Leu Pro Arg Arg Glu
            -1  1               5                   10

Arg Asn Arg Gln Ala Ala Ala Asn Pro Glu Asn Ser Arg Gly Lys
        15                  20                  25

Gly Arg Arg Gly Gln Arg Gly Lys Asn Arg Gly Cys Val Leu Thr Ala
30                  35                  40                  45

Ile His Leu Asn Val Thr Asp Leu Gly Leu Gly Tyr Glu Thr Lys Glu
                50                  55                  60

Glu Leu Ile Phe Arg Tyr Cys Ser Gly Ser Cys Asp Ala Ala Glu Thr
                65                  70                  75

Thr Tyr Asp Lys Ile Leu Lys Asn Leu Ser Arg Asn Arg Arg Leu Val
            80                  85                  90

Ser Asp Lys Val Gly Gln Ala Cys Cys Arg Pro Ile Ala Phe Asp Asp
    95                  100                 105

Asp Leu Ser Phe Leu Asp Asp Asn Leu Val Tyr His Ile Leu Arg Lys
110                 115                 120                 125

His Ser Ala Lys Arg Cys Gly Cys Ile
                130
```